United States Patent
Nirogi et al.

(10) Patent No.: US 10,294,217 B2
(45) Date of Patent: May 21, 2019

(54) FLUOROINDOLE DERIVATIVES AS MUSCARINIC M1 RECEPTOR POSITIVE ALLOSTERIC MODULATORS

(71) Applicant: Suven Life Sciences Limited, Banjara Hills, Hyderabad, Telangana (IN)

(72) Inventors: Ramakrishna Nirogi, Telangana (IN); Anil Karbhari Shinde, Telangana (IN); Abdul Rasheed Mohammed, Telangana (IN); Ramkumar Subramanian, Telangana (IN); Vijay Sidram Benade, Telangana (IN); Gopinadh Bhyrapuneni, Telangana (IN); Venkateswarlu Jasti, Telangana (IN)

(73) Assignee: Suven Life Sciences Limited, Banjara Hills, Hyderabad (IN)

( * ) Notice: Subject to any disclaimer, the term of this patent is extended or adjusted under 35 U.S.C. 154(b) by 0 days.

(21) Appl. No.: 15/758,313

(22) PCT Filed: Jul. 19, 2016

(86) PCT No.: PCT/IB2016/054290
§ 371 (c)(1),
(2) Date: Mar. 7, 2018

(87) PCT Pub. No.: WO2017/042643
PCT Pub. Date: Mar. 16, 2017

(65) Prior Publication Data
US 2018/0244655 A1 Aug. 30, 2018

(30) Foreign Application Priority Data
Sep. 10, 2015 (IN) .......................... 4809/CHE/2015

(51) Int. Cl.
*A61P 25/28* (2006.01)
*C07D 401/06* (2006.01)
*C07D 401/12* (2006.01)
*C07D 401/14* (2006.01)
*C07D 403/06* (2006.01)
*C07D 403/14* (2006.01)
*C07D 417/06* (2006.01)
*C07D 417/14* (2006.01)

(52) U.S. Cl.
CPC ............ *C07D 403/06* (2013.01); *A61P 25/28* (2018.01); *C07D 401/06* (2013.01); *C07D 401/12* (2013.01); *C07D 401/14* (2013.01); *C07D 403/14* (2013.01); *C07D 417/06* (2013.01); *C07D 417/14* (2013.01)

(58) Field of Classification Search
CPC ..... A61P 25/28; C07D 401/06; C07D 401/12; C07D 401/14; C07D 403/06; C07D 403/14; C07D 417/06; C07D 417/14
See application file for complete search history.

(56) References Cited

U.S. PATENT DOCUMENTS

2015/0094328 A1 4/2015 Payne et al.

FOREIGN PATENT DOCUMENTS

| WO | 2007067489 A1 | 6/2007 | |
|---|---|---|---|
| WO | 2011084368 A1 | 7/2011 | |
| WO | 2011149801 A1 | 12/2011 | |
| WO | 2015028483 A1 | 3/2015 | |
| WO | 2015044072 A1 | 4/2015 | |
| WO | 2015049574 A1 | 4/2015 | |
| WO | WO-2015044072 A1 * | 4/2015 | ........... C07D 405/14 |
| WO | 2015080904 A2 | 6/2015 | |

OTHER PUBLICATIONS

Patani et al. "Bioisoterism: A Rational Approach in Drug Design" Chemical Reviews, 1996, vol. 96, pp. 3147-3176. (Year: 1996).*
Ennaceur A and Delacour J, "A new one-trial test for neurobiological studies of memory in rats. 1: Behavioural data", Behav Brain Res 31:47-59, 1988.
Lin JH, "CSF as a surrogate for assessing CNS exposure: An industrial perspective," Current Drug Metab 9:46-59, 2008.
Schmidt S et al., "Signigicance of protein binding in pharmacokinetics and pharmacodynamics," 99:1107-1122, 2010 (Published online Oct. 22, 2009 DOI 10.1002/jps.21916).
Hammarlund-Udenaes M et al. "On the rate and extent of drug delivery to the brain," Pharma Res. 25:1737-1750, 2008 (Published online Dec. 5, 2007 DOI: 10.1007/s11095-007-9502-2).
Trainor GL, "The importance of plasma protein binding in drug discovery," Expert Opin Drug Discov 2:51-64, 2007.
Liu X et al., "Strategies to optimize brain penetration in drug discovery," Curr Opin Drug Discov Devel. 8:505-512, 2005.

(Continued)

*Primary Examiner* — Joseph R Kosack
(74) *Attorney, Agent, or Firm* — K&L Gates LLP; Louis C. Cullman; Michelle Glasky Bergman

(57) ABSTRACT

The present invention relates to compound of formula (I), or stereoisomers and pharmaceutically acceptable salts as muscarinic M1 receptor positive allosteric modulators. This invention also relates to methods of making such compounds and pharmaceutical compositions comprising such compounds. The compounds of this invention are useful in the treatment of various disorders that are related to muscarinic M1 receptor. (Formula I)(I)

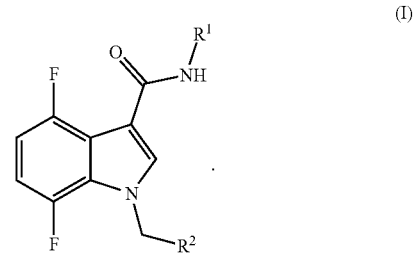

8 Claims, 2 Drawing Sheets

(56) References Cited

OTHER PUBLICATIONS

Kuduk SD et al., Pyridine containing M(1) positive allosteric modulators with reduced plasma protein binding. Bioorg Med Chem Lett. 20:657-61, 2010.

Kuduk SD et al., "Quinolizidinone carboxylic acids as CNS penetrant, selective M1 allosteric muscarinic receptor modulators," ACS Med Chem Lett, 1:263-267, 2010.

Wess J, "Molecular biology of muscarinic acetylcholine receptors," Critical Rev Neurobio 10:69-99, 1996.

Uslaner JM et al., "The muscarinic M1 receptor positive allosteric modulator PQCA improves cognitive measures in rat, cynomolgus macaque, and rhesus macaque," Psychopharmaol 225:51-30, 2013.

Veroff AE et al., "Efficacy of Xanomeline in Alzheimer's Disease: Cognitive improvement measured using the Computerized Neuropsychological Test Battery (CNTB)," Alz Dis Assoc Disord 12:304-312, 1998.

Levey AI, "Chronically mad as a hatter: Anticholinergics and Alzheimer's Disease pathology," Ann Neurol 54:144-146, 2003.

Levey AI, "Immunological localization of m1-m5 muscarinic acetylcholine receptors in peripheral tissues and brain," Life Sci 52:441-448, 1993.

Langmead CJ et al., "Muscarinic acetylcholine receptors as CNS drug targets," Pharmacol Thera 117:232-243, 2008.

Lanz TA et al., "The gamma-secretase inhibitor N-[N-(3,5-difluorophenacetyl)-L-alanyl]-S-phenylglycine t-butyl ester reduces A-beta levels in vivo in plasma and cerebrospinal fluid in young (Plaque-Free) and aged (plaque-bearing) Tg2576 mice," J Pharmacol Exp Thera 305:864-871, 2003.

Fisher A, "Cholinergic treatments with emphasis on M1 muscarinic agonists as potential disease-modifying agents for Alzheimer's Disease," Neurotherapeutics 5:433-442, 2008.

Shirey JK et al., "A selective allosteric potentiator of the M1 muscarinic acetylcholine receptor increases activity of medial prefrontal cortical neurons and restores impairments in reversal learning," J Neurosci 29:14271-14286, 2009.

* cited by examiner

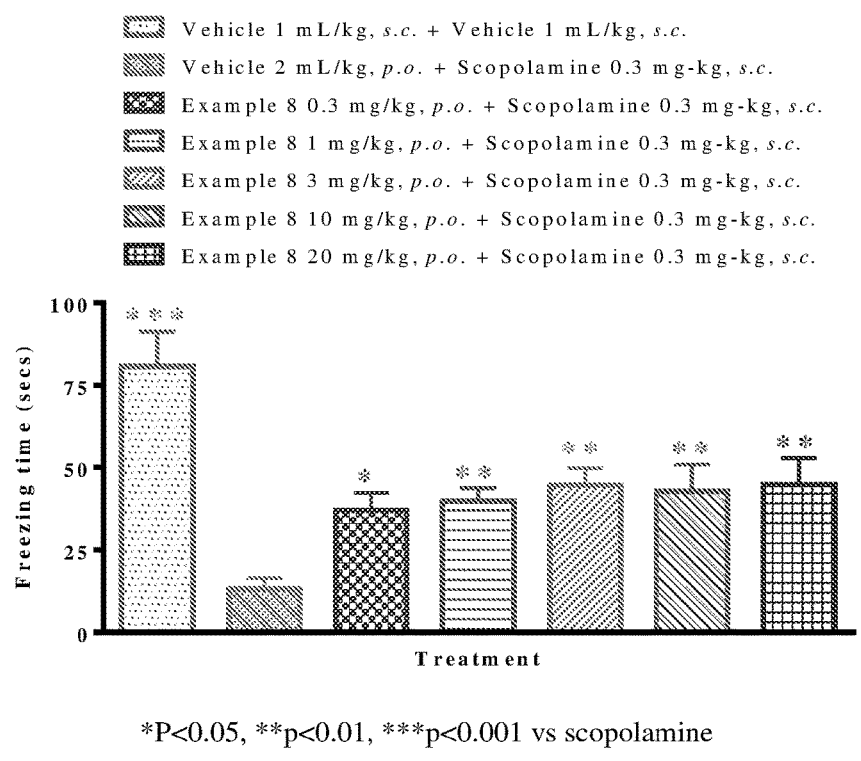
Figure 1: Effect of test compound on Contextual fear conditioning task

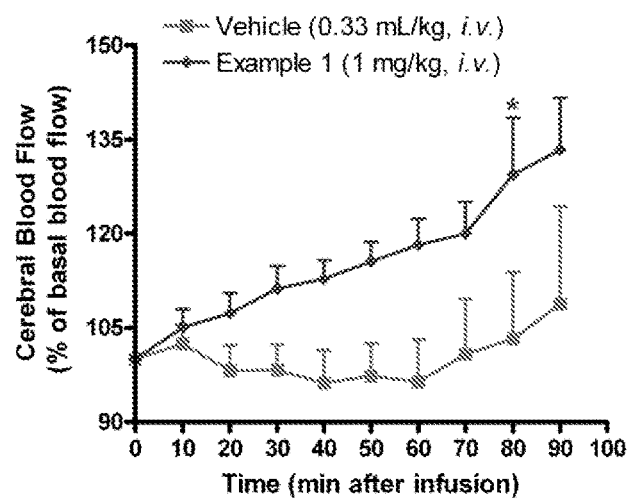
*p<0.05 vs. vehicle, Two-way ANOVA followed by Bonferroni post tests, n=6-8
Figure 2: Effect of test compound on modulation of cerebral blood flow in the frontal cortex

FLUOROINDOLE DERIVATIVES AS MUSCARINIC M1 RECEPTOR POSITIVE ALLOSTERIC MODULATORS

FIELD OF INVENTION

The present invention relates to compounds of formula (I), or their isotopic forms, stereoisomers, or pharmaceutically acceptable salts as muscarinic M1 receptor positive allosteric modulators (M1 PAMs). The present invention also describes method of making such compounds, pharmaceutical compositions comprising such compounds and their use.

BACKGROUND OF THE INVENTION

Muscarinic acetylcholine receptors (mAChRs) which belong to the class A family of G protein-coupled receptors (GPCRs), are widely expressed throughout the body. Five subtypes termed M1 through M5 that respond to the endogenous neurotransmitter acetylcholine (ACh) has been identified till date. They play key role in regulating the activity of many important functions of the central and peripheral nervous system including cognitive function. M1, M3 and M5 couple to Gq, whereas M2 and M4 couple via Gi/o to downstream signaling pathways and associated effector systems (*Critical Reviews in Neurobiology*, 1996, 10, 69-99; *Pharmacology & Therapeutics*, 2008, 117, 232-243). M2 and M3 are highly expressed in the periphery and are known to be involved in gastrointestinal (GI) motility and parasympathetic responses such as salivation (*Life Sciences*, 1993, 52, 441-448). The M1 muscarinic receptor is predominantly expressed in the brain regions such as cortex, hippocampus and amygdala which involved in cognition, and therefore selective activation of the M1 receptor would be expected to boost cognitive performance (*Annals of Neurology*, 2003, 54, 144-146).

Xanomeline, a muscarinic acetylcholine receptor agonist with reasonable selectivity for the M1 and M4 subtypes, produced significant effects on cognition in a clinical Alzheimer's disease (AD) trial (*Alzheimer Disease and Associated Disorders*, 1998, 12(4), 304-312) although gastrointestinal side effects led to a high dropout rate in clinical trials. There is a high degree of conservation between muscarinic receptor subtypes at their orthosteric acetylcholine ligand binding sites which makes it difficult to identify a M1 selective agonist.

To circumvent this issue of selectivity and safety, an alternative approach consists of developing M1 PAMs that act at the less conserved allosteric binding site. Merck reported the development of M1 PAM, PQCA (1-{[4-cyano-4-(pyridine-2-yl) piperidin-1-yl] methyl}-4-oxo-4H-quinolizine-3-carboxylic acid). This compound is highly selective for M1 over the other muscarinic receptor subtypes and found to be efficacious in several preclinical models of cognition (*Psychopharmacology*, 2013, 225(1), 21-30) with no gastrointestinal side effects at doses equal to or less than a fivefold margin from the minimum effective dose required to improve cognition. In preclinical studies it was demonstrated that M1 activation increases neurotransmitter acetylcholine concentration in brain. Moreover, the M1 activation has potential as disease-modifying therapy for AD by both shifting the APP processing towards the non-amyloidogenic α-secretase pathway and by decreasing the tau hyper-phosphorylation. Positive allosteric modulators at M1 receptor have demonstrated to increase the generation of sAPPα in-vitro (*The Journal of Neuroscience*, 2009, 29, 14271-14286). Therefore, M1 PAMs provide an approach to target both symptomatic and disease-modifying treatment of cognitive deficits in AD and schizophrenia.

PCT patent application publications, WO2015049574A1, WO2015044072A1, WO2015028483, WO2007067489, and WO2011149801 have disclosed some M1 PAM compounds. The PCT patent application, WO2001058869 and U.S. Pat. No. 4,616,009 discloses some of indole compounds useful in medicaments. While several M1 PAMs have been disclosed in the literature till date, no drug acting as M1 PAM is launched in the market.

For drugs with an intended action in the central nervous system (CNS), the compound should cross the blood brain barrier or in other words the compounds should possess brain penetration properties. It is a commonly accepted hypothesis that unbound or free drug is available for interaction with pharmacological and toxicological targets in the brain. This hypothesis is referred to as the free drug hypothesis in pharmacokinetics (*Current Opinion in Drug Discovery & Development*, 2005, 8, 505-512; *Expert Opinion on Drug Discovery*, 2007, 2, 51-64; *Pharmaceutical Research*, 2008, 25, 1737-1750; *Current Drug Metabolism*, 2008, 9, 46-59; *Journal of Pharmaceutical Sciences*, 2010, 99, 1107-1122).

Although the prior arts disclose M1 PAM compounds that are useful in the treatment of CNS related diseases, there exist an issue of poor brain penetration and free fraction availability. Therefore, there is an un-met need and scope to discover and develop new M1 PAMs with good brain penetration and adequate free fraction. Such compounds may have efficacy at much lower doses thereby increasing the margin of safety over the efficacy dose. The M1 PAM compounds of the instant invention solve the issue of brain penetration as well as the free fraction availability in the brain thereby very effective in the treatment of CNS related disorders.

SUMMARY OF THE INVENTION

In first aspect, the present invention relates to muscarinic M1 receptor PAMs of compound of formula (I),

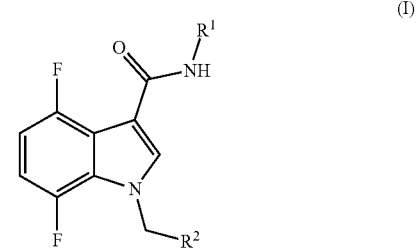

wherein:
R¹ is

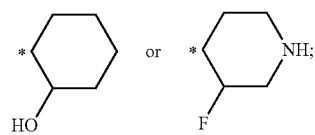

R² is

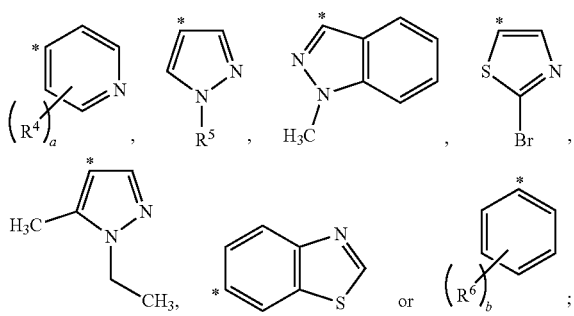

provided that when R¹ is

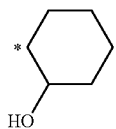

then R² is other than

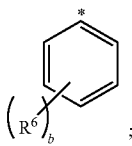

wherein * represents point of attachment;
R³ is fluorine or hydrogen;
R⁴ is halogen, —S—CH₃ or hydrogen;
R⁵ is —CH₃, —CH₂CH₂F or hydrogen;
R⁶ is halogen, —O—CH₃ or hydrogen;
a is 1 or 2; and
b is 1 or 2;
or an isotopic form, a stereoisomer or a pharmaceutically acceptable salt thereof.

In another aspect, the present invention relates to the processes for preparing the compound of formula (I), or a stereoisomer and a pharmaceutically acceptable salt thereof.

In yet another aspect, the present invention relates to pharmaceutical composition containing a therapeutically effective amount of at least one compound of formula (I), or a stereoisomer and a pharmaceutically acceptable salt thereof and pharmaceutically acceptable excipients or carriers.

In yet another aspect, the present invention relates to compound of formula (I), or a stereoisomer and a pharmaceutically acceptable salt thereof, for use as M1 PAM.

In yet another aspect, the present invention relates to compound of formula (I), or a stereoisomer and a pharmaceutically acceptable salt thereof, for use in the treatment of various disorders selected from AD, schizophrenia, cognitive disorders, pain or sleep disorders.

In another aspect, the present invention relates to a method for the treatment of disorders related to muscarinic M1 receptor, comprising administering to a patient in need thereof, a therapeutically effective amount of a compound of formula (I), or a stereoisomer and a pharmaceutically acceptable salt thereof.

In yet another aspect, the present invention relates to use of the compound of formula (I), or stereoisomers and pharmaceutically acceptable salts thereof, for the manufacture of a medicament for the treatment of disorders related to muscarinic M1 receptor.

In yet another aspect, the present invention relates to compound of formula (I) for use in positive allosteric modulation of muscarinic M1 receptor.

BRIEF DESCRIPTION OF DRAWINGS

FIG. 1: Effect of test compound on contextual fear conditioning task
FIG. 2: Effect of test compound on modulation of cerebral blood flow in the frontal cortex

DETAILED DESCRIPTION OF THE INVENTION

Unless otherwise stated, the following terms used in the specification and claims have the meanings given below:
The term "halogen" means fluorine, chlorine, bromine or iodine.
The phrase, "therapeutically effective amount" is defined as an amount of a compound of the present invention that (i) treats the particular disease, condition or disorder (ii) eliminates one or more symptoms of the particular disease, condition or disorder (iii) delays the onset of one or more symptoms of the particular disease, condition or disorder described herein.
The term, "isotopic form" as used herein refers to the compound of formula (I) wherein one or more atoms of compound of formula (I) are substituted by their respective isotopes. For example, isotopes of hydrogen include ²H (deuterium) and ³H (tritium).
The term, "stereoisomers" as used herein refers to isomers of compound of formula (I) that differ in the arrangement of their atoms in space. Compounds disclosed herein may exist as single stereoisomers, racemates and/or mixtures of enantiomers and/or diastereomers. All such single stereoisomers, racemates and mixtures thereof are intended to be within the scope of the present invention.
The term, "pharmaceutically acceptable salt" as used herein refers to salts of the active compound i.e. the compound of formula I, and are prepared by reaction with the appropriate acid or acid derivative, depending on the particular substituents found on the compounds described herein.
WO2015044072A1 patent application discloses indole derivatives as M1 PAM compounds. Based on the available in vitro data disclosed in the patent, three of the most potent compounds (Example number 30, 76 and 77) were synthesized in our laboratories and tested for its pharmacokinetic and brain penetration properties in Wistar rats. All the three compounds were found to have poor brain penetration. This makes these compounds less ideal for the treatment of CNS disorders. The M1 PAM compounds of the instant invention possess brain penetration and/or free fraction available in the brain which will make them useful compounds to further develop for the treatment of CNS disorders.

Embodiments

The present invention encompasses all the compounds described by the compound of formula (I) without limitation, however, preferred aspects and elements of the invention are discussed herein in the form of the following embodiments.

In one embodiment, the present invention relates to the compound of formula (I), wherein:

$R^1$ is

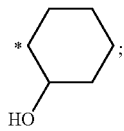

$R^2$ is other than

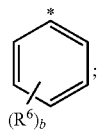

wherein * represents point of attachment; $R^6$ and b are as defined in the first aspect; or an isotopic form, a stereoisomer or a pharmaceutically acceptable salt thereof.

In another embodiment, the present invention relates to the compound of formula (I), wherein:
$R^1$ is

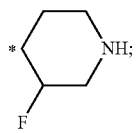

wherein * represents point of attachment; or an isotopic form, a stereoisomer or a pharmaceutically acceptable salt thereof.

In another embodiment, the present invention relates to the compound of formula (I), wherein:
$R^2$ is

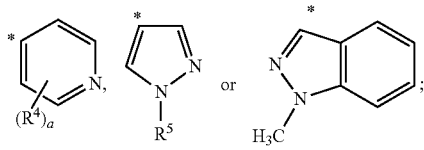

wherein * represents point of attachment; $R^4$, $R^5$ and a are as defined in the first aspect; or an isotopic form, a stereoisomer or a pharmaceutically acceptable salt thereof.

In another embodiment, the present invention relates to the compound of formula (I), wherein:
$R^2$ is

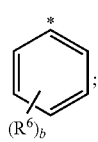

wherein * represents point of attachment; $R^6$ and b are as defined in the first aspect; or an isotopic form, a stereoisomer or a pharmaceutically acceptable salt thereof.

In another embodiment, the present invention relates to the compound of formula (I), wherein:
$R^2$ is

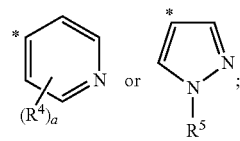

wherein * represents point of attachment; $R^4$, $R^5$ and a are as defined in the first aspect; or an isotopic form, a stereoisomer or a pharmaceutically acceptable salt thereof.

In another embodiment, the present invention relates to the compound of formula (I), wherein:
$R^2$ is

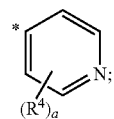

wherein * represents point of attachment; $R^4$ and a are as defined in the first aspect; or an isotopic form, a stereoisomer or a pharmaceutically acceptable salt thereof.

In another embodiment, the present invention relates to the compound of formula (I), wherein:
$R^2$ is

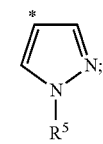

wherein * represents point of attachment; $R^5$ is as defined in the first aspect; or an isotopic form, a stereoisomer or a pharmaceutically acceptable salt thereof.

In another embodiment, the present invention relates to the compound of formula (I), wherein: $R^3$ is fluorine; or an isotopic form, a stereoisomer or a pharmaceutically acceptable salt thereof.

In another embodiment, the present invention relates to the compound of formula (I), wherein:
$R^1$ is

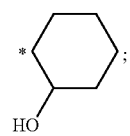

$R^2$ is

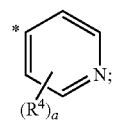

wherein * represents point of attachment; $R^4$ and a are as defined in the first aspect; or an isotopic form, a stereoisomer or a pharmaceutically acceptable salt thereof.

In another embodiment, the present invention relates to the compound of formula (I), wherein:
R¹ is

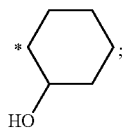

R² is

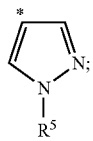

wherein * represents point of attachment; R⁵ is as defined in the first aspect; or an isotopic form, a stereoisomer or a pharmaceutically acceptable salt thereof.

In another embodiment, the present invention relates to the compound of formula (I), wherein:
R¹ is

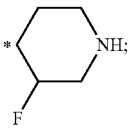

R² is

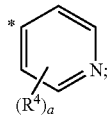

wherein * represents point of attachment; R⁴ and a are as defined in the first aspect; or an isotopic form, a stereoisomer or a pharmaceutically acceptable salt thereof.

In another embodiment, the present invention relates to the compound of formula (I), wherein:
R¹ is

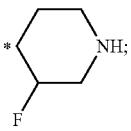

R² is

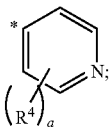

wherein * represents point of attachment; R⁴ is fluorine; a is as defined in the first aspect; or an isotopic form, a stereoisomer or a pharmaceutically acceptable salt thereof.

In another embodiment, the present invention relates to compound of formula (I), wherein:
R¹ is

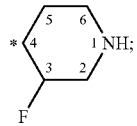

wherein the compound is racemic mixture.

In another embodiment, the present invention relates to compound of formula (I), wherein:
R¹ is

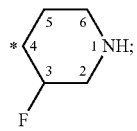

wherein the configuration of chiral centers at C3 and C4 atoms are (3R,4R), (3S,4S), (4R,3S) or (4S,3R).

In yet another embodiment the representative compounds of the present invention includes but not limited to,
N-[(1S,2S)-2-Hydroxycyclohexyl]-1-(1-methyl-1H-pyrazol-4-ylmethyl)-4-fluoro-1H-indole-3-carboxamide;
N-[(1S,2S)-2-Hydroxycyclohexyl]-1-(2-Chloropyridin-4-ylmethyl)-4-fluoro-1H-indole-3-carboxamide;
N-[(1R,2R)-2-Hydroxycyclohexyl]-1-(1-methyl-1H-pyrazol-4-ylmethyl)-4-fluoro-1H-indole-3-carboxamide;
N-[(1S,2S)-2-Hydroxycyclohexyl]-1-(1-methyl-1H-indazol-3-ylmethyl)-4,7-difluoro-1H-indole-3-carboxamide;
N-[(1S,2S)-2-Hydroxycyclohexyl]-1-(1-methyl-1H-pyrazol-4-ylmethyl)-4,7-difluoro-1H-indole-3-carboxamide;
N-[(1S,2S)-2-Hydroxycyclohexyl]-1-(2-Chloropyridin-4-ylmethyl)-4,7-difluoro-1H-indole-3-carboxamide;
N-[(1S,2S)-2-Hydroxycyclohexyl]-1-(2-fluoropyridin-4-ylmethyl)-4-fluoro-1H-indole-3-carboxamide;
N-[(1S,2S)-2-Hydroxycyclohexyl]-1-(2-fluoropyridin-4-ylmethyl)-4,7-difluoro-1H-indole-3-carboxamide;
N-[(1S,2S)-2-Hydroxycyclohexyl]-1-(3-fluoropyridin-4-ylmethyl)-4-fluoro-1H-indole-3-carboxamide;
N-[(1S,2S)-2-Hydroxycyclohexyl]-1-(5-fluoropyridin-4-ylmethyl)-4,7-difluoro-1H-indole-3-carboxamide;
N-[(1S,2S)-2-Hydroxycyclohexyl]-1-(2,5-difluoropyridin-4-ylmethyl)-4-fluoro-1H-indole-3-carboxamide;
N-[(1S,2S)-2-Hydroxycyclohexyl]-1-(2,5-difluoropyridin-4-ylmethyl)-4,7-difluoro-1H-indole-3-carboxamide;
N-[(1S,2S)-2-Hydroxycyclohexyl]-1-(2,3-difluoropyridin-4-ylmethyl)-4-fluoro-1H-indole-3-carboxamide;
N-[(1S,2S)-2-Hydroxycyclohexyl]-1-(1-pyridin-4-ylmethyl)-4-fluoro-1H-indole-3-carboxamide;
N-[(1S,2S)-2-Hydroxycyclohexyl]-1-(1H-pyrazol-4-ylmethyl)-4-fluoro-1H-indole-3-carboxamide;
N-[(1S,2S)-2-Hydroxycyclohexyl]-1-(2-bromothiazol-5-ylmethyl)-4-fluoro-1H-indole-3-carboxamide;
N-[(1S,2S)-2-Hydroxycyclohexyl]-1-(1-ethyl-5-methyl-1H-pyrazol-4-ylmethyl)-4-fluoro-1H-indole-3-carboxamide;

N-[(1S,2S)-2-Hydroxycyclohexyl]-1-(benzothiazol-6-ylmethyl)-4-fluoro-1H-indole-3-carboxamide;
N-[(1S,2S)-2-Hydroxycyclohexyl]-1-(1-(2-fluoroethyl)-1H-pyrazol-4-ylmethyl)-4-fluoro-1H-indole-3-carboxamide;
N-[(1S,2S)-2-Hydroxycyclohexyl]-1-(2-methylsulfanylpyridin-4-ylmethyl)-4,7-difluoro-1H-indole-3-carboxamide;
N-[(1S,2S)-2-Hydroxycyclohexyl]-1-(2-methylsulfanylpyridin-4-ylmethyl)-4-fluoro-1H-indole-3-carboxamide;
cis-N-(3-Fluoropiperidin-4-yl)-1-(2-fluoropyridin-4-ylmethyl)-4,7-difluoro-1H-indole-3-carboxamide (Isomer-II);
trans-N-(3-Fluoropiperidin-4-yl)-1-(2-fluoropyridin-4-ylmethyl)-4,7-difluoro-1H-indole-3-carboxamide (Isomer-I);
trans-N-(3-Fluoropiperidin-4-yl)-1-(2-fluoropyridin-4-ylmethyl)-4,7-difluoro-1H-indole-3-carboxamide (Isomer-II);
cis-N-(3-Fluoropiperidin-4-yl)-1-(5-fluoropyridin-4-ylmethyl)-4,7-difluoro-1H-indole-3-carboxamide (Isomer-I);
cis-N-(3-Fluoropiperidin-4-yl)-1-(2-chloropyridin-4-ylmethyl)-4-fluoro-1H-indole-3-carboxamide (Isomer-I);
cis-N-(3-Fluoropiperidin-4-yl)-1-(2-chloropyridin-4-ylmethyl)-4,7-difluoro-1H-indole-3-carboxamide (Racemate);
cis-N-(3-Fluoropiperidin-4-yl)-1-(2-chloropyridin-4-ylmethyl)-4,7-difluoro-1H-indole-3-carboxamide (Isomer-I);
cis-N-(3-Fluoropiperidin-4-yl)-1-(4-fluorobenzyl)-4-fluoro-1H-indole-3-carboxamide (Isomer-I);
cis-N-(3-Fluoropiperidin-4-yl)-1-(4-fluorobenzyl)-4,7-difluoro-1H-indole-3-carboxamide (Isomer-I);
cis-N-(3-Fluoropiperidin-4-yl)-1-(4-fluorobenzyl)-4,7-difluoro-1H-indole-3-carboxamide (Isomer-II);
cis-N-(3-Fluoropiperidin-4-yl)-1-(2-fluoro benzyl)-4-fluoro-1H-indole-3-carboxamide (Isomer-I);
cis-N-(3-Fluoropiperidin-4-yl)-1-(4-chlorobenzyl)-4-fluoro-1H-indole-3-carboxamide (Isomer-I);
cis-N-(3-Fluoropiperidin-4-yl)-4-fluoro-1-(3-methoxybenzyl)-1H-indole-3-carboxamide (Isomer-I);
cis-N-(3-Fluoropiperidin-4-yl)-4-fluoro-1-(3-methoxybenzyl)-1H-indole-3-carboxamide (Isomer-II);
cis-N-(3-Fluoropiperidin-4-yl)-1-(4-methoxybenzyl)-4-fluoro-1H-indole-3-carboxamide (Isomer-II);
cis-N-(3-Fluoropiperidin-4-yl)-1-(4-methoxybenzyl)-4-fluoro-1H-indole-3-carboxamide (Isomer-I);
cis-N-(3-Fluoropiperidin-4-yl)-1-(4-methoxybenzyl)-4,7-difluoro-1H-indole-3-carboxamide (Isomer-I);
cis-N-(3-Fluoropiperidin-4-yl)-1-(4-methoxybenzyl)-4,7-difluoro-1H-indole-3-carboxamide (Isomer-II);
cis-N-(3-Fluoropiperidin-4-yl)-1-(3,4-difluorobenzyl)-4-fluoro-1H-indole-3-carboxamide (Isomer-I);
cis-N-(3-Fluoropiperidin-4-yl)-1-(1-methyl-1H-pyrazol-4yl-methyl)-4-fluoro-1H-indole-3-carboxamide (Isomer-I);
cis-N-(3-Fluoropiperidin-4-yl)-1-(1-methyl-1H-pyrazol-4yl-methyl)-4,7-difluoro-1H-indole-3-carboxamide (Isomer-I);
cis-N-(3-Fluoropiperidin-4-yl)-1-(2-fluoropyridin-4-ylmethyl)-4-fluoro-1H-indole-3-carboxamide (Isomer-I);
cis-N-(3-Fluoropiperidin-4-yl)-1-(benzothiazol-6-ylmethyl)-4-fluoro-1H-indole-3-carboxamide (Isomer-I);
cis-N-(3-Fluoropiperidin-4-yl)-1-(1-methyl-1H-indazole-3-ylmethyl)-4-fluoro-1H-indole-3-carboxamide (Isomer-I); and
cis-N-(3-Fluoropiperidin-4-yl)-1-(2-fluoropyridin-4-ylmethyl)-4,7-difluoro-1H-indole-3-carboxamide (Isomer-I);
or their pharmaceutically acceptable salt thereof.

In yet another embodiment the representative compounds of pharmaceutically acceptable salt of the present invention includes but not limited to,
cis-N-(3-Fluoropiperidin-4-yl)-1-(2-fluoropyridin-4-ylmethyl)-4,7-difluoro-1H-indole-3-carboxamide hydrochloride (Isomer-I);
cis-N-(3-Fluoropiperidin-4-yl)-1-(2-fluoropyridin-4-ylmethyl)-4,7-difluoro-1H-indole-3-carboxamide hydrochloride (Isomer-II);
trans-N-(3-Fluoropiperidin-4-yl)-1-(2-fluoropyridin-4-ylmethyl)-4,7-difluoro-1H-indole-3-carboxamide hydrochloride (Isomer-I);
trans-N-(3-Fluoropiperidin-4-yl)-1-(2-fluoropyridin-4-ylmethyl)-4,7-difluoro-1H-indole-3-carboxamide hydrochloride (Isomer-II);
cis-N-(3-Fluoropiperidin-4-yl)-1-(5-fluoropyridin-4-ylmethyl)-4,7-difluoro-1H-indole-3-carboxamide hydrochloride (Isomer-I);
cis-N-(3-Fluoropiperidin-4-yl)-1-(2-chloropyridin-4-ylmethyl)-4-fluoro-1H-indole-3-carboxamide hydrochloride (Isomer-I);
cis-N-(3-Fluoropiperidin-4-yl)-1-(2-chloropyridin-4-ylmethyl)-4,7-difluoro-1H-indole-3-carboxamide hydrochloride (Racemate);
cis-N-(3-Fluoropiperidin-4-yl)-1-(2-chloropyridin-4-ylmethyl)-4,7-difluoro-1H-indole-3-carboxamide hydrochloride (Isomer-I);
cis-N-(3-Fluoropiperidin-4-yl)-1-(4-fluorobenzyl)-4-fluoro-1H-indole-3-carboxamide hydrochloride (Isomer-I);
cis-N-(3-Fluoropiperidin-4-yl)-1-(4-fluorobenzyl)-4,7-difluoro-1H-indole-3-carboxamide hydrochloride (Isomer-I);
cis-N-(3-Fluoropiperidin-4-yl)-1-(4-fluorobenzyl)-4,7-difluoro-1H-indole-3-carboxamide hydrochloride (Isomer-II);
cis-N-(3-Fluoropiperidin-4-yl)-1-(2-fluorobenzyl)-4-fluoro-1H-indole-3-carboxamide hydrochloride (Isomer-I);
cis-N-(3-Fluoropiperidin-4-yl)-1-(4-chlorobenzyl)-4-fluoro-1H-indole-3-carboxamide hydrochloride (Isomer-I);
cis-N-(3-Fluoropiperidin-4-yl)-4-fluoro-1-(3-methoxybenzyl)-1H-indole-3-carboxamide hydrochloride (Isomer-I);
cis-N-(3-Fluoropiperidin-4-yl)-4-fluoro-1-(3-methoxybenzyl)-1H-indole-3-carboxamide hydrochloride (Isomer-II);
cis-N-(3-Fluoropiperidin-4-yl)-1-(4-methoxybenzyl)-4-fluoro-1H-indole-3-carboxamide hydrochloride (Isomer-II);
cis-N-(3-Fluoropiperidin-4-yl)-1-(4-methoxybenzyl)-4-fluoro-1H-indole-3-carboxamide hydrochloride (Isomer-I);
cis-N-(3-Fluoropiperidin-4-yl)-1-(4-methoxybenzyl)-4,7-difluoro-1H-indole-3-carboxamide hydrochloride (Isomer-I);
cis-N-(3-Fluoropiperidin-4-yl)-1-(4-methoxybenzyl)-4,7-difluoro-1H-indole-3-carboxyamide hydrochloride (Isomer-II);
cis-N-(3-Fluoropiperidin-4-yl)-1-(3,4-difluorobenzyl)-4-fluoro-1H-indole-3-carboxamide hydrochloride (Isomer-I);
cis-N-(3-Fluoropiperidin-4-yl)-1-(1-methyl-1H-pyrazol-4-yl-methyl)-4-fluoro-1H-indole-3-carboxamide hydrochloride (Isomer-I);
cis-N-(3-Fluoropiperidin-4-yl)-1-(1-methyl-1H-pyrazol-4-yl-methyl)-4,7-difluoro-1H-indole-3-carboxamide hydrochloride (Isomer-I);

cis-N-(3-Fluoropiperidin-4-yl)-1-(2-fluoropyridin-4-ylm-ethyl)-4-fluoro-1H-indole-3-carboxamide hydrochloride (Isomer-I);
cis-N-(3-Fluoropiperidin-4-yl)-1-(benzothiazol-6-ylm-ethyl)-4-fluoro-1H-indole-3-carboxamide hydrochloride (Isomer-I); and
cis-N-(3-Fluoropiperidin-4-yl)-1-(1-methyl-1H-indazole-3-ylmethyl)-4-fluoro-1H-indole-3-carboxamide hydrochloride (Isomer-I).

In another embodiment, the present invention relates to the process for the preparation of the compound of formula (I) or a pharmaceutically acceptable salt thereof. The process for preparation of compound of formula (I) is given in the general schemes-1 and 2 wherein all the groups are as defined above.

General Scheme-1 depicts processes for the preparation of compound of formula (I), wherein $R^1$, $R^2$ and $R^3$ are as defined above.

Step 1: Preparation of Compound of Formula B

The compound of formula A is reacted with trifluoroacetic anhydride in a solvent selected from DMF at RT for 2-4 hours to obtain the compound of formula B.

Step 2: Preparation of Compound of Formula C

The compound of formula B obtained in step 1 is reacted with $R^2CH_2$-halo or $R^2CH_2$—O—$SO_2$—$CH_3$ in presence of potassium carbonate, sodium hydride, cesium carbonate or potassium tert-butoxide in a solvent selected from DMF, THF or acetonitrile overnight at RT to obtain the compound of formula C.

Step 3: Preparation of Compound of Formula D

The compound of formula C obtained in step 2 is reacted with aqueous sodium hydroxide or potassium hydroxide at

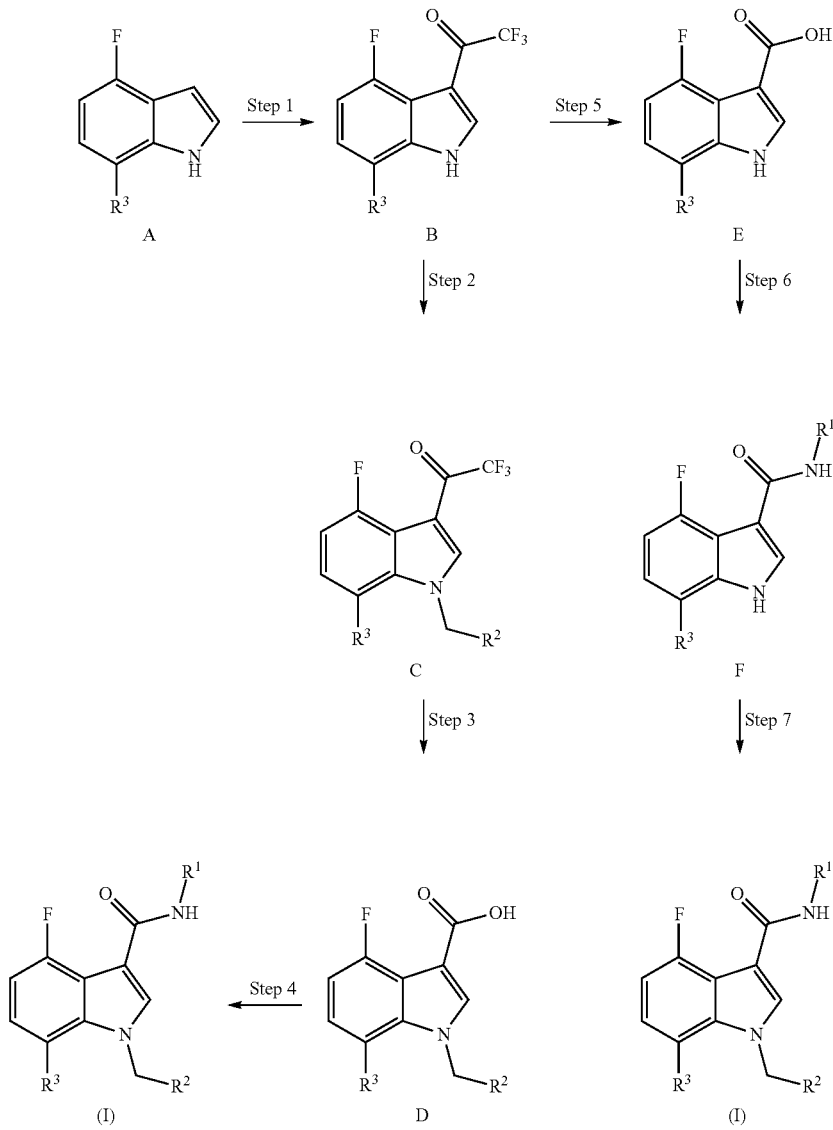

50-70° C. for 16-18 hours to obtain the compound of formula D.

Step 4: Preparation of Compound of Formula (I)

The compound of formula D obtained in step 3 is coupled with amine $R^1$—$NH_2$.HCl in presence of coupling reagent, HATU, DCC, or EDC and a base, DIPEA in a solvent selected from DMF, THF, dichloromethane or 1,4-dioxane at RT overnight to obtain the compound of formula (I).

Step 5:Preparation of Compound of Formula E

The compound of formula B obtained in step 1 is reacted with aqueous sodium hydroxide at 50-70° C. for 16-18 hours to obtain the compound of formula E.

Step 6:Preparation of Compound of Formula F

The compound of formula E obtained in step 5 is coupled with amine $R^1$—$NH_2$.HCl in presence of coupling reagent, HATU, DCC, or EDC and a base, DIPEA in a solvent selected from DMF, THF at RT overnight to obtain the compound of formula F.

Step 7:Preparation of Compound of Formula (I)

The compound of formula F obtained in step 6 is reacted with $R^2CH_2$-halo or $R^2CH_2$—O—$SO_2$—$CH_3$ in presence of potassium carbonate and potassium iodide in a solvent selected from DMF, overnight at RT to obtain the compound of formula (I).

Step 8:Preparation of Compound of Formula (I) (wherein $R^2$ is

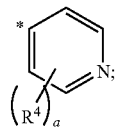

$R^4$ is —S—$CH_3$)

The compound of formula (I) obtained from steps 4 and 7 (wherein $R^2$ is

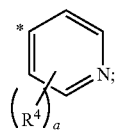

$R^4$ is F) is reacted with sodium thiomethoxide in the solvent selected from DMF or THF at the temperature range of 55-65° C. for 2-5 hours to obtain the compound of formula (I) (wherein $R^2$ is

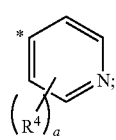

$R^4$ is —S—$CH_3$).

Preparation of Pharmaceutically Acceptable Salt of Compound of Formula (I)

The compound of formula (I) can optionally be converted into its pharmaceutically acceptable salt by reaction with the appropriate acid or acid derivative.

Suitable pharmaceutically acceptable salts will be apparent to those skilled in the art. The salts are formed with inorganic acids e.g. hydrochloric, hydrobromic, sulfuric, nitric & phosphoric acid or organic acids e.g., oxalic, succinic, maleic, acetic, fumaric, citric, malic, tartaric, benzoic, p-toluic, p-toluenesulfonic, benzenesulfonic acid, methanesulfonic or naphthalenesulfonic acid.

Scheme 2 describes the process for the preparation of compound of formula (Ia) and (Ib), wherein $R^2$ and $R^3$ are as defined above.

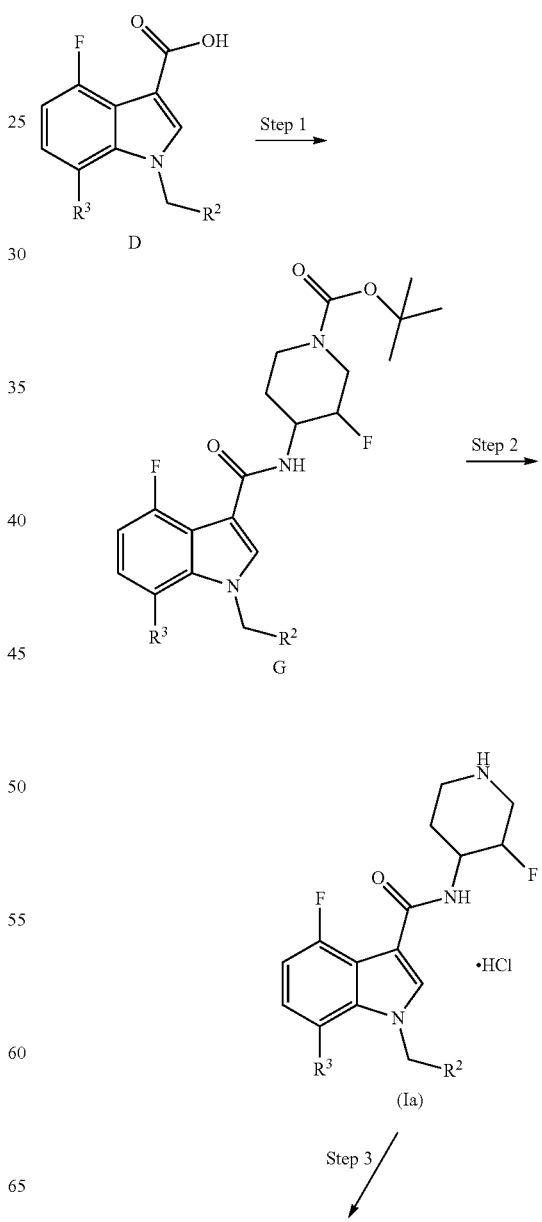

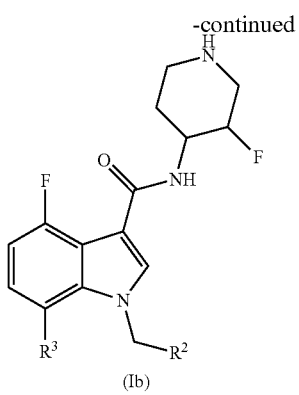
(Ib)

Step 1: Preparation of Compound of Formula G

The compound of formula D (given in scheme 1) is reacted with tert-butyl 4-amino-3-fluoropiperdine-1-carboxylate by following the procedure as described in step 4 of scheme-1 to obtain the compound of formula G.

Step 2: Preparation of Compound of Formula (Ia)

The compound of formula G (obtained in above step) is reacted with ethereal HCl in the solvents selected from DCM and the like at the temperature range of 25-30° C. for 2-4 hours to obtain the compound of formula (Ia).

Step 3: Preparation of Compound of Formula (Ib)

The compound of formula (Ia) (obtained in above step) is subjected to pH adjustment to 7-8 using sodium bicarbonate in water at the temperature range of 5-10° C. to obtain the compound of formula (Ib).

In yet another aspect, the present invention relates to the pharmaceutical composition of the compound of formula (I). In order to use the compound of formula (I), or their stereoisomers and pharmaceutically acceptable salts thereof in therapy, they will normally be formulated into a pharmaceutical composition in accordance with standard pharmaceutical practice.

The pharmaceutical compositions of the present invention may be formulated in a conventional manner using one or more pharmaceutically acceptable excipients. The pharmaceutically acceptable excipient is carrier or diluent. Thus, the active compounds of the invention may be formulated for oral dosing. Such pharmaceutical compositions and processes for preparing same are well known in the art.

The dose of the active compounds can vary depending on factors such as age and weight of patient, nature and severity of the disease to be treated and such other factors. Therefore, any reference regarding pharmacologically effective amount of the compounds of general formula (I), stereoisomers and pharmaceutically acceptable salts thereof refers to the aforementioned factors.

In yet another aspect, the present invention relates to method of treatment of disorders related to muscarinic M1 receptors.

In another embodiment, the disorders related to muscarinic M1 receptors are selected from the group consisting of AD, schizophrenia, cognitive disorders, pain or sleep disorders.

Commercial reagents were used without further purification. RT is defined as an ambient temperature range, typically from 25° C. to 35° C. All mass spectra were obtained using ESI conditions unless otherwise stated. $^1$H-NMR spectra were recorded at 400 MHz on a Bruker instrument. Deuterated chloroform, methanol or dimethyl sulfoxide was used as solvent. Tetramethylsilane (TMS) was used as internal reference standard. Chemical shift values are expressed in parts per million (δ) values. The following abbreviations are used for the multiplicity of the NMR signals: s=singlet, bs=broad singlet, d=doublet, t=triplet, q=quartet, qui=quintet, h=heptet, dd=double doublet, dt=double triplet, tt=triplet of triplets, m=multiplet. Chromatography refers to column chromatography performed using 100-200 mesh silica gel and executed under nitrogen pressure (flash chromatography) conditions.

The stereoisomers as a rule are generally obtained as racemates that can be separated into the optically active isomers in a manner known per se. In the case of the compounds of formula (I) having an asymmetric carbon atom the present invention relates to the D-form, the L-form and D, L—mixtures and in the case of compound of formula (I) containing a number of asymmetric carbon atoms, the diastereomeric forms and the invention extends to each of these stereoisomeric forms and to mixtures thereof including racemates. Those compounds of general formula (I) which have an asymmetric carbon and as a rule are obtained as racemates can be separated one from the other by the usual methods, or any given isomer may be obtained by stereo specific or asymmetric synthesis. However, it is also possible to employ an optically active compound from the start, a correspondingly optically active enantiomeric or diastereomeric compound then being obtained as the final compound.

The stereoisomers of compounds of general formula (I) may be prepared by one or more ways presented below:

i) One or more of the reagents may be used in their optically active form.

ii) Optically pure catalyst or chiral ligands along with metal catalyst may be employed in the reduction process. The metal catalyst may be Rhodium, Ruthenium, Indium and the like. The chiral ligands may preferably be chiral phosphines. (Principles of Asymmetric synthesis, J. E. Baldwin Ed., Tetrahedron series, 14, 311-316).

iii) The mixture of stereoisomers may be resolved by conventional methods such as forming diastereomeric salts with chiral acids or chiral amines or chiral amino alcohols, chiral amino acids. The resulting mixture of diastereomers may then be separated by methods such as fractional crystallization, chromatography and the like, which is followed by an additional step of isolating the optically active product by hydrolyzing the derivative.

iv) The mixture of stereoisomers may be resolved by conventional methods such as microbial resolution, resolving the diastereomeric salts formed with chiral acids or chiral bases.

Chiral acids that can be employed may be tartaric acid, mandelic acid, lactic acid, camphorsulfonic acid, amino acids and the like. Chiral bases that can be employed may be cinchona alkaloids, brucine or a basic amino acid such as lysine, arginine and the like. In the case of the compounds of general formula (I) containing geometric isomerism the present invention relates to all of these geometric isomers.

Chiral HPLC Methods

Method A:

Column: CHIRALPAK AD-H (250×4.6) mm 5 μm; Solvent A=50.0% MeOH, B=49.9% ACN, C=0.1% DEA; Isocratic Flow=1.5 mL/min T=25° C.

Method B:
Column: CHIRALPAK AD-H (250×4.6) mm 5 μm; Solvent A=99.9% MeOH, B=0.1% DEA; Isocratic Flow=0.8 mL/min T=25° C.

The following abbreviations are used herein:
ACN: Acetonitrile
$CCl_4$: Carbon tetrachloride
$CDCl_3$: Deuterated chloroform
DCM: Dichloromethane
DCC: N,N'-Dicyclohexylcarbodiimide
DEA: Diethylamine
DIPEA: N,N-Diisopropylethylamine
DMF: N,N-Dimethylformamide
DMSO: Dimethyl sulfoxide
EDC: Ethylene dichloride
HATU: 2-(7-Aza-1H-benzotriazole-1-yl)-1,1,3,3-tetramethyluronium hexafluorophosphate
HCl: Hydrochloric acid
$K_2CO_3$: Potassium carbonate
MeOH: Methanol
$NaBH_4$: Sodium borohydride
NaOH: Sodium hydroxide
$Na_2SO_4$: Sodium sulphate
RT Room temperature (25-30° C.)
THF: Tetrahydrofuran

EXAMPLES

The compounds of the present invention were prepared according to the following experimental procedures, using appropriate materials and conditions. The following examples are provided by way of illustration only but not to limit the scope of present invention.

Preparation 1:
4-Chloromethyl-1-methyl-1H-pyrazole hydrochloride (I-1)

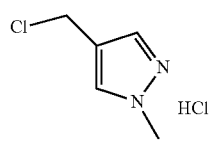

Step-1: To a solution of 1H-pyrazole-4-carboxylic acid ethyl ester (35.0 g, 0.25 mole) in THF (100 mL) was added suspension of sodium hydride (17.38 g, 0.43 mole) in THF (100 mL) solution under $N_2$ at 25° C. and stirred for one hour. Methyl iodide (24 mL, 0.38 mole) was added at RT and the reaction mixture was heated to 60-65° C. for 6 hours. Reaction mixture was quenched in to ice water (200 mL) and extracted with ethyl acetate (100 mL×3). The combined organic phase was washed with water (50 mL), brine solution (50 mL), dried over $Na_2SO_4$ and concentrated under vacuum to obtain ethyl 1-methyl-1H-pyrazole-4-carboxylate.

Yield: 32.36 g (83%); $^1$H-NMR ($CDCl_3$, 400 MHz) δ ppm: 1.30-1.33 (s, 3H), 3.91 (s, 3H), 4.25-4.30 (q, 2H), 7.83 (s, 1H), 7.88 (s, 1H); Mass (m/z): 155.0 (M+H)$^+$.

Step-2: Lithium aluminium hydride (320 mL, 0.32 mole, 1M in THF) was added to a cooled solution of ethyl 1-methyl-1H-pyrazole-4-carboxylate (32.34 g, 0.21 mole) in THF (300 mL) under stirring in $N_2$ atmosphere. The reaction mixture was warmed to RT and stirred further for 3 hours. The reaction mixture was cooled to 0° C., diluted with ethyl acetate and treated with water (25 mL). The mixture was filtered through celite bed and concentrated under vacuum to obtain the crude compound which was further purified by flash chromatography (ethyl acetate:methanol (98:2)) to afford (1-methyl-1H-pyrazol-4-yl)-methanol.

Yield: 14.66 g (62%); $^1$H-NMR ($CDCl_3$, 400 MHz) δ ppm: 1.98 (bs, 1H), 3.88 (s, 3H), 4.56 (s, 2H), 7.36 (s, 1H), 7.45 (s, 1H); Mass (m/z): 113.1 (M+H)$^+$.

Step-3: To a cooled solution of (1-methyl-1H-pyrazol-4-yl)-methanol (8.61 g, 0.076 mole) in DCM (100 mL) under $N_2$ atmosphere, thionyl chloride (8.7 mL, 0.12 mole) was added drop wise. The reaction mixture was warmed to RT and stirred for 2 hours. The reaction mixture was concentrated under vacuum at 23-25° C. to obtain the title compound.

Yield: 12.77 g (99%); $^1$H-NMR (DMSO-$d_6$, 400 MHz) δ ppm: 3.85 (s, 3H), 4.67 (s, 2H), 4.76-4.79 (t, 1H), 4.88 (bs, 1H), 7.47 (s, 1H), 7.78 (s, 1H).

Preparation 2: 4-Bromomethyl-2-fluoropyridine (I-2)

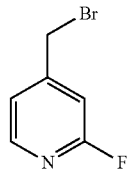

To a solution of 2-fluoro-4-methylpyridine (75.0 g, 0.675 mole) in $CCl_4$ (200 mL) under $N_2$ atmosphere at 25° C. was added N-bromosuccinimide (160 g, 0.90 mole) and benzoyl peroxide (24.52 g, 0.101 mole). The reaction mass was gradually heated to 85° C. and stirred for 5 hours at this temperature. The reaction mass after cooling to RT was filtered under vacuum and washed with $CCl_4$ (50 mL). The filtrate was concentrated under vacuum to obtain the crude residue, which was purified by flash chromatography using ethyl acetate:n-hexane (02:98) to afford the title compound.

Yield: 35.2 g (27%); $^1$H-NMR ($CDCl_3$, 400 MHz) δ ppm: 4.71 (s, 2H), 7.27 (s, 1H), 7.42-7.43 (d, J=4.9 Hz, 1H), 8.24-8.25 (d, J=5.1 Hz, 1H); Mass (m/z): 190.0 (M+H)$^+$, 192.1 (M+H)$^+$.

Preparation 3: 4-Bromomethyl-2,5-difluoropyridine (I-3)

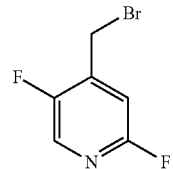

Step-1: To a 0° C. cooled solution of 2,5-difluoroisonicotinic acid (0.5 g, 0.003 mole) in THF (5 mL) under $N_2$, was added lithium aluminum hydride (1 M in THF, 3.7 mL, 0.0037 mole) drop wise. The reaction mixture was warmed to RT and stirred further for 1.5 hours. The reaction mixture was cooled to 0° C., diluted with ethyl acetate and treated with water (0.5 mL). The mixture was filtered through celite bed and concentrated under vacuum to obtain (2,5-difluoropyridin-4-yl)-methanol.

Yield: 0.45 g (98%); $^1$H-NMR (CDCl$_3$, 400 MHz) δ ppm: 4.60 (s, 2H), 4.96 (bs, 1H), 7.05 (s, 1H), 7.78 (s, 1H); Mass (m/z): 145.9 (M+H)$^+$.

Step-2: To a 0° C. cooled solution of (2,5-difluoropyridin-4-yl)-methanol (0.45 g, 0.003 mole) in DCM (10 mL) under N$_2$, was added phosphorus tribromide (0.44 mL, 0.0037 mole) drop wise. The reaction mixture was warmed to RT and stirred for 1.5 hours. The reaction mixture was diluted with DCM (75 mL), treated with saturated aqueous sodium bicarbonate (20 mL) and partitioned. Organic layer was washed with water (20 mL), brine solution (20 mL) and dried over Na$_2$SO$_4$. The organic phase was concentrated under vacuum to obtain the title compound.

Yield: 0.23 g (37%); $^1$H-NMR (DMSO-d$_6$, 400 MHz) δ ppm: 4.68 (s, 2H), 7.20 (s, 1H), 8.16 (s, 1H); Mass (m/z): 208.1 (M+H)$^+$, 210.1 (M+H)$^+$.

Preparation 4: 4-Bromomethyl-2-chloropyridine (I-4)

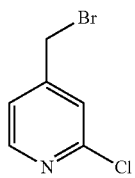

Step-1: To a solution of 2-chloroisonicotinic acid (2.0 g, 0.012 mole) in DMF (5 mL) under N$_2$ at 25° C., was added sodium hydride (0.73 g, 0.015 mole) and stirred for 0.5 hour. Methyl iodide (1.5 mL, 0.025 mole) was added at RT and the reaction mixture was warmed to 50° C. for 2 hours. The reaction mixture was dissolved in ice water (50 mL) and extracted with ethyl acetate (50 mL×3). Organic layer was washed with brine solution (50 mL) and dried over Na$_2$SO$_4$. The organic phase was concentrated under vacuum to obtain methyl 2-chloroisonicotinate.

Yield: 2.1 g (100%); Mass (m/z): 172.0 (M+H)$^+$, 174.0 (M+H)$^+$.

Step-2: To a cooled solution of methyl 2-chloroisonicotinate (1.7 g, 0.009 mole) in THF (30 mL) under N$_2$, was added lithium borohydride (0.43 g, 0.019 mole) in portions. The reaction mixture was warmed to RT and stirred further for 3 hours. The reaction mixture was concentrated under reduced pressure; residue was dissolved in ice cold water (50 mL) and extracted with ethyl acetate (50 mL×3). Organic layer was washed with brine solution (50 mL) and dried over Na$_2$SO$_4$. The organic phase was concentrated under vacuum to obtain the crude compound which was further purified by flash chromatography using ethyl acetate: n-hexane (40:60) to afford (2-chloropyridin-4-yl)-methanol.

Yield: 1.0 g (71%); $^1$H-NMR (CDCl$_3$, 400MHz) δ ppm: 2.29 (bs, 1H), 4.75 (s, 2H), 7.20-7.21 (d, J=4.9 Hz, 1H), 7.31 (s, 1H), 8.32-8.33 (d, J=5.0 Hz, 1H); Mass (m/z): 144.0 (M+H)$^+$, 145.9 (M+H)$^+$.

Step-3: (2-Chloropyridin-4-yl)-methanol was converted to the title compound using similar procedure as described in step-2 of preparation 3.

Yield: 0.49 g (85%); $^1$H-NMR (CDCl$_3$, 400 MHz) δ ppm: 4.35 (s, 2H), 7.36 (s, 1H), 8.37-8.38 (d, J=4.9 Hz, 1H); Mass (m/z): 205.9 (M+H)$^+$, 208.0 (M+H)$^+$.

Preparation 5: 4-Chloromethyl-3-fluoropyridine (I-5)

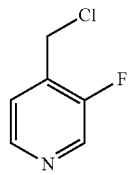

Step-1: 3-Fluoroisonicotinic acid was converted to (3-fluoropyridin-4-yl)-methanol similar to a procedure described in step-1 of preparation 3.

Yield: 0.19 g (70%); Mass (m/z): 128.1 (M+H)$^+$.

Step-2: To a cooled solution of (3-fluoropyridin-4-yl)-methanol (0.19 g, 0.001 mole) in DCM (5 mL) under N$_2$, thionyl chloride (0.21 mL, 0.003 mole) was added drop wise. The reaction mixture was warmed to RT and stirred for 2 hours. The reaction mixture was diluted with DCM (50 mL), and treated with saturated aqueous sodium bicarbonate (10 mL). Organic layer was washed with water (20 mL), brine solution (20 mL) and dried over Na$_2$SO$_4$ and concentrated under vacuum to obtain the title compound.

Yield: 0.12 g (56%); Mass (m/z): 146.0 (M+H)$^+$, 148.0 (M+H)$^+$.

Preparation 6: 1-Chloromethyl-2-fluorobenzene (I-6)

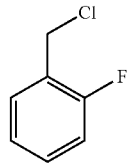

The title compound, 1-chloromethyl-2-fluorobenzene was synthesized from 2-fluorobenzoic acid following the procedure as described in preparation 5.

Yield: 0.455 g (100%); Mass (m/z): 145 (M+H)$^+$, 147.0 (M+H)$^+$.

Preparation 7: Methanesulfonic acid 2,3-difluoro-pyridin-4-ylmethyl ester (I-7)

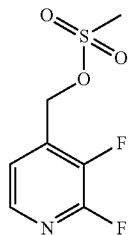

Step-1: (2,3-Difluoropyridin-4-yl)-methanol was synthesized from 2,3-difluoroisonicotinic acid by following the procedure as described in preparation 3.

Yield: 0.16 g (29%); Mass (m/z): 146.0 (M+H)$^+$.

Step-2: (2,3-Difluoropyridin-4-yl)-methanol was converted to the title compound by reacting with methanesulfonyl chloride and the product was used as such without any purification.

Yield: 0.37 g (68%).

Preparation 8: 1-Chloromethyl-3-methoxybenzene
(I-8)

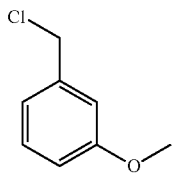

Step-1: To the solution of 3-hydroxybenzaldehyde (3.0 g, 0.025 mole) in DMF (15 mL) was added $K_2CO_3$ (10.18 g, 0.073 mole) and methyl iodide (6.93 g, 0.049 mole) at RT and stirred for 12 hours under nitrogen atmosphere. Reaction mixture was quenched in to water (50 mL) and extracted with ethyl acetate (50 mL×3). The organic layer was dried over $Na_2SO_4$ and concentrated under vacuum to get 3-methoxybenzaldehyde.

Yield: 3.11 g (93%); $^1$H-NMR (CDCl$_3$, 400 MHz) δ ppm: 3.87 (s, 3H), 7.17-7.20 (m, 1H), 7.40-7.41 (m, 1H), 7.43-7.46 (m, 2H), 9.98 (s, 1H).

Step-2: To a solution of 3-methoxybenzaldehyde (3.11 g, 0.022 mole) in THF (10 mL) and methanol (20 mL), NaBH$_4$ (1.43 g, 0.042 mole) was added portion wise at 0-10° C. under nitrogen atmosphere. After addition, reaction mixture was stirred at RT for 12 hours. Reaction mixture was concentrated under vacuum and quenched in to water (50 mL). Aqueous layer was extracted with ethyl acetate (50 mL×3). The organic layer was dried over Na$_2$SO$_4$ and concentrated under vacuum to get (3-methoxy-phenyl)-methanol.

Yield: 2.95 g (93%); $^1$H-NMR (CDCl$_3$, 400 MHz) δ ppm: 3.85 (s, 3H), 4.69-4.71 (m, 2H), 6.85-6.88 (m, 1H), 6.96-6.97 (m, 2H), 7.28-7.32 (m, 1H).

Step-3: The title compound was synthesized from (3-methoxyphenyl)-methanol by the procedure described in preparation 5.

Yield: 3.03 g (78%); $^1$H-NMR (CDCl$_3$, 400 MHz) δ ppm: 3.82 (s, 3H), 4.57 (s, 2H), 6.85-6.88 (m, 1H), 6.94-6.98 (m, 2H), 7.26-7.30 (m, 1H).

Preparation 9: tert-Butyl
4-amino-3-fluoropiperidine-1-carboxylate

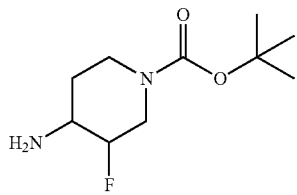

Step 1: tert-Butyl 4-trimethylsilanyloxy-3,6-dihydro-2H-pyridine-1-carboxylate

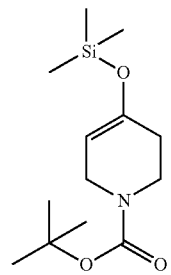

Chlorotrimethylsilane (16.3 g, 0.15 mole) was added drop wise to a mixture of tert-butyl 4-oxo-piperidine-1-carboxylate (25.0 g, 0.12 mole), triethylamine (42.6 mL, 0.31 mole) in 35 mL of DMF at 25° C. in 20 minutes under N$_2$. The reaction mass was heated to 90-92° C. and maintained for 20 hours. Reaction mass was allowed to cool to 25° C. n-Hexane (120 mL) was added to the reaction mass and neutralized with saturated sodium bicarbonate solution (60 mL). Organic layer was separated, washed with saturated sodium bicarbonate solution, water and brine solution. The organic layer was dried over Na$_2$SO$_4$ and concentrated under vacuum at 45° C. to obtain the title compound. Yield: 33.3 g (66%)

Step 2:
tert-butyl-3-fluoro-4-oxo-piperidine-1-carboxylate

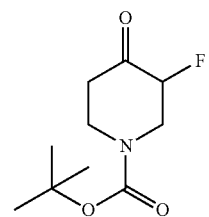

tert-Butyl 4-trimethylsilanyloxy-3,6-dihydro-2H-pyridine-1-carboxylate (33.3 g, 0.12 mole) was added drop wise to Selectfluor® (30.6 g, 0.086 mole) in 250 mL of acetonitrile at RT in 15 minutes. The reaction was exothermic and the reaction mass temperature was raised to 60° C. and clear a solution was obtained. After addition, the reaction mass was stirred at RT for 10 hours under N$_2$. The reaction mass was diluted with 200 mL of ethyl acetate and washed with brine solution (100 mL×2). Organic layer was dried over Na$_2$SO$_4$ and concentrated on rota vac at 45° C. under vacuum to obtain residue, which was purified by flash chromatography using ethyl acetate:hexane (40:60) to afford the title compound.

Yield: 15.2 g (55%);

Step 3: tert-Butyl-4-(benzylamino)-3-fluoropiperidine-1-carboxylate

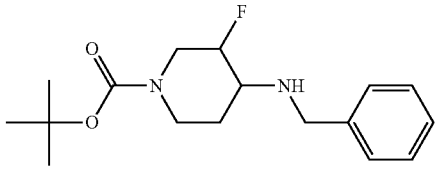 [SMILES: CC(C)(C)OC(=O)N1CCC(NCc2ccccc2)C(F)C1]

To a clear solution of tert-butyl 3-fluoro-4-oxo-piperidine-1-carboxylate (3.0 g, 0.0138 mole, obtained from step 2) in EDC (50 mL), benzyl amine (1.77 g, 0.016 mole) was added and stirred for 2 hours. Sodium triacetoxyborohydride (5.86 g, 0.276 mole) was added at 10° C. After addition, reaction mass was stirred for 12 hours under $N_2$ at RT. The reaction mass was quenched into water, basified with lye solution and extracted with ethyl acetate (50 mL×3). The organic layer was dried over $Na_2SO_4$ and concentrated under vacuum to obtain the crude residue, which was purified by flash chromatography using ethyl acetate:hexane (20:80) to afford tert-butyl 4-(benzylamino)-3-fluoropiperidine-1-carboxylate as cis- and trans-diastereomers separately.

Trans-diastereomer (3a):

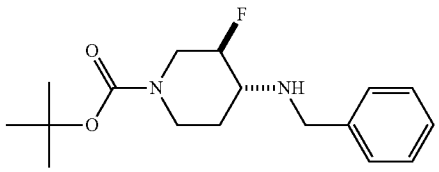 [SMILES: CC(C)(C)OC(=O)N1CC[C@@H](NCc2ccccc2)[C@H](F)C1]

Yield: 0.370 g (8.8%);
$^1$H-NMR (CDCl$_3$, 400 MHz) δ ppm: 1.45 (s, 9H), 1.60-1.70 (m, 2H), 1.96-1.99 (m, 1H), 2.79-2.91 (m, 3H), 3.78-3.81 (m, 1H), 3.88-3.91 (m, 2H), 4.22-4.27 (m, 1H), 4.36-4.39 (m, 1H), 7.24-7.35 (m, 5H); Mass (m/z): 309.2 (M+H)$^+$.

Cis-diastereomer (3b):

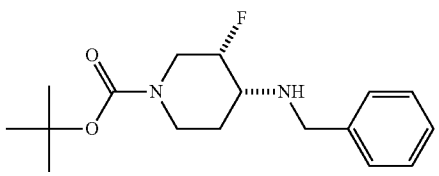 [SMILES: CC(C)(C)OC(=O)N1CC[C@@H](NCc2ccccc2)[C@@H](F)C1]

Yield: 2.02 g (47%);
$^1$H-NMR (DMSO-d$_6$, 400 MHz) δ ppm: 1.38 (s, 9H), 1.44-1.68 (m, 2H), 2.05 (m, 1H), 2.57-2.66 (m, 2H), 2.93-3.02 (m, 1H), 3.76-3.77 (m, 2H), 3.90 (m, 1H), 4.12 (m, 1H), 4.71-4.83 (m, 1H), 7.19-7.35 (m, 5H); Mass (m/z): 309.2 (M+H)$^+$.

Trans-diastereomer (3a) obtained from step-3 was subjected to chiral separation using chiral HPLC 'Method A' to afford two enantiomers. trans-Enantiomer-I eluting at retention time 6.86 minutes and trans-Enantiomer-II eluting at retention time 11.96 minutes.

Similarly the cis diastereomer (3b), obtained from step-3 was subjected to chiral separation using chiral HPLC 'Method B' to afford two enantiomers. cis-Enantiomer-I eluting at retention time 5.76 minutes and cis-Enantiomer-II eluting at retention time 6.98 minutes.

Step-4: cis-tert-Butyl 4-amino-3-fluoropiperidine-1-carboxylate (cis-Isomer-I) (I-9a)

To a solution of cis-Enantiomer-I (as obtained in step-3, 2.0 g, 0.06 mole, obtained in above step) in methanol (50 mL), 10% Pd/C (1.0 g, 0.5 v) was added in one portion and stirred for 2 hours under $H_2$ gas bubbling. Reaction mixture was filtered through celite and filtrate was concentrated under vacuum to obtain cis-tert-butyl 4-amino-3-fluoropiperidine-1-carboxylate (cis-Isomer-I).

Yield: 1.2 g (85%); $^1$H-NMR (DMSO-d$_6$, 400 MHz) δ ppm: 1.38 (s, 9H), 1.50-1.54 (m, 2H), 1.69-1.70 (m, 2H); 2.76-2.80 (m, 2H), 3.00 (m, 1H), 3.85 (m, 1H), 4.07 (m, 1H), 4.45-4.63 (m, 1H); Mass (m/z): 219.1 (M+H)$^+$.

Step-5: cis-tert-Butyl 4-amino-3-fluoropiperidine-1-carboxylate (cis-Isomer-II) (I-9b)

Cis-Enantiomer-II (obtained from step 3) was debenzylated by following the above procedure described in step 4 to obtain cis-tert butyl 4-amino-3-fluoropiperidine-1-carboxylate (cis-Isomer II).

Yield: 1.1 g (83.5%); $^1$H-NMR (DMSO-d$_6$, 400 MHz) δ ppm: 1.38 (s, 9H), 1.42-1.54 (m, 2H), 1.82 (m, 2H), 2.71-2.81 (m, 2H), 2.99 (m, 1H), 3.85 (m, 1H), 4.08 (m, 1H), 4.46-4.58 (m, 1H); Mass (m/z): 219.1 (M+H)$^+$.

Step-6: trans-tert-Butyl 4-amino-3-fluoropiperidine-1-carboxylate (trans-Isomer-I) (I-9c)

trans-Enantiomer-I (obtained from step-3) was debenzylated by following the above procedure described in step 4 to obtain trans-tert-butyl 4-amino-3-fluoropiperidine-1-carboxylate (trans-Isomer-I).

Yield: 0.33 g (96%);'H-NMR (CDCl$_3$, 400 MHz) δ ppm: 1.45 (s, 9H), 1.55-1.57 (m, 2H), 1.86-1.89 (m, 2H), 2.70-2.78 (m, 2H), 2.89-2.91 (m, 1H), 4.01-4.05 (m, 1H), 4.13-4.14 (m, 1H), 4.20-4.28 (m, 1H); Mass (m/z): 219.1 (M+H)$^+$.

Step-7: trans-tert-Butyl 4-amino-3-fluoropiperidine-1-carboxylate (trans-Isomer-II) (I-9d)

trans-Enantiomer-II (obtained from step-3) was debenzylated by following the above procedure described in step 4 to obtain trans-tert-butyl 4-amino-3-fluoropiperidine-1-carboxylate (trans-Isomer-II).

Yield: 0.31 g (95%); $^1$H-NMR (CDCl$_3$, 400 MHz) δ ppm: 1.45 (s, 9H), 1.52-1.57 (m, 2H), 1.86-1.89 (m, 2H), 2.75-2.80 (m, 2H), 2.86-2.94 (m, 1H), 3.98-4.04 (m, 1H), 4.11-4.16 (m, 1H), 4.20-4.28 (m, 1H); Mass (m/z): 219.1 (M+H)$^+$.

Preparation 10: 2, 2, 2-Trifluoro-1-(4-fluoro-1H-indol-3-yl)-ethanone (I-10)

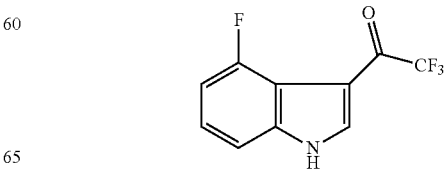

To a solution of 4-fluoroindole (28.75 g, 0.213 mole (prepared as per *Org. Synth.* 1985, 63, 214) in DMF (200 mL), trifluoroacetic anhydride (73.50 g, 0.349 mole) was added slowly drop wise at 0° C., under nitrogen atmosphere. After completion of addition, the reaction mixture was stirred at RT for 2 hours. Reaction mixture was cooled to 0-10° C. and quenched slowly in to ice cold water (500 mL). Reaction mass was stirred for 30 minutes. The solid thus obtained were filtered, washed with water (500 mL) followed by n-hexane (500 mL).The resulting solids were dried under vacuum to afford the title compound.

Yield: 37.25 g (75%); $^1$H-NMR (DMSO-d$_6$, 400MHz) δ ppm: 7.03-7.07 (m, 1H), 7.30-7.35 (m, 1H), 7.39-7.41 (m, 1H), 8.51 (s, 1H), 12.91 (s, 1H); Mass (m/z): 230 (M−H)$^+$.
Preparation of Examples of compound of formula (I)

Example 1

N-[(1S,2S)-2-Hydroxycyclohexyl]-1-(1-methyl-1H-pyrazol-4-ylmethyl)-4-fluoro-1H-indole-3-carboxamide

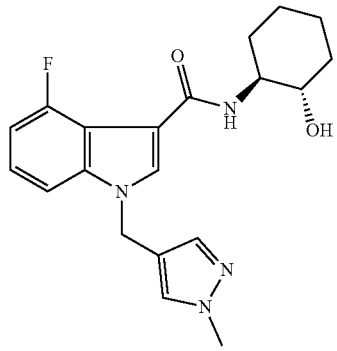 [SMILES: Cn1cc(Cn2cc(C(=O)N[C@H]3CCCC[C@@H]3O)c3c(F)cccc32)cn1]

Step-1: 1-[1-(1-Methyl-1H-pyrazol-4-ylmethyl)-4-fluoro-1H-indol-3-yl]-2,2,2-trifluoroethanone

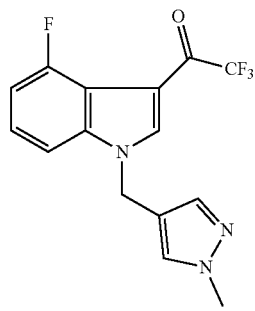 [SMILES: Cn1cc(Cn2cc(C(=O)C(F)(F)F)c3c(F)cccc32)cn1]

To a cooled solution of the 2,2,2-trifluoro-1-(4-fluoro-1H-indol-3-yl)-ethanone (I-10, 13.30 g, 0.057 mole) in DMF (100 mL) under N$_2$ was added K$_2$CO$_3$ (47.06 g, 0.34 mole), 4-chloromethyl-1-methyl-1H-pyrazole hydrochloride (13.07 g, 0.078 mole) and the contents were stirred overnight at RT. Reaction mixture was quenched in to ice cold water (1000 mL) and extracted with ethyl acetate (250 mL×3). The combined organic layers were washed with water (200 mL×3), brine solution (100 mL) and dried over Na$_2$SO$_4$. The organic phase was concentrated under vacuum to obtain a crude compound which was further purified by flash chromatography using (ethyl acetate:n-hexane (80:20)) to afford 1-[1-(1-methyl-1H-pyrazol-4-ylmethyl)-4-fluoro-1H-indole-3-yl]-2,2,2-trifluoroethanone.

Yield: 17.23 g (92%); $^1$H-NMR (CDCl$_3$, 400 MHz) δ ppm: 3.88 (s, 3H), 5.26 (s, 2H), 7.01-7.05 (m, 1H), 7.21-7.26 (m, 1H), 7.30-7.34 (m, 2H), 7.48 (s, 1H), 7.91 (s, 1H); Mass (m/z): 326.2 (M+H)$^+$.

Step-2: 1-(1-Methyl-1H-pyrazol-4-ylmethyl)-4-fluoro-1H-indole-3-carboxylic acid

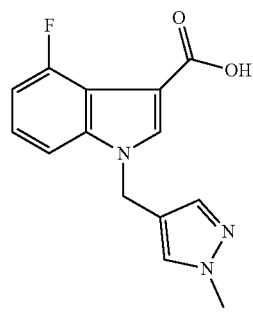 [SMILES: Cn1cc(Cn2cc(C(=O)O)c3c(F)cccc32)cn1]

A mixture of 1-[1-(1-methyl-1H-pyrazol-4-ylmethyl)-4-fluoro-1H-indole-3-yl]-2,2,2-trifluoroethanone (21.39 g, 0.066 mole) and 4N aqueous NaOH (27.07 g, 0.67 mole) was heated to 98-100° C. for 5 hours. Reaction mass was cooled to 5-10° C. and diluted with 100 mL of ice cold water. Aqueous layer was acidified with acetic acid to pH ~5 at 5-10° C. The solids thus obtained were filtered. These solids were extracted from mixture of ethyl acetate:methanol (80:20), dried over Na$_2$SO$_4$ and concentrated under vacuum to obtain 1-(1-methyl-1H-pyrazol-4-ylmethyl)-4-fluoro-1H-indole-3-carboxylic acid.

Yield: 16.71 g (93%); $^1$H-NMR (DMSO-d$_6$, 400 MHz) δ ppm: 3.75 (s, 1H), 5.29 (s, 2H), 6.87-6.92 (m, 1H), 7.17-7.22 (m, 1H), 7.40-7.50 (m, 2H), 7.73 (s, 1H), 8.11 (s, 1H); Mass (m/z): 274.3 (M+H)$^+$.

Step-3: N-[(1S,2S)-2-Hydroxycyclohexyl]-1-(1-methyl-1H-pyrazol-4-ylmethyl)-4-fluoro-1H-indole-3-carboxamide To a solution of 1-(1-methyl-1H-pyrazol-4-ylmethyl)-4-fluoro-1H-indole-3-carboxylic acid (16.70 g, 0.061 mole) in DMF (120 mL) and HATU (29.21 g, 0.077 mole) stirred for 15 minutes followed by addition of (1S,2S) 2-amino cyclohexanol hydrochloride (11.28 g, 0.074 mole) and DIPEA (49 mL, 0.28 mole) in 15 minutes of time interval at RT. During addition of DIPEA reaction mass becomes exothermic. After completion of addition, reaction mixture was stirred overnight at RT. Reaction mass was quenched slowly in to water (800 mL) and stirred for 1 hour. Solid obtained was filtered, washed with water (1000 mL). These solids were extracted from mixture of ethyl acetate:methanol (80:20), dried over Na$_2$SO$_4$ and concentrated under vacuum to obtain solids. These solids were dissolved in ethyl acetate (700 mL), stirred at 60° C. and filtered to remove any undissolved particles. The filtrate was concentrated under vacuum to get the title product.

Yield: 17.64 g (78%); $^1$H-NMR (DMSO-d$_6$, 400 MHz) δ ppm: 1.17-1.24 (m, 4H), 1.59-1.65 (m, 2H), 1.86-1.88 (m, 1H), 1.96-1.98 (m, 1H), 3.59-3.61 (m, 1H), 3.76 (s, 3H), 4.70-4.71 (d, J=4.7 Hz, 1H), 5.28 (s, 2H), 6.90-6.95 (m, 1H), 7.18-7.22 (m, 1H), 7.40-7.45 (m, 2H), 7.50-7.52 (d, J=8.27 Hz, 1H), 7.71 (s, 1H), 8.00 (s, 1H); Mass (m/z): 371.2 (M+H)$^+$, $[\alpha]_D^{25}$=+34.8°.

Example 2

N-[(1S,2S)-2-Hydroxycyclohexyl]-1-(2-chloropyridin-4-ylmethyl)-4-fluoro-1H-indole-3-carboxamide

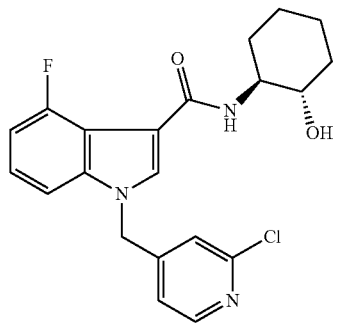 [SMILES: O=C(N[C@H]1CCCC[C@@H]1O)c1cn(Cc2ccnc(Cl)c2)c2cccc(F)c12]

Step-1: 4-Fluoro-1H-indole-3-carboxylic acid

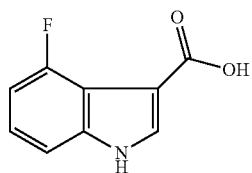 [SMILES: O=C(O)c1c[nH]c2cccc(F)c12]

To 2,2,2-trifluoro-1-(4-fluoro-1H-indol-3-yl)-ethanone (I-10, 18.49 g, 0.080 mole), 4N aqueous NaOH (200 mL, 0.80 mole) was added at RT and heated to 100° C. for 3 hours. Reaction mixture was cooled to RT and diluted with ice-cold water (200 mL). The aqueous layer was washed with ethyl acetate (100 mL×2) and acidified with dilute HCl to pH~4. Solid obtained was filtered, washed with water and n-hexane of each 100 mL separately. The solids were dried under vacuum.

Yield: 5.43 g (38%); $^1$H-NMR (DMSO-d$_6$, 400 MHz) δ ppm: 6.84-6.89 (m, 1H), 7.12-7.17 (m, 1H), 7.26-7.28 (m, 1H), 8.02 (s, 1H), 11.87 (s, 1H), 12.05 (m, 1H); Mass (m/z): 180.2 (M+H)$^+$.

Step-2: N-[(1S,2S)-2-Hydroxycyclohexyl]-4-fluoro-1H-indole-3-carboxamide

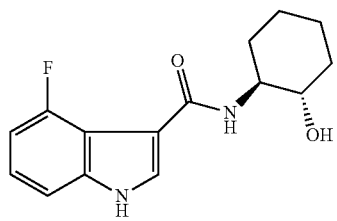 [SMILES: O=C(N[C@H]1CCCC[C@@H]1O)c1c[nH]c2cccc(F)c12]

To a solution of 4-fluoro-1H-indole-3-carboxylic acid obtained in above step (0.39 g, 0.002 mole) in DMF (15 mL) under N$_2$ at 25° C. was added HATU (0.99 g, 0.0026 mole), (1S,2S)-2-aminocyclohexanol hydrochloride (0.39 gm, 0.0026 mole), DIPEA (1.5 mL, 0.0026 mole) with 5 minutes gap of each addition. The reaction mixture was stirred for overnight at RT. The reaction mixture was quenched in to water (50 mL) and extracted with ethyl acetate (25 mL×3). Organic layer was washed with brine solution (20 mL), dried over Na$_2$SO$_4$ and concentrated under vacuum to obtain the crude residue, which was further purified by flash chromatography (methanol:chloroform (03:97)) to afford the title compound.

Yield: 0.43 g (73%); $^1$H-NMR (DMSO-d$_6$, 400 MHz) δ ppm: 1.17-1.25 (m, 4H), 1.60-1.66 (m, 2H), 1.87-1.97 (m, 2H), 3.37-3.39 (m, 1H), 3.59-3.64 (m, 1H), 4.73-4.74 (d, J=4.9 Hz, 1H), 6.87-6.92 (m, 1H), 7.12-7.17 (m, 1H), 7.28-7.30 (d, J=8.1 Hz, 1H), 7.41-7.45 (t, 1H), 7.91-7.92 (d, J=2.4 Hz, 1H), 11.88 (s, 1H); Mass (m/z): 277.1 (M+H)$^+$.

Step 3: N-[(1S,2S)-2-Hydroxycyclohexyl]-1-(2-chloropyridin-4-ylmethyl)-4-fluoro-1H-indole-3-carboxamide To a solution of N-[(1S,2S)-2-hydroxycyclohexyl]-4-fluoro-1H-indole-3-carboxamide (0.24 g, 0.0008 mole) in DMF (5 mL) under N$_2$ at 25° C. was added potassium carbonate (0.37 g, 0.0026 mole), potassium iodide (0.014 g, 0.00008 mole), 4-bromomethyl-2-chloropyridine (I-4, 0.25 g, 0.0012). The reaction mixture was stirred for overnight at RT. The reaction mixture was quenched in to ice water (50 mL) and extracted with ethyl acetate (50 mL×3). Organic layer was washed with brine solution (50 mL) and dried over Na$_2$SO$_4$. The organic phase was concentrated under vacuum to obtain the crude residue, which was further purified by flash chromatography using methanol:chloroform (02:98) to afford the title compound.

Yield: 1.0 g (76%); $^1$H-NMR (CDCl$_3$, 400 MHz) δ ppm: 1.27-1.44 (m, 4H), 1.79 (m, 2H), 2.11 (m, 2H), 3.49 (m, 1H), 3.87 (m, 1H), 4.29 (s, 1H), 5.34 (s, 2H), 6.88 (s, 1H), 6.99-7.02 (m, 3H), 7.21 (m, 2H), 8.02 (s, 1H), 8.33-8.34 (d, J=3.8 Hz, 1H); Mass (m/z): 402.2 (M+H)$^+$.

Examples 3 to 19

The compounds of Examples 3 to 19 were prepared by following the experimental procedures as described in the Examples 1 and 2, with some noncritical variations

| Example No. | Chemical name and Structure | Characterization data |
|---|---|---|
| 3 | 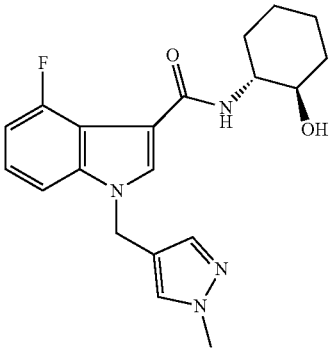<br>N-[(1R,2R)-2-Hydroxycyclohexyl]-1-(1-methyl-1H-pyrazol-4-ylmethyl)-4-fluoro-1H-indole-3-carboxamide | $^1$H - NMR (DMSO-$d_6$, 400 MHz) δ ppm: 1.16-1.29 (m, 4H), 1.59-1.65 (m, 2H), 1.86-1.98 (m, 2H), 3.29-3.34 (m, 1H), 3.56-3.60 (m, 1H), 3.75 (s, 3H), 4.70-4.71 (d, 1H), 5.28 (s, 2H), 6.90-6.95 (m, 1H), 7.17-7.22 (m, 1H), 7.40-7.44 (t, 1H), 7.45 (s, 1H), 7.50-7.52 (d, J = 8.3 Hz, 1H), 7.71 (s, 1H), 8.00 (s, 1H); Mass (m/z): 371.3 (M + H)$^+$. |
| 4 | 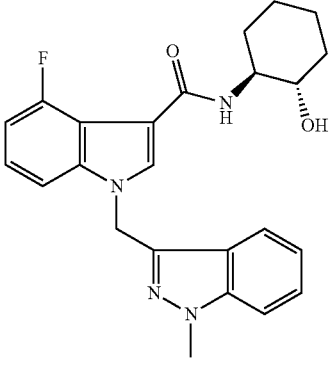<br>N-[(1S,2S)-2-Hydroxycyclohexyl]-1-(1-methyl-1H-indazol-3-ylmethyl)-4,7-difluoro-1H-indole-3-carboxamide | $^1$H - NMR (DMSO-$d_6$, 400 MHz) δ ppm: 1.16-1.23 (m, 4H), 1.59-1.65 (m, 2H), 1.86-1.98 (m, 2H), 3.29-3.34 (m, 1H), 3.56-3.60 (m, 1H), 4.01 (s, 3H), 4.70-4.71 (d, 1H), 5.81 (s, 2H), 6.89-6.95 (m, 1H), 7.09-7.13 (m, 1H), 7.16-7.21 (m, 1H), 7.35-7.39 (t, 1H), 7.43-7.47 (t, 1H), 7.53-7.55 (d, J = 8.2 Hz, 1H), 7.59-7.61 (d, J = 8.5 Hz, 1H), 7.65-7.67 (d, J = 8.1 Hz, 1H), 8.13 (s, 1H); Mass (m/z): 421.3 (M + H)$^+$. |
| 5 | 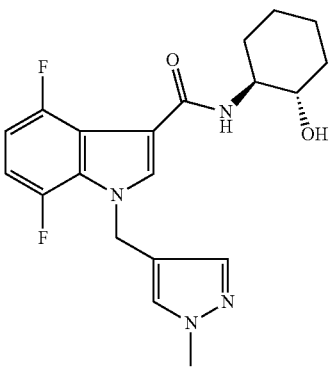<br>N-[(1S,2S)-2-Hydroxycyclohexyl]-1-(1-methyl-1H-pyrazol-4-ylmethyl)-4,7-difluoro-1H-indole-3-carboxamide | $^1$H - NMR (DMSO-$d_6$, 400 MHz) δ ppm: 1.19-1.24 (m, 4H), 1.59-1.62 (m, 2H), 1.85-1.88 (m, 1H), 1.95-1.97 (m, 1H), 3.27-3.29 (m, 1H), 3.57-3.59 (m, 1H), 3.76 (s, 3H), 4.65-4.66 (d, J = 4.75 Hz, 1H), 5.35 (s, 2H), 6.86-6.88 (m, 1H), 7.01-7.03 (m, 1H), 7.40 (s, 1H), 7.48-7.53 (m, 1H), 7.66 (s, 1H), 8.00 (s, 1H); Mass (m/z): 389.3 (M + H)$^+$. |

| Example No. | Chemical name and Structure | Characterization data |
|---|---|---|
| 6 | 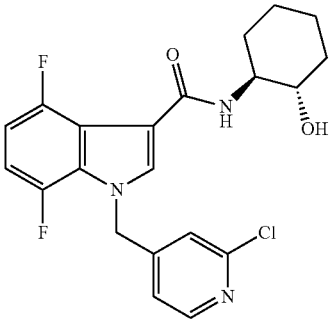<br>N-[(1S,2S)-2-Hydroxycyclohexyl]-1-(2-chloropyridin-4-ylmethyl)-4,7-difluoro-1H-indole-3-carboxamide | $^1$H - NMR (DMSO-d$_6$, 400 MHz) δ ppm: 1.23 (m, 4H), 1.61-1.62 (m, 2H), 1.87-1.97 (m, 2H), 3.40 (m, 1H), 3.60 (m, 1H), 4.66-4.67 (d, 1H), 5.63 (s, 2H), 6.88-6.93 (m, 1H), 6.97-7.04 (m, 2H), 7.22 (s, 1H), 7.66-7.69 (t, 1H), 8.10 (s, 1H), 8.35-8.36 (d, J = 5.0 Hz, 1H); Mass (m/z): 420.3 (M + H)$^+$. |
| 7 | 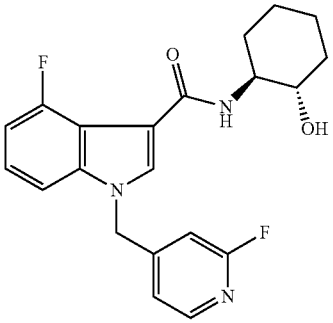<br>N-[(1S,2S)-2-Hydroxycyclohexyl]-1-(2-fluoropyridin-4-yl-methyl)-4-fluoro-1H-indole-3-carboxamide | $^1$H - NMR (DMSO-d$_6$, 400 MHz) δ ppm: 1.17-1.29 (m, 4H), 1.59-1.65 (t, 2H), 1.86-1.98 (dd, 2H), 3.36 (m, 1H), 3.60-3.61 (m, 1H), 4.69-4.70 (d, 1H), 5.61 (s, 2H), 6.92-6.97 (t, 2H), 7.05-7.06 (d, J = 4.7 Hz, 1H), 7.15-7.20 (m, 1H), 7.31-7.33 (d, J = 8.2 Hz, 1H), 7.51-7.55 (t, 1H), 8.11 (s, 1H), 8.16-8.17 (d, J = 5.1 Hz, 1H); Mass (m/z): 386.3 (M + H)+. |
| 8 | 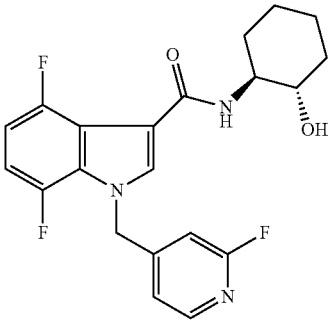<br>N-[(1S,2S)-2-Hydroxycyclohexyl]-1-(2-fluoropyridin-4-ylmethyl)-4,7-difluoro-1H-indole-3-carboxamide | $^1$H - NMR (DMSO-d$_6$, 400 MHz) δ ppm: 1.22-1.29 (m, 4H), 1.60-1.66 (m, 2H), 1.88-1.98 (m, 2H), 3.33-3.38 (m, 1H), 3.61-3.63 (m, 1H), 4.66-4.68 (d, 1H), 5.67 (s, 2H), 6.86-6.93 (m, 2H), 6.96-7.02 (m, 2H), 7.65-7.68 (t, 1H), 8.11 (s, 1H), 8.18-8.20 (d, J = 5.11 Hz, 1H); Mass (m/z): 404.2 (M + H)$^+$. |

| Example No. | Chemical name and Structure | Characterization data |
| --- | --- | --- |
| 9 | 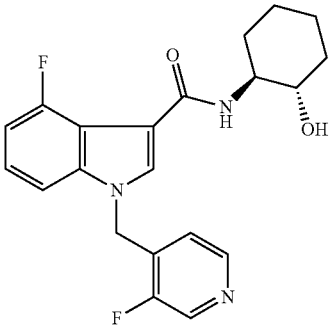<br>N-[(1S,2S)-2-Hydroxycyclohexyl]-1-(3-fluoropyridin-4-ylmethyl)-4-fluoro-1H-indole-3-carboxamide | $^1$H - NMR (DMSO-$d_6$, 400 MHz) δ ppm: 1.18-1.25 (m, 4H), 1.60-1.66 (m, 2H), 1.87-1.89 (m, 1H), 1.97-1.99 (m, 1H), 3.36-3.37 (m, 1H), 3.60-3.62 (m, 1H), 4.69-4.71 (d, J = 4.95 Hz, 1H), 5.67 (s, 2H), 6.86-6.89 (m, 1H), 6.94-6.99 (m, 1H), 7.17-7.23 (m, 1H), 7.35-7.37 (d, J = 8.2 Hz, 1H), 7.51-7.54 (m, 1H), 8.06 (s, 1H), 8.33-8.34 (d, J = 4.7 Hz, 1H), 8.59 (s, 1H); Mass (m/z): 386.2 (M + H)$^+$. |
| 10 | 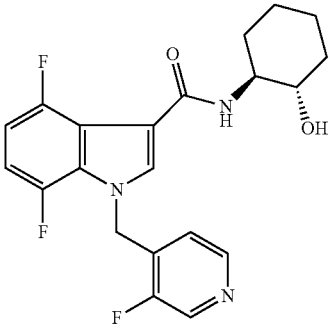<br>N-[(1S,2S)-2-Hydroxycyclohexyl]-1-(3-fluoropyridin-4-ylmethyl)-4,7-difluoro-1H-indole-3-carboxamide | $^1$H-NMR (DMSO-$d_6$, 400 MHz) δ ppm: 1.24-1.29 (m, 4H), 1.60-1.66 (m, 2H), 1.87-1.90 (m, 1H), 1.95-1.97 (m, 1H), 3.34-3.35 (m, 1H), 3.58-3.62 (m, 1H), 4.66-4.68 (d, J = 4.95 Hz, 1H), 5.72-5.76 (s, 2H), 6.76-6.79 (m, 1H), 6.88-6.93 (m, 1H), 6.97-7.03 (m, 1H), 7.67-7.64 (m, 1H), 8.08 (s, 1H), 8.33-8.35 (d, J = 4.8 Hz, 1H), 8.60 (s, 1H); Mass (m/z): 404.2 (M + H)$^+$. |
| 11 | 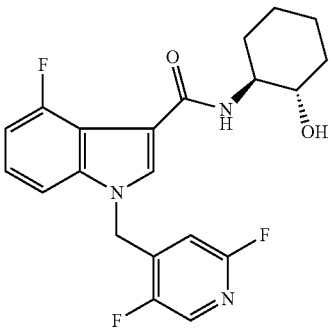<br>N-[(1S,2S)-2-Hydroxycyclohexyl]-1-(2,5-difluoropyridin-4-ylmethyl)-4-fluoro-1H-indole-3-carboxamide | $^1$H - NMR (CDCl$_3$, 400 MHz) δ ppm: 1.33-1.48 (m, 4H), 1.79 (m, 2H), 2.10-2.11 (m, 2H), 3.47-3.51 (m, 1H), 3.88 (m, 1H), 4.25 (bs, 1H), 5.42 (s, 2H), 6.27-6.28 (m, 1H), 6.98-7.09 (m, 2H), 7.21-7.23 (m, 2H), 8.03 (s, 1H), 8.11 (s, 1H); Mass (m/z): 404.2 (M + H)$^+$. |

-continued

| Example No. | Chemical name and Structure | Characterization data |
|---|---|---|
| 12 | 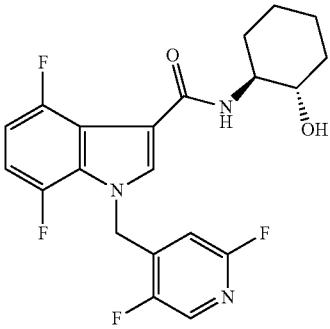<br>N-[(1S,2S)-2-Hydroxycyclohexyl]-1-(2,5-difluoropyridin-4-ylmethyl)-4,7-difluoro-1H-indole-3-carboxamide | $^1$H-NMR (DMSO-$d_6$, 400 MHz) δ ppm: 1.23 (m, 4H), 1.63 (m, 2H), 1.87-1.96 (m, 2H), 3.51 (m, 1H), 3.60 (m, 1H), 4.66 (m, 1H), 5.73 (s, 2H), 6.61 (s, 1H), 6.91-7.02 (m, 2H), 7.66 (m, 1H), 8.04 (s, 1H), 8.31 (s, 1H); Mass (m/z): 422.3 (M + H)$^+$. |
| 13 | 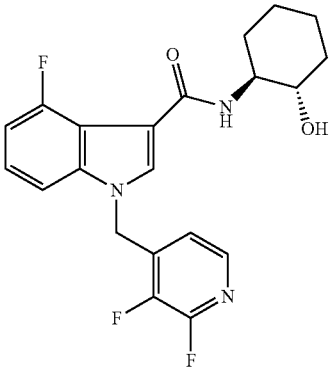<br>N-[(1S,2S)-2-Hydroxycyclohexyl]-1-(2,3-difluoropyridin-4-ylmethyl)-4-fluoro-1H-indole-3-carboxamide | $^1$H-NMR (DMSO-$d_6$, 400 MHz) δ ppm: 1.23-1.24 (m, 4H), 1.60-1.65 (m, 2H), 1.86-1.89 (m, 1H), 1.96-1.98 (m, 1H), 3.43-3.46 (m, 1H), 3.57-3.60 (m, 1H), 4.69-4.71 (d, J = 4.5 Hz, 1H), 5.74 (s, 2H), 6.76-6.77 (m, 1H), 6.95-7.00 (m, 1H), 7.18-7.23 (m, 1H), 7.36-7.38 (d, J = 8.1 Hz, 1H), 7.52-7.56 (m, 1H), 7.93-7.94 (d, J = 4.4 Hz, 1H), 8.06 (s, 1H); Mass (m/z): 404.2 (M + H)$^+$. |
| 14 | 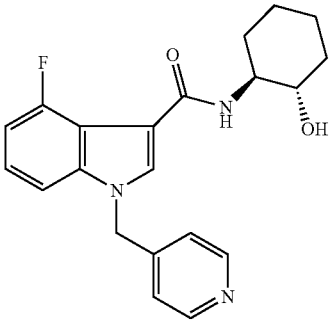<br>N-[(1S,2S)-2-Hydroxycyclohexyl]-1-(1-pyridin-4-ylmethyl)-4-fluoro-1H-indole-3-carboxamide | $^1$H - NMR (DMSO-$d_6$, 400 MHz) δ ppm: 1.23-1.25 (m, 4H), 1.60-1.66 (m, 2H), 1.87-2.00 (m, 2H), 3.40 (m, 1H), 3.60-3.61 (m, 1H), 4.71-4.72 (d, 1H), 5.57 (s, 2H), 6.90-6.95 (m, 1H), 7.13-7.16 (m, 1H), 7.18-7.20 (d, J = 7.9 Hz, 1H), 7.27-7.30 (m, 1H), 7.33-7.35 (d, J = 8.2 Hz, 1H), 7.46-7.49 (t, 1H), 7.73-7.77 (t, 1H), 8.09 (s, 1H), 8.50-8.52 (d, J = 4.1 Hz, 1H); Mass (m/z): 368.3 (M + H)$^+$. |

| Example No. | Chemical name and Structure | Characterization data |
|---|---|---|
| 15 | 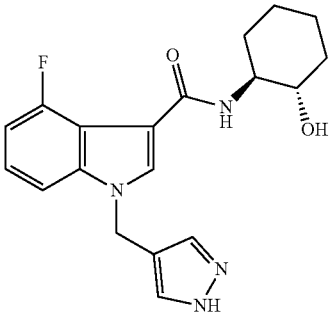<br>N-[(1S,2S)-2-Hydroxycyclohexyl]-1-(1H-pyrazol-4-ylmethyl)-4-fluoro-1H-indole-3-carboxamide | $^1$H - NMR (DMSO-$d_6$, 400 MHz) δ ppm: 1.16-1.24 (m, 4H), 1.59-1.65 (m, 2H), 1.85-1.97 (m, 2H), 3.29-3.34 (m, 1H), 3.58 (m, 1H), 4.70-4.71 (d, 1H), 5.31 (s, 2H), 6.90-6.95 (m, 1H), 7.17-7.20 (m, 1H), 7.40-7.44 (t, 1H), 7.51-7.54 (m, 2H), 7.81 (s, 1H), 7.99 (s, 1H), 12.79 (bs, 1H); Mass (m/z): 357.3 (M + H)$^+$. |
| 16 | 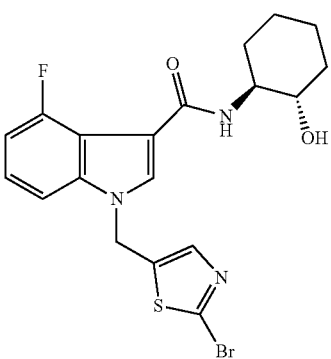<br>N-[(1S,2S)-2-Hydroxycyclohexyl]-1-(2-bromothiazol-5-ylmethyl)-4-fluoro-1H-indole-3-carboxamide | $^1$H - NMR (CDCl$_3$, 400 MHz) δ ppm: 1.25-1.36 (m, 4H), 1.75-1.78 (m, 2H), 2.04-2.13 (m, 2H), 3.44-3.49 (m, 1H), 3.84-3.86 (m, 1H), 4.30-4.31 (bs, 1H), 5.43 (s, 2H), 6.96-7.01 (m, 1H), 7.15-7.23 (m, 3H), 7.49-7.52 (m, 1H), 7.98 (s, 1H); Mass (m/z): 452.2, 454.2 (M + H)$^+$. |
| 17 | 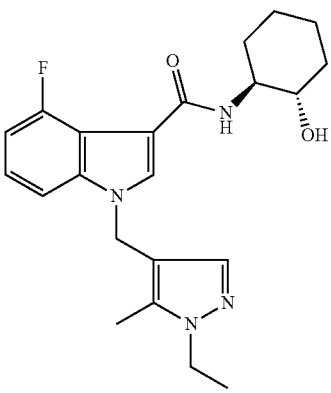<br>N-[(1S,2S)-2-Hydroxycyclohexyl]-1-(1-ethyl-5-methyl-1H-pyrazol-4-ylmethyl)-4-fluoro-1H-indole-3-carboxamide | $^1$H - NMR (DMSO-$d_6$, 400 MHz) δ ppm: 1.17-1.24 (m, 4H), 1.48-1.51 (t, 3H), 1.59-1.65 (m, 2H), 1.86-1.88 (m, 1H), 1.96-1.98 (m, 1H), 2.78 (s, 3H), 3.59-3.61 (m, 1H), 3.69-3.73 (m, 2H), 4.70-4.71 (d, J = 4.7 Hz, 1H), 5.28 (s, 2H), 6.90-6.95 (m, 1H), 7.18-7.22 (m, 1H), 7.40-7.45 (m, 2H), 7.50-7.52 (d, J = 8.27 Hz, 1H), 7.71 (s, 1H), 8.00 (s, 1H); Mass (m/z): 399.3 (M + H)$^+$. |

| Example No. | Chemical name and Structure | Characterization data |
|---|---|---|
| 18 | 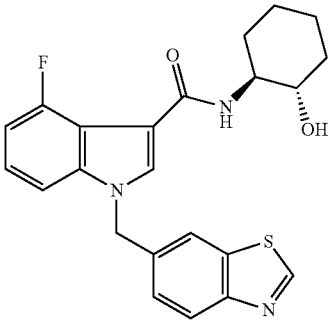<br>N-[(1S,2S)-2-Hydroxycyclohexyl]-1-(benzothiazol-6-ylmethyl)-4-fluoro-1H-indole-3-carboxamide | $^1$H - NMR (DMSO-$d_6$, 400 MHz) δ ppm: 1.16-1.33 (m, 4H), 1.60-1.66 (m, 2H), 1.87-1.99 (m, 2H), 3.29-3.34 (m, 1H), 3.58-3.62 (m, 1H), 4.70-4.71 (d, 1H), 5.65 (s, 2H), 6.90-6.96 (m, 1H), 7.14-7.19 (m, 1H), 7.42-7.51 (m, 3H), 8.04-8.09 (m, 2H), 8.16 (s, 1H), 9.37 (s, 1H); Mass (m/z): 424.20 (M + H)$^+$. |
| 19 | 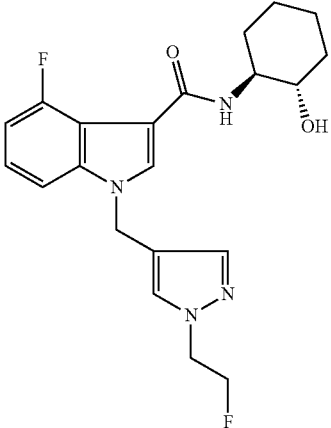<br>N-[(1S,2S)-2-Hydroxycyclohexyl]1-(1-(2-fluoroethyl)-1H-pyrazol-4-ylmethyl)-4-fluoro-1H-indole-3-carboxamide | $^1$H - NMR (DMSO-$d_6$, 400 MHz) δ ppm: 1.25-1.39 (m, 4H), 1.75-1.77 (m, 2H), 2.06-2.13 (m, 2H), 3.43-3.48 (m, 2H), 3.83-3.85 (m, 1H), 4.31-4.33 (t, 1H), 4.38- 4.40 (t, 1H), 4.65-4.68 (t, 1H), 4.77-4.79 (t, 1H), 5.20 (s, 2H), 6.92-6.98 (m, 1H), 7.17-7.24 (m, 3H), 7.39 (s, 1H), 7.48 (s, 1H), 7.96 (s, 1H); Mass (m/z): 403.2 (M + H)$^+$. |

Example 20

N-[(1S,2S)-2-Hydroxycyclohexyl]-1-(2-methylsulfanyl-pyridin-4-ylmethyl)-4,7-difluoro-1H-indole-3-carboxamide

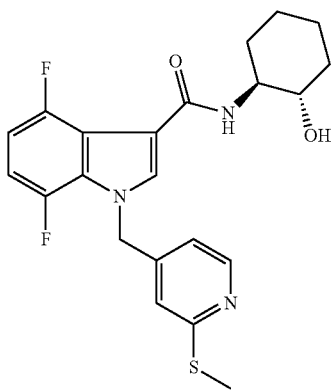 [SMILES: CSc1cc(Cn2cc(C(=O)N[C@H]3CCCC[C@@H]3O)c3c(F)ccc(F)c32)ccn1]

To a suspension of N-[(1S,2S)-2-hydroxycyclohexyl]-1-(2-fluoropyridin-4-ylmethyl)-4,7-difluoro-1H-indole-3-carboxamide (Example 8, 0.050 g, 0.00012 mole) in THF (10 mL) sodium thiomethoxide (0.020 g, 0.00029 mole) was added and warmed to 60° C. for 3 hours. Reaction mixture was cooled to RT and quenched in to water. Aqueous layer was extracted with ethyl acetate (25 mL×3). The organic layer was dried over $Na_2SO_4$ and concentrated under vacuum to obtain the crude residue, which was further purified by preparative TLC using ethyl acetate to provide the title compound.

Yield: 9.0 mg (16.5%); $^1$H-NMR (DMSO-$d_6$, 400 MHz) δ ppm: 1.24 (m, 5H), 1.60-1.66 (m, 2H), 1.87-1.90 (m, 1H), 1.94-1.97 (m, 1H), 2.46 (s, 3H), 3.34-3.35 (m, 1H), 3.60 (m, 1H), 5.55 (s, 2H), 6.71-6.73 (d, J=4 Hz, 1H), 6.86-6.92 (m, 1H), 6.97-7.02 (m, 2H), 7.65-7.68 (m, 1H), 8.09 (s, 1H), 8.35-8.36 (d, J=5.1 Hz, 1H); Mass (m/z): 432.2 (M+H)$^+$.

Example 21

N-[(1S,2S)-2-Hydroxycyclohexyl]-1-(2-methylsulfanyl-pyridin-4-ylmethyl)-4-fluoro-1H-indole-3-carboxamide

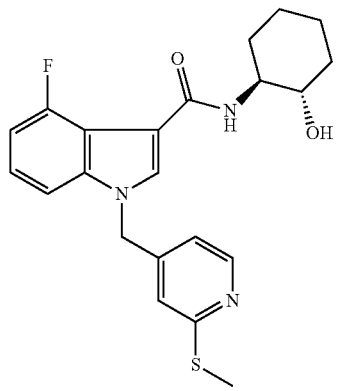 [SMILES: CSc1cc(Cn2cc(C(=O)N[C@H]3CCCC[C@@H]3O)c3c(F)cccc32)ccn1]

The title compound was prepared by the experimental procedure as described in the Example 20 using example 7 with some noncritical variations.

$^1$H NMR (DMSO-d$_6$, 400 MHz) δ ppm: 1.18-1.23 (m, 4H), 1.33-1.35 (m, 1H), 1.60-1.66 (m, 2H), 1.87-1.89 (m, 1H), 1.97-1.99 (m, 1H), 3.33-3.38 (m, 3H), 3.40-3.48 (m, 1H), 4.70-4.71 (d, 1H), 5.50 (s, 2H), 6.79-6.81 (m, 1H), 6.92-6.97 (m, 1H), 7.11 (s, 1H), 7.15-7.21 (m, 1H), 7.31-7.33 (m, 1H), 7.51-7.55 (m, 1H), 8.10 (s, 1H), 8.34-8.35 (m, 1H); Mass (m/z): 413.51 (M+H)$^+$.

Example 22

Cis-N-(3-Fluoropiperidin-4-yl)-1-(2-fluoropyridin-4-ylmethyl)-4,7-difluoro-1H-indole-3-carboxamide hydrochloride (Isomer-I)

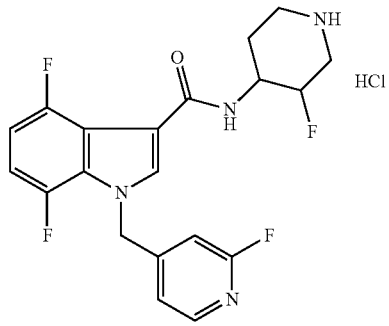 [SMILES: O=C(NC1CCNCC1F)c1cn(Cc2ccnc(F)c2)c2c(F)ccc(F)c12 ; Cl]

Step 1: cis-tert-Butyl 4-{[4,7-Difluoro-1-(2-fluoro-pyridin-4-ylmethyl)-1H-indole-3-carbonyl]-amino}-3-fluoro-piperidine-1-carboxylate (Isomer-I)

The title compound was synthesized by the procedure described in the Example 1 step (2) using 1-(2-fluoro-pyridin-4-ylmethyl)-4,7-difluoro-1H-indole-3-carboxylic acid and cis-tert-butyl 4-amino-3-fluoro-piperdine-1-carboxylate (Isomer-I), (I-9a). The crude product obtained was further purified by flash chromatography (methanol:DCM (1:99)) to obtain the title compound.

Yield: 1.0 g (83%). $^1$H-NMR (DMSO-d$_6$, 400 MHz) δ ppm: 1.40 (s, 9H), 1.68-1.74(m, 2H), 2.81-3.25 (m, 2H), 3.90-4.05 (m, 1H), 4.15-4.23 (m, 2H), 4.75-4.87 (m, 1H), 5.67 (s, 2H), 6.87-6.93 (m, 2H), 6.97-7.03 (m, 2H), 7.99-8.02 (m, 1H), 8.15 (s, 1H), 8.19-8.20 (m, 1H); Mass (m/z): 507.2 (M+H)$^+$.

Step 2: cis-N-(3-Fluoropiperidin-4-yl-1-(2-fluoropyridin-4-ylmethyl)-4,7-difluoro-1H-indole-3-carboxamide hydrochloride (Isomer-I)

To a 0-10° C. cooled solution of the above compound (0.675 g, 1.328 moles) in DCM (10 mL) under N$_2$, ethereal HCl (33% w/w, 0.243 g, 6.64 moles) was added slowly. After addition, reaction mass was allowed to 25° C. and stirred for 2 hours. Reaction Mass was concentrated under vacuum. The reaction mass was triturated with diethyl ether (5 mL×2), decanted the solvent and solids were dried under vacuum to afford the title compound.

Yield: 0.650 g (96.5%); $^1$H-NMR (DMSO-d$_6$, 400 MHz) δ ppm: 1.88-2.01 (m, 2H), 3.12-3.18 (m, 2H), 3.58-3.63 (m, 2H), 4.30-4.38 (m, 1H), 5.01-5.13 (d, 1H), 5.68 (s, 2H), 6.86-6.94 (m, 2H), 6.99-7.05 (m, 2H), 8.15 (s, 1H), 8.19-8.21 (m, 2H), 8.60-8.63 (m, 1H), 9.06-9.08 (m, 1H); Mass (m/z): 407.2 M+H)$^+$.

Example 23 cis-N-(3-Fluoropiperidin-4-yl-1-(2-fluoropyridin-4-ylmethyl)-4,7-difluoro-1H-indole-3-carboxamide hydrochloride (Isomer-II)

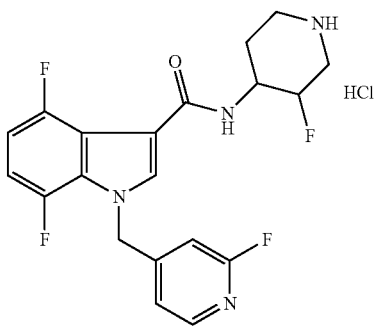 [SMILES: O=C(NC1CCNCC1F)c1cn(Cc2ccnc(F)c2)c2c(F)ccc(F)c12 ; Cl]

Step 1: cis-tert-Butyl 4-{[4,7-difluoro-1-(2-fluoro-pyridin-4-ylmethyl)-1H-indole-3-carbonyl]-amino}-3-fluoro-piperidine-1-carboxylate (Isomer-II)

The title compound was synthesized by the procedure described in the Example 1 step (2) using 1-(2-fluoro-pyridin-4-ylmethyl)-4,7-difluoro-1H-indole-3-carboxylic acid and cis-tert-butyl 4-amino-3-fluoro-piperdine-1-carboxylate (Isomer-II), (I-9b). The crude product obtained was further purified by flash chromatography (methanol:DCM (1:99)) to obtain the title compound.

Yield: 0.092 g (85%). $^1$H-NMR (CDCl$_3$, 400 MHz) δ ppm: 1.48 (s, 9H), 1.86-1.88 (m, 2H), 2.86 (m, 2H), 3.47-3.49 (m, 2H), 4.28-4.38 (m, 1H), 4.73-4.85 (m, 1H), 5.51 (s, 2H), 6.58 (s, 1H), 6.85-6.88 (m, 3H), 7.36-7.51 (m, 1H), 7.95 (s, 1H), 8.16-8.18 (d, J=5.1 Hz,1H); Mass (m/z): 507.2 (M+H)⁺.

Step 2: cis-N-(3-Fluoropiperidin-4-yl)-1-(2-fluoro-pyridin-4-ylmethyl)-4,7-difluoro-1H-indole-3-carboxamide hydrochloride (Isomer-II)

The title compound was synthesized by the procedure described in example 22, step 2 using tert-butyl 4-{[4,7-difluoro-1-(2-fluoropyridin-4-ylmethyl)-1H-indole-3-carbonyl]-amino }-3-fluoro-piperidine-1-carboxylate (Isomer-II).

Yield: 0.039 gm (97.2%). ¹H-NMR (DMSO-d₆, 400 MHz) δ ppm: 1.87-2.04 (m, 2H), 3.12-3.18 (m, 2H), 3.58-3.63 (m, 2H), 4.30-4.38 (m, 1H), 5.01-5.13 (d, 1H), 5.68 (s, 2H), 6.86-6.94 (m,2H), 6.99-7.05 (m, 2H), 8.15 (s, 1H), 8.19-8.21 (m, 2H), 8.60-8.63 (m, 1H), 9.06-9.08 (m, 1H); Mass (m/z): 407.2 (M+H)⁺.

Example 24 trans-N-(3-Fluoropiperidin-4-yl)-1-(2-fluoropyridin-4-ylmethyl)-4,7-difluoro-1H-indole-3-carboxamide hydrochloride (Isomer-I)

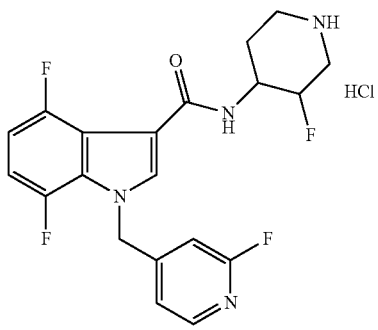 [SMILES: O=C(NC1CCNCC1F)c1cn(Cc2ccnc(F)c2)c2c(F)ccc(F)c12 ; Cl]

Step 1: trans-tert-Butyl 4-{[4,7-Difluoro-1-(2-fluoropyridin-4-ylmethyl)-1H-indole-3-carbonyl]-amino}-3-fluoro-piperidine-1-carboxylate (Isomer-I)

The title compound was synthesized by the procedure described in the Example 1, step (2) using 1-(2-fluoropyridin-4-ylmethyl)-4,7-difluoro-1H-indole-3-carboxylic acid and trans-tert-butyl 4-amino-3-fluoropiperdine-1-carboxylate (Isomer-I), (I-9c). The crude product obtained was further purified by flash chromatography (methanol:DCM (1:99) to obtain the title compound.

Yield: 0.05 g (60%). ¹H-NMR (CDCl₃, 400 MHz) δ ppm: 1.47 (s, 9H), 1.58-1.62 (m, 2H), 2.22-2.26 (m, 1H), 3.18-3.23 (m, 2H), 3.79-3.82 (m, 1H), 4.38-4.40 (m, 1H), 4.41-4.54 (m, 1H), 5.51 (s, 2H), 6.58 (s, 1H), 6.85-6.89 (m, 3H), 7.14-7.21 (m, 1H), 7.98 (s, 1H), 8.16-8.18 (d, J=5.1 Hz, 1H); Mass (m/z): 507.3 (M+H).

Step 2: trans-N-(3-Fluoropiperidin-4-yl)-1-(2-fluoropyridin-4-ylmethyl)-4,7-difluoro-1H-indole-3-carboxamide hydrochloride (Isomer-I)

The title compound was synthesized by the procedure described in example 22, step (2) using trans-tert-butyl 4-{[4,7-difluoro-1-(2-fluoropyridin-4-ylmethyl)-1H-indole-3-carbonyl]-amino }-3-fluoro-piperidine-1-carboxylate (Isomer-I).

Yield: 0.035 g (90%). ¹H-NMR (DMSO-d₆, 400 MHz) δ ppm: 1.78-1.82 (m, 1H), 2.11-2.13 (m, 1H), 3.12-3.18 (m, 1H), 3.26-3.29 (m, 2H), 3.56-3.59 (m, 1H), 4.33-4.34 (m, 1H), 4.79-4.92 (m, 1H), 5.68 (s, 2H), 6.85-6.93 (m, 2H), 6.99-7.05 (m, 2H), 8.14 (s, 1H), 8.19-8.21 (d, J=5.1 Hz, 1H), 8.35-8.37 (d, J=7.6 Hz, 1H), 9.05 (bs, 1H), 9.25 (bs, 1H); Mass (m/z): 407.2 (M+H)⁺.

Example 25 trans-N-(3-Fluoropiperidin-4-yl)-1-(2-fluoropyridin-4-ylmethyl)-4,7-difluoro-1H-indole-3-carboxamide hydrochloride (Isomer-II)

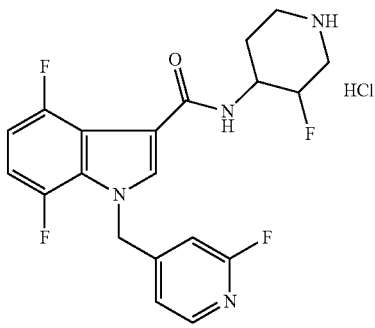 [SMILES: O=C(NC1CCNCC1F)c1cn(Cc2ccnc(F)c2)c2c(F)ccc(F)c12 ; Cl]

Step 1: trans-tert-Butyl 4-{[4,7-difluoro-1-(2-fluoro-pyridin-4-ylmethyl)-1H-indole-3-carbonyl]-amino}-3-fluoro-piperidine-1-carboxylate (Isomer-II)

The title compound was synthesized by the procedure described in the Example 1, step (2) using 1-(2-fluoropyridin-4-ylmethyl)-4,7-difluoro-1H-indole-3-carboxylic acid and trans-tert-butyl 4-amino-3-fluoro-piperdine-1-carboxylate (Isomer-II), (I-9d). The crude product obtained was further purified by flash chromatography (methanol:DCM (1:99) to obtain the title compound.

Yield: 0.05 g (90%). ¹H-NMR (CDCl₃, 400 MHz) δ ppm: 1.48 (s, 9H), 1.86-1.88 (m, 2H), 2.86 (m, 2H), 3.47-3.49 (m, 2H), 4.28-4.38 (m, 1H), 4.73-4.85 (m, 1H), 5.51 (s, 2H), 6.58 (s, 1H), 6.85-6.88 (m, 3H), 7.36-7.51 (m, 1H), 7.95 (s, 1H), 8.16-8.18 (d, J=5.1 Hz, 1H); Mass (m/z): 507.2 (M+H)⁺.

Step 2: trans-N-(3-Fluoropiperidin-4-yl)-1-(2-fluoropyridin-4-ylmethyl)-4,7-difluoro-1H-indole-3-carboxamide hydrochloride (Isomer-II)

The title compound was synthesized by the procedure described in example 22, step (2) using trans-tert-butyl 4-{[4,7-difluoro-1-(2-fluoropyridin-4-ylmethyl)-1H-indole-3-carbonyl]-amino }-3-fluoro-piperidine-1-carboxylate (Isomer-II).

Yield: 0.035 g (90%). ¹H-NMR (DMSO-d₆, 400 MHz) δ ppm: 1.78-1.82 (m, 1H), 2.11-2.13 (m, 1H), 3.13-3.18 (m, 1H), 3.25-3.29 (m, 2H), 3.55-3.59 (m, 1H), 4.33-4.34 (m, 1H), 4.78-4.92 (m, 1H), 5.68 (s, 2H), 6.85-6.93 (m, 2H), 6.99-7.05 (m, 2H), 8.14 (s, 1H), 8.19-8.21 (d, J=5.1 Hz, 1H), 8.35-8.37 (d, J=7.7 Hz, 1H), 9.05 (bs, 1H), 9.24 (bs, 1H); Mass (m/z): 407.2 (M+H)$^+$.

Examples 26 to 46

The compounds of Examples 26 to 46 were prepared by following the experimental procedures as described in the Examples 22-25, with some noncritical variations

| Example No. | Chemical name and Structure | Characterization data |
|---|---|---|
| 26 | cis-N-(3-Fluoropiperidin-4-yl)-1-(3-fluoropyridin-4-ylmethyl)-4,7-difluoro-1H-indole-3-carboxamide hydrochloride (Isomer-I) | $^1$H-NMR (DMSO-d$_6$, 400 MHz) δ ppm: 1.85-1.90 (m, 1H), 1.96-2.05 (m, 1H), 3.05-3.16 (m, 1H), 3.27-3.30 (m, 1H), 3.34-3.37 (m, 1H), 3.55-3.61 (m, 1H), 4.30-4.38 (m, 1H), 5.0-5.12 (m, 1H), 5.74 (s, 2H), 6.79-6.82 (m, 1H), 6.88-6.94 (m, 1H), 6.99-7.04 (m, 1H), 8.13 (s, 1H), 8.17-8.20 (m, 1H), 8.35-8.36 (d, J = 4.8 Hz, 1H), 8.62 (s, 1H), 8.68-8.71 (m, 1H), 9.33 (m, 1H); Mass (m/z): 407.2 (M + H)$^+$. |
| 27 | cis-N-(3-Fluoropiperidin-4-yl)-1-(2-chloropyridin-4-ylmethyl)-4-fluoro-1H-indole-3-carboxamide hydrochloride (Isomer-I) | $^1$H - NMR (DMSO-d$_6$, 400 MHz) δ ppm: 1.89-2.00 (m, 2H), 3.1-3.16 (m, 2H), 3.26-3.30 (m, 2H), 4.25-4.35 (m, 1H), 5.01-5.13 (d, 1H), 5.60 (s, 2H), 6.94-6.99 (m, 1H), 7.13-7.14 (m, 1H), 7.18-7.20 (m, 1H), 7.31 (s, 1H), 7.34-7.36 (m, 1H), 8.02-8.06 (m, 1H), 8.17 (s, 1H), 8.35-8.36 (m, 1H), 8.64-8.66 (m, 1H), 9.18-9.21 (m, 1H); Mass (m/z): 405.2 (M + H)$^+$. |
| 28 | cis-N-(3-Fluoropiperidin-4-yl)-1-(2-chloropyridin-4-ylmethyl)-4,7-difluoro-1H-indole-3-carboxamide hydrochloride (Racemate) | $^1$H- NMR (DMSO-d$_6$, 400 MHz) δ ppm: 1.87-2.00 (m, 2H), 3.09-3.18 (m, 2H), 3.57-3.63 (m, 2H), 4.30-4.38 (m, 1H), 5.01-5.13 (d, 1H), 5.65 (s, 2H), 6.88-6.94 (m, 1H), 6.99-7.06 (m, 2H), 7.22 (s, 1H), 8.15 (s, 1H), 8.20-8.22 (m, 1H), 8.36-8.37 (dd, J = 5.0 Hz, 1H), 8.60-8.63 (m, 1H), 9.05-9.07 (m, 1H); Mass (m/z): 423.2 (M + H)$^+$. |

| Example No. | Chemical name and Structure | Characterization data |
|---|---|---|
| 29 | 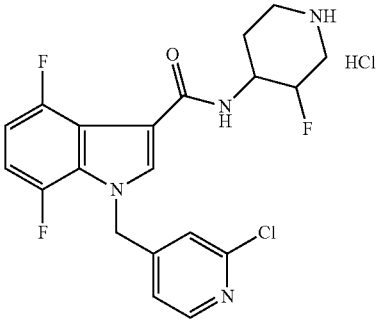<br>cis-N-(3-Fluoropiperidin-4-yl)-1-(2-chloropyridin-4-ylmethyl)-4,7-difluoro-1H-indole-3-carboxamide hydrochloride (Isomer-I) | $^1$H- NMR (DMSO-$d_6$, 400 MHz) δ ppm: 1.86-2.02 (m, 2H), 3.08-3.16 (m, 2H), 3.57-3.63 (m, 2H), 4.30-4.37 (m, 1H), 5.00- 5.12 (d, 1H), 5.65 (s, 2H), 6.88-6.94 (m, 1H), 6.99-7.06 (m, 2H), 7.22 (s, 1H), 8.15 (s, 1H), 8.20-8.22 (m, 1H), 8.36-8.37 (dd, J = 5.0 Hz, 1H), 8.68-8.71 (m, 1H), 9.32-9.35 (m, 1H); Mass (m/z): 423.2 (M + H)$^+$. |
| 30 | 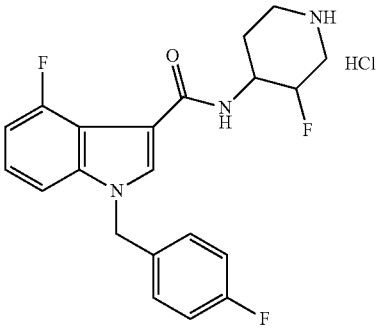<br>cis-N-(3-Fluoropiperidin-4-yl)-1-(4-fluorobenzyl)-4-fluoro-1H-indole-3-carboxamide hydrochloride (Isomer-I) | $^1$H- NMR (DMSO-$d_6$, 400 MHz) δ ppm: 1.92-2.02 (m, 2H), 3.08-3.17 (m, 2H), 3.27-3.38 (m, 2H), 4.30-4.38 (m, 1H), 5.01-5.13 (d, 1H), 5.48 (s, 2H), 6.91-6.96 (m, 1H), 7.14-7.21 (m, 3H), 7.31-7.35 (m, 2H), 7.40-7.42 (d, J = 8.3 Hz, 1H), 7.92-7.95 (t, 1H), 8.16 (s, 1H), 8.61-8.64 (m, 1H), 9.12-9.14 (m, 1H); Mass (m/z): 388.3 (M + H)$^+$. |
| 31 | 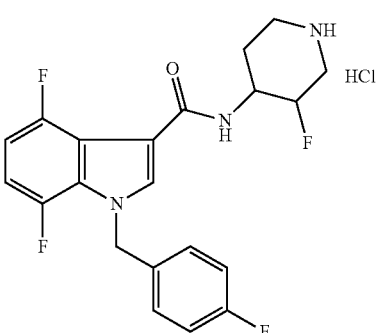<br>cis-N-(3-Fluoropiperidin-4-yl)-1-(4-fluorobenzyl)-4,7-difluoro-1H-indole-3-carboxamide hydrochloride (Isomer-I) | $^1$H- NMR (DMSO-$d_6$, 400 MHz) δ ppm: 1.89-2.00 (m, 2H), 3.11-3.14 (m, 2H), 3.56-3.59 (m, 2H), 4.29-4.37 (m, 1H), 5.00-5.12 (d, 1H), 5.53 (s, 2H), 6.86-6.90 (m, 2H), 7.15-7.23 (m, 4H), 8.15 (s, 2H), 8.61-8.63 (m, 1H), 9.09-9.12 (m, 1H); Mass (m/z): 406.2 (M + H)$^+$. |

| Example No. | Chemical name and Structure | Characterization data |
|---|---|---|
| 32 | 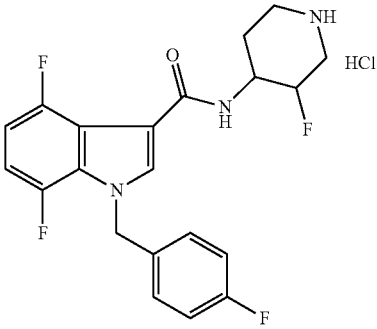<br>cis-N-(3-Fluoropiperidin-4-yl)-1-(4-fluorobenzyl)-4,7-difluoro-1H-indole-3-carboxamide hydrochloride (Isomer-II) | $^1$H - NMR (DMSO-d$_6$, 400 MHz) δ ppm: 1.86-1.89 (m, 1H), 1.94-2.03 (m, 1H), 3.11-3.13 (m, 1H), 3.26-3.34 (m, 2H), 3.56-3.58 (m, 1H), 4.28-4.36 (m, 1H), 5.00-5.12 (d, 1H), 5.53 (s, 2H), 6.85-6.91 (m, 1H), 7.00-7.04 (m, 1H), 7.15-7.25 (m, 4H), 8.16 (bs, 2H), 8.63-8.65 (d, J = 9.24 Hz, 1H), 9.17-9.19 (d, J = 9.84 Hz, 1H); Mass (m/z): 406.4 (M + H)$^+$. |
| 33 | 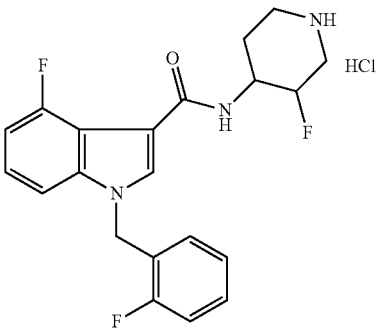<br>cis-N-(3-Fluoropiperidin-4-yl)-1-(2-fluorobenzyl)-4-fluoro-1H-indole-3-carboxamide hydrochloride (Isomer-I) | $^1$H- NMR (DMSO-d$_6$, 400 MHz) δ ppm: 1.91-1.99 (m, 2H), 3.09-3.17 (m, 2H), 3.27-3.34 (m, 2H), 4.29-4.39 (m, 1H), 5.01-5.13 (d, 1H), 5.56 (s, 2H), 6.93-6.98 (m, 1H), 7.13-7.27 (m, 4H), 7.34-7.39 (m, 1H), 7.40-7.43 (d, J = 8.2 Hz, 1H), 7.95-7.98 (t, 1H), 8.07 (s, 1H), 8.61 (m, 1H), 9.01-9.03 (m, 1H); Mass (m/z): 388.2 (M + H)$^+$. |
| 34 | 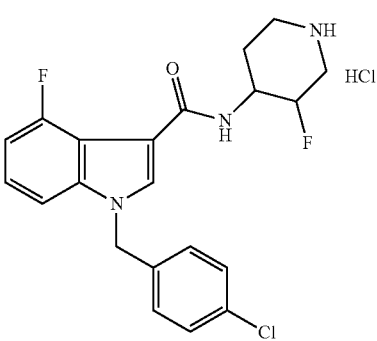<br>cis-N-(3-Fluoropiperidin-4-yl)-1-(4-chlorobenzyl)-4-fluoro-1H-indole-3-carboxamide hydrochloride (Isomer-I) | $^1$H- NMR (DMSO-d$_6$, 400 MHz) δ ppm: 1.88-1.99 (m, 2H), 3.12-3.15 (m, 2H), 3.28-3.30 (m, 2H), 4.22-4.38 (m, 1H), 5.01-5.13 (d, 1H), 5.50 (s, 2H), 6.92-6.97 (m, 1H), 7.12 (s, 1H), 7.16-7.21 (m, 1H), 7.26-7.28 (d, J = 8.3 Hz, 2H), 7.37-7.41 (t, 3H), 7.95-7.99 (t, 1H), 8.16 (s, 1H), 8.58-8.60 (m, 1H), 8.95-8.98 (m, 1H); Mass (m/z): 404.2 (M + H)$^+$. |

-continued

| Example No. | Chemical name and Structure | Characterization data |
|---|---|---|
| 35 | 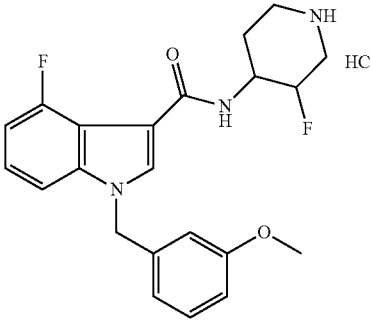<br>cis-N-(3-Fluoropiperidin-4-yl)-4-fluoro-1-(3-methoxybenzyl)-1H-indole-3-carboxamide hydrochloride (Isomer-I) | $^1$H - NMR (DMSO-d$_6$, 400 MHz) δ ppm: 1.92-1.99 (m, 2H), 3.12-3.16 (m, 2H), 3.42-3.57 (m, 2H), 3.71 (s, 3H), 4.30-4.40 (m, 1H), 5.02-5.13 (d, 1H), 5.46 (s, 2H), 6.77-6.79 (d, J = 7.3 Hz, 1H), 6.84-6.85 (m, 2H), 6.91-6.96 (m, 1H), 7.16-7.26 (m, 2H), 7.39-7.41 (d, J = 8.1 Hz, 1H), 7.93-7.96 (t, 1H), 8.14 (s, 1H), 8.59 (bs, 1H), 9.04 (bs, 1H); Mass (m/z): 400.3 (M + H)$^+$. |
| 36 | 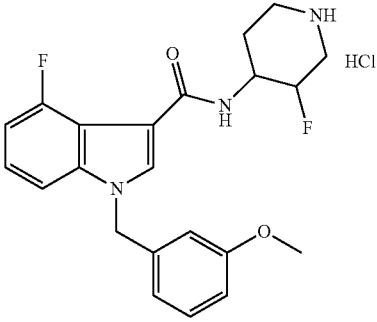<br>cis-N-(3-Fluoropiperidin-4-yl)-4-fluoro-1-(3-methoxybenzyl)-1H-indole-3-carboxamide hydrochloride (Isomer-II) | $^1$H - NMR (DMSO-d$_6$, 400 MHz) δ ppm: 1.91-2.02 (m, 2H), 3.11-3.13 (m, 1H), 3.26-3.29 (m, 2H), 3.56-3.58 (m, 1H), 3.70 (s, 3H), 4.30-4.38 (m, 1H), 5.01-5.13 (d, 1H), 5.46 (s, 2H), 6.77-6.96 (m, 4H), 7.17-7.25 (m, 2H), 7.39-7.41 (d, J = 8.32 Hz, 1H), 7.94-7.97 (t, J = 7.08 Hz, 1H), 8.15 (s, 1H), 8.66-8.68 (bs, 3H), 9.27-9.30 (s, 3H); Mass (m/z): 400.2 (M + H)$^+$. |
| 37 | 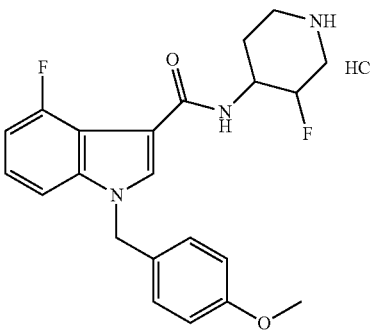<br>cis-N-(3-Fluoropiperidin-4-yl)-1-(4-methoxybenzyl)-4-fluoro-1H-indole-3-carboxamide hydrochloride (Isomer-II) | $^1$H - NMR (DMSO-d$_6$, 400 MHz) δ ppm: 1.90-2.06 (m, 2H), 2.65-2.67 (m, 1H), 3.07-3.15 (m, 1H), 3.56-3.62 (m, 2H), 3.69 (s, 3H), 4.28-4.36 (m, 1H), 4.99-5.11 (m, 1H), 5.39 (s, 2H), 6.86-6.94 (m, 3H), 7.11-7.19 (m, 1H), 7.22-7.24 (d, J = 8.3 Hz, 2H), 7.40-7.43 (d, J = 8.2 Hz, 1H), 7.89-7.93 (t, 1H), 8.11 (s, 1H), 8.61 (m, 1H), 9.04-9.06 (m, 1H); Mass (m/z): 400.4 (M + H)$^+$. |

| Example No. | Chemical name and Structure | Characterization data |
|---|---|---|
| 38 | 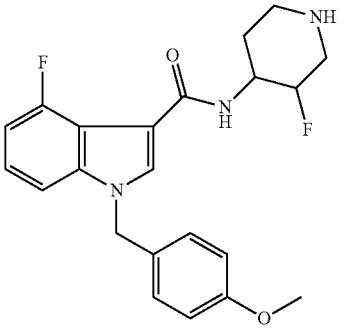<br>cis-N-(3-Fluoropiperidin-4-yl)-1-(4-methoxybenzyl)-4-fluoro-1H-indole-3-carboxamide hydrochloride (Isomer-I) | $^1$H - NMR (DMSO-d$_6$, 400 MHz) δ ppm: 1.92-1.99 (m, 2H), 3.11-3.16 (m, 2H), 3.27-3.37 (m, 2H), 3.70 (s, 3H), 4.30-4.39 (m, 1H), 5.01-5.13 (d, 1H), 5.40 (s, 2H), 6.87-6.90 (d, J = 8.57 Hz, 2H), 6.92-6.95 (m, 1H), 7.15-7.21 (m, 1H), 7.23-7.26 (d, J = 8.52 Hz, 2H), 7.41-7.44 (d, J = 8.24 Hz, 1H), 7.89-7.92 (m, 1H), 8.12 (m, 1H), 8.62-8.64 (m, 1H), 9.12-9.15 (m, 1H); Mass (m/z): 400.4 (M + H)$^+$. |
| 39 | 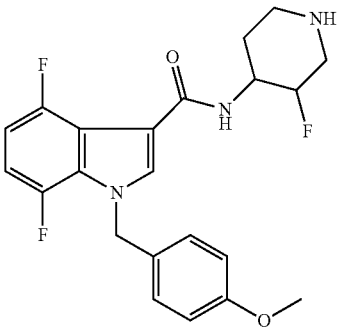<br>cis-N-(3-Fluoropiperidin-4-yl)-1-(4-methoxybenzyl)-4,7-difluoro-1H-indole-3-carboxamide hydrochloride (Isomer-I) | $^1$H NMR (DMSO-d$_6$, 400 MHz) δ ppm: 1.86-1.89 (m, 1H), 1.93-2.00 (m, 1H), 3.10-3.16 (m, 1H), 3.20-3.30 (m, 1H), 3.39-3.47 (m, 1H), 3.55-3.61 (m, 1H), 3.70 (3H, 4.28-4.36 (m, 1H), 5.00-5.11 (m, 1H), 5.46 (s, 2H), 6.85-6.90 (m, 3H), 6.98-7.03 (m, 1H), 7.15-7.17 (d, 2H), 8.08-8.12 (m, 2H), 8.63-8.65 (m, 1H), 9.18 (m, 1H); Mass (m/z): 418.2 (M + H)$^+$. |
| 40 | 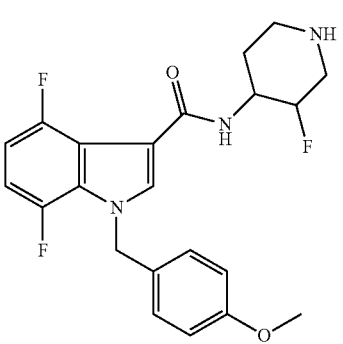<br>cis-N-(3-Fluoropiperidin-4-yl)-1-(4-methoxybenzyl)-4,7-difluoro-1H-indole-3-carboxyamide hydrochloride (Isomer-II) | $^1$H NMR (DMSO-d$_6$, 400 MHz) δ ppm: 1.86-1.99 (m, 2H), 3.10-3.19 (m, 1H), 3.20-3.30 (m, 1H), 3.38-3.45 (m, 1H), 3.56-3.59 (m, 1H), 3.70 (3H, s), 4.28-4.36 (m, 1H), 5.00-5.12 (m, 1H), 5.46 (s, 2H), 6.85-6.90 (m, 3H), 6.98-7.04 (m, 1H), 7.14-7.16 (d, 2H), 8.09-8.12 (m, 2H), 8.55-8.65 (m, 1H), 9.10-9.16 (m, 1H); Mass (m/z): 418.2 (M + H)$^+$. |

| Example No. | Chemical name and Structure | Characterization data |
|---|---|---|
| 41 | 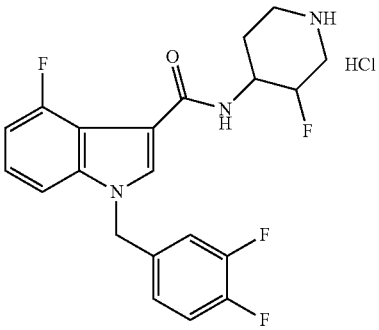<br>cis-N-(3-Fluoropiperidin-4-yl)-1-(3,4-difluorobenzyl)-4-fluoro-1H-indole-3-carboxamide hydrochloride (Isomer-I) | $^1$H - NMR (DMSO-$d_6$, 400 MHz) δ ppm: 1.89-2.00 (m, 2H), 3.08-3.17 (m, 2H), 3.27-3.30 (m, 2H), 4.29-4.38 (m, 1H), 5.01-5.13 (d, 1H), 5.49 (s, 2H), 6.92-6.97 (m, 1H), 7.12 (s, 1H), 7.17-7.22 (m, 1H), 7.37-7.43 (m, 3H), 7.94-7.98 (t, 1H), 8.17 (s, 1H), 8.63-8.66 (m, 1H), 9.17-9.20 (m, 1H); Mass (m/z): 406.3 (M + H)$^+$. |
| 42 | 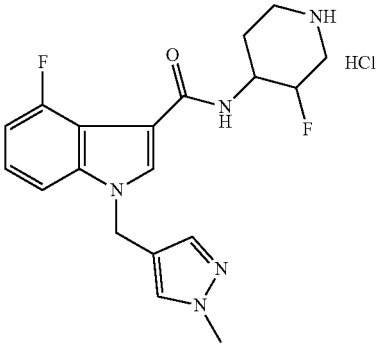<br>cis-N-(3-Fluoropiperidin-4-yl)-1-(1-methyl-1H-pyrazol-4-yl-methyl)-4-fluoro-1H-indole-3-carboxamide hydrochloride (Isomer-I) | $^1$H- NMR (DMSO-$d_6$, 400 MHz) δ ppm: 1.91-1.98 (m, 2H), 3.11-3.17 (m, 2H), 3.57-3.60 (m, 2H), 3.76 (s, 3H), 4.29-4.37 (m, 1H), 5.00-5.12 (d, 1H), 5.30 (s, 2H), 6.91-6.96 (m, 1H), 7.19-7.24 (m, 1H), 7.46 (s, 1H), 7.52-7.54 (d, J = 8.2 Hz, 1H), 7.29 (s, 1H), 7.86-7.89 (t, 1H), 8.06 (s, 1H), 8.59-8.62 (bs, 1H), 9.04-9.06 (bs, 1H); Mass (m/z): 374.3 (M + H)$^+$. |
| 43 | 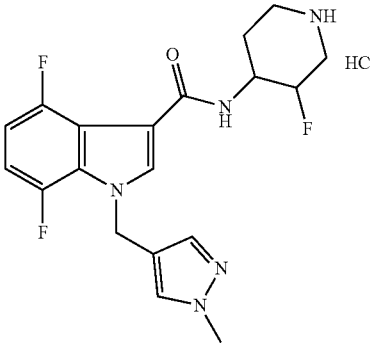<br>cis-N-(3-Fluoropiperidin-4-yl)-1-(1-methyl-1H-pyrazol 4-yl-methyl)-4,7-difluoro-1H-indole-3-carboxamide hydrochloride (Isomer-I) | $^1$H-NMR (DMSO-$d_6$, 400 MHz) δ ppm: 1.86-1.98 (m, 2H), 3.08-3.15 (m, 2H), 3.27-3.34 (m, 2H), 3.75 (s, 3H), 4.24-4.34 (m, 1H), 4.99-5.11 (d, 1H), 5.36 (s, 2H), 6.85-6.90 (m, 1H), 7.02-7.08 (m, 1H), 7.41 (s, 1H), 7.67 (s, 1H), 8.02-8.05 (m, 2H), 8.62 (m, 1H), 9.04-9.07 (m, 1H); Mass (m/z): 392.1 (M + H)$^+$. |

| Example No. | Chemical name and Structure | Characterization data |
|---|---|---|
| 44 | 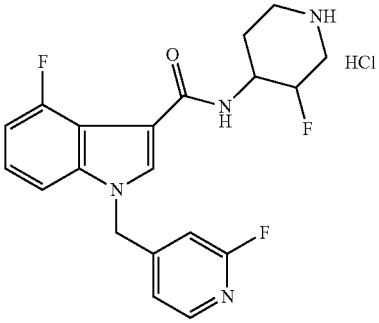<br>cis-N-(3-Fluoropiperidin-4-yl)-1-(2-fluoropyridin-4-ylmethyl)-4-fluoro-1H-indole-3-carboxamide hydrochloride (Isomer-I) | $^1$H - NMR (DMSO-$d_6$, 400 MHz) δ ppm: 1.85-2.01 (m, 2H), 3.08-3.16 (m, 2H), 3.27-3.30 (m, 2H), 4.31-4.38 (m, 1H), 5.01-5.13 (d, 1H), 5.64 (s, 2H), 6.94-6.99 (m, 2H), 7.08-7.09 (m, 1H), 7.17-7.22 (s, 1H), 7.34-7.36 (m, 1H), 8.01-8.04 (m, 1H), 8.17-8.19 (m, 2H), 8.67-8.69 (m, 1H), 9.28-9.30 (m, 1H); Mass (m/z): 389.2 (M + H)$^+$. |
| 45 | 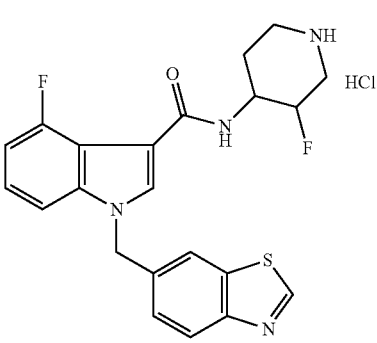<br>cis-N-(3-Fluoropiperidin-4-yl)-1-(benzothiazol-6-ylmethyl)-4-fluoro-1H-indole-3-carboxamide hydrochloride (Isomer-I) | $^1$H - NMR (DMSO-$d_6$, 400 MHz) δ ppm: 1.85-2.02 (m, 2H), 3.12-3.17 (m, 1H), 3.27-3.35 (m, 2H), 3.55-3.63 (m, 1H), 4.31-4.39 (m, 1H), 5.02-5.13 (d, 1H), 5.66 (s, 2H), 6.91-6.96 (m, 1H), 7.16-7.21 (m, 1H), 7.44-7.46 (d, J = 8.3 Hz, 2H), 7.94-7.98 (t, 1H), 8.04-8.10 (m, 2H), 8.21 (s, 1H), 8.61-8.64 (m, 1H), 9.10-9.12 (m, 1H), 9.37 (s, 1H); Mass (m/z): 427.1 (M + H)$^+$. |
| 46 | 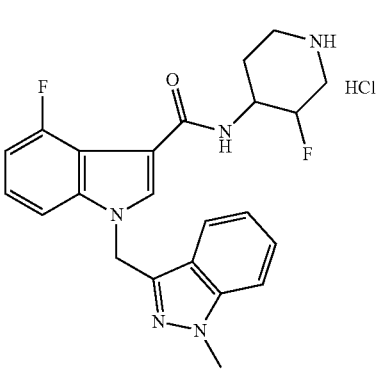<br>cis-N-(3-Fluoropiperidin-4-yl)-1-(1-methyl-1H-indazole-3-ylmethyl)-4-fluoro-1H-indole-3-carboxamide hydrochloride (Isomer-I) | $^1$H - NMR (DMSO-$d_6$, 400 MHz) δ ppm: 1.82-1.95 (m, 1H), 1.98-2.05 (m, 1H), 3.08-3.16 (m, 1H), 3.26-3.30 (m, 1H), 3.56-3.62 (m, 2H), 4.01 (s, 3H), 4.28-4.37 (m, 1H), 5.00-5.12 (m, 1H), 5.82 (s, 2H), 6.90-6.95 (m, 1H), 7.09-7.13 (t, 1H), 7.18-7.23 (m, 1H), 7.36-7.40 (m, 7.54-7.61 (m, 2H), 7.66-7.68 (m, 1H), 7.89-7.93 (t, 1H), 8.19 (s, 1H), 8.60-8.62 (m, 1H), 9.08-9.10 (m, 1H); Mass (m/z): 424.2(M + H)$^+$. |

Example 47 cis-N-(3-Fluoropiperidin-4-yl)-1-(2-fluoropyridin-4-ylmethyl)-4,7-difluoro-1H-indole-3-carboxamide (Isomer-II)

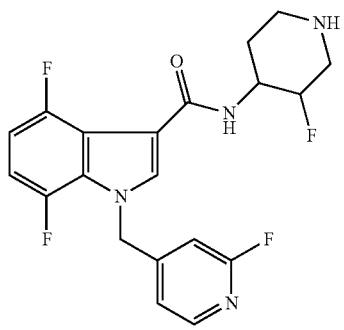

The compound of example 23 (0.033 g, 0.000074 moles) was dissolved in ice cold water (5.0 mL) and pH was adjusted to ~8.0 using 2M sodium bicarbonate solution (0.5 mL) at 5-10° C. Aqueous layer was extracted with dichloromethane (5 mL×3). The combined organic phase was washed with water (5 mL), brine solution (5 mL) and dried over $Na_2SO_4$. The organic phase was concentrated under vacuum to afford the title compound.

Yield: 0.030 g (99.3%); $^1$H-NMR (DMSO-$d_6$, 400 MHz) δ ppm: 1.62-1.68 (m, 2H), 2.56 (m, 1H), 2.67-2.81 (m, 2H), 2.93-2.96 (m, 1H), 3.08-3.14 (m, 1H), 4.05-4.14 (m, 1H), 4.60-4.72 (d, 1H), 5.67 (s, 2H), 6.87-6.94 (m, 2H), 6.97-7.03 (m, 2H), 7.87-7.91 (t, 1H), 8.16-8.19 (m, 2H); Mass (m/z): 407.2 (M+H)$^+$.

Examples 48 to 71

The following compounds of example 48 to 71 can be prepared from the hydrochloride salt compounds of examples 22 to 46 by following the experimental procedure as described in the example 47.

| Example No. | Chemical name and Structure | Characterization data |
|---|---|---|
| 48 | trans-N-(3-Fluoropiperidin-4-yl)-1-(2-fluoropyridin-4-ylmethyl)-4,7-difluoro-1H-indole-3-carboxamide (Isomer-I) | $^1$H - NMR (CDCl$_3$, 400 MHz) δ ppm: 2.23-2.27 (m, 1H), 2.77-2.90 (m, 3H), 2.81-2.98 (bs, 1H), 3.30-3.37 (m, 1H), 4.34-4.39 (m, 2H), 4.48-4.51 (m, 1H), 5.51 (s, 2H), 6.58 (s, 1H), 6.85-6.89 (m, 3H), 7.18-7.20 (m, 1H), 7.98 (s, 1H), 8.16-8.17 (d, J = 5.1 Hz, 1H); Mass (m/z): 407.2 (M + H)$^+$. |
| 49 | trans-N-(3-Fluoropiperidin-4-yl)-1-(2-fluoropyridin-4-ylmethyl)-4,7-difluoro-1H-indole-3-carboxamide (Isomer-II) | $^1$H - NMR (CDCl$_3$, 400 MHz) δ ppm: 2.23-2.27 (m, 1H), 2.77-2.90 (m, 3H), 2.81-2.98 (bs, 1H), 3.30-3.38 (m, 1H), 4.34-4.40 (m, 2H), 4.49-4.52 (m, 1H), 5.51 (s, 2H), 6.58 (s, 1H), 6.83-6.88 (m, 3H), 7.18-7.22 (m, 1H), 7.98 (s, 1H), 8.16-8.17 (d, J = 5.1 Hz, 1H); Mass (m/z): 407.2 (M + H)$^+$. |

| Example No. | Chemical name and Structure | Characterization data |
|---|---|---|
| 50 | 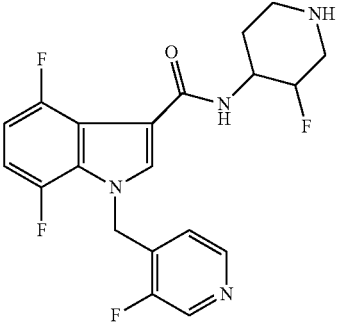<br>cis-N-(3-Fluoropiperidin-4-yl)-1-(3-fluoropyridin-4-ylmethyl)-4,7-difluoro-1H-indole-3-carboxamide (Isomer-I) | $^1$H - NMR (DMSO-d$_6$, 400 MHz) δ ppm: 1.61-1.68 (m, 2H), 1.85-2.05 (m, 1H), 2.54-2.59 (m, 1H), 2.67-2.80 (m, 1H), 2.92-2.99 (m, 1H), 3.08-3.14 (m, 1H), 4.05-4.13 (m, 1H), 4.59-4.72 (m, 1H), 5.73 (s, 2H), 6.77-6.80 (m, 1H), 6.89-7.03 (m, 2H), 7.86-7.89 (m, 1H), 8.14 (S, 1H), 8.33-8.34 (d, J = 4.8 Hz 1H), 8.60 (s, 1H); Mass (m/z): 407.3 (M + H)$^+$. |
| 51 | 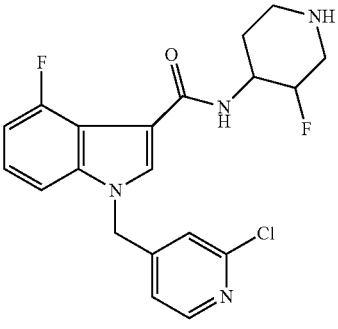<br>cis-N-(3-Fluoropiperidin-4-yl)-1-(2-chloropyridin-4-ylmethyl)-4-fluoro - -1H-indole-3-carboxamide (Isomer-I) | $^1$H - NMR (CDCl$_3$, 400 MHz) δ ppm: 1.72-1.83 (m, 1H), 1.89-1.92 (m, 1H), 2.74-2.82 (m, 1H), 2.83-2.90 (bs, 1H), 2.92-2.95 (d, J = 13.26 Hz, 1H), 3.15-3.19 (m, 1H), 3.35-3.41 (m, 1H), 4.30-4.38 (m, 1H), 4.69-4.81 (d, 1H), 5.34 (s, 2H), 6.88-6.97 (d, J = 4.99 Hz, 1H), 7.00-7.02 (m, 3H), 7.17-7.23 (m, 1H), 7.48-7.54 (m, 1H), 7.99 (s, 1H), 8.32-8.33 (d, J = 5.1 Hz, 1H); Mass (m/z): 405.2 (M + H)$^+$. |
| 52 | 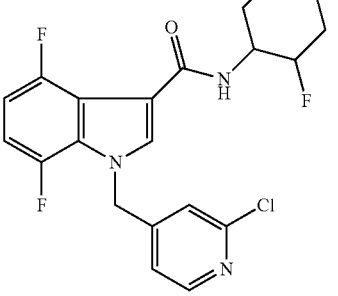<br>cis-N-(3-Fluoropiperidin-4-yl)-1-(2-chloropyridin-4-ylmethyl)-4,7-difluoro-1H-indole-3-carboxamide (Racemate) | $^1$H- NMR (DMSO-d$_6$, 400 MHz) δ ppm: 1.62-1.68 (m, 2H), 2.50 (bs, 1H), 2.93-2.96 (m, 2H), 3.08-3.11 (m, 2H), 4.05-4.14 (m, 1H), 4.60-4.72 (d, 1H), 5.64 (s, 2H), 6.89-6.92 (m, 1H), 6.94-7.05 (m, 2H), 7.24 (s, 1H), 7.88-7.91 (t, 1H), 8.16 (m, 1H), 8.35-8.36 (d, J = 5.0 Hz, 1H); Mass (m/z): 423.2 (M + H)$^+$. |

| Example No. | Chemical name and Structure | Characterization data |
|---|---|---|
| 53 | 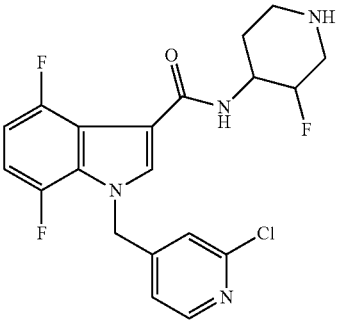 [SMILES: O=C(NC1CCNCC1F)c1cn(Cc2ccnc(F)c2)c2c(F)ccc(F)c12]<br>cis-N-(3-Fluoropiperidin-4-yl)-1-(2-chloropyridin-4-ylmethyl)-4,7-difluoro-1H-indole-3-carboxamide (Isomer-I) | $^1$H NMR (DMSO-$d_6$, 400 MHz) δ ppm: 1.62-1.71 (m, 2H), 1.93-2.00 (m, 1H), 2.55-2.58 (bs, 1H), 2.67-2.81 (m, 1H), 2.93-2.99 (m, 1H), 3.08-3.18 (m, 1H), 4.05-4.13 (m, 1H), 4.60-4.72 (m, 1H), 5.64 (s, 2H), 6.89-6.95 (m, 1H), 6.98-7.05 (m, 2H), 7.24 (s, 1H), 7.88-7.91 (m, 1H), 8.16 (s, 1H), 8.35-8.36 (m, 1H); Mass (m/z): 423.2 (M + H)$^+$. |
| 54 | 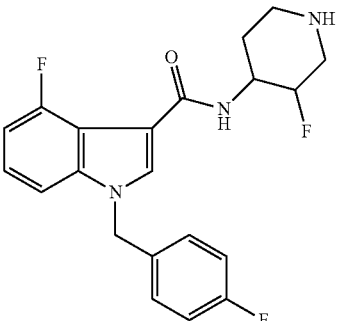<br>cis-N-(3-Fluoropiperidin-4-yl)-1-(4-fluorobenzyl)-4-fluoro-1H-indole-3-carboxamide (Isomer-I) | $^1$H- NMR (DMSO-$d_6$, 400 MHz) δ ppm: 1.61-1.65 (m, 2H), 2.56 (bs, 1H), 2.67-2.71 (m, 1H), 2.80 (m, 1H), 2.92-2.95 (m, 1H), 3.08-3.14 (m, 1H), 4.04-4.14 (m, 1H), 4.59-4.72 (d, 1H), 5.48 (s, 2H), 6.93-6.98 (m, 1H), 7.13-7.21 (m, 3H), 7.31-7.35 (m, 2H), 7.40-7.42 (d, J = 8.3 Hz, 1H), 7.64-7.68 (t, 1H), 8.17 (s, 1H); Mass (m/z): 388.3 (M + H)$^+$. |
| 55 | 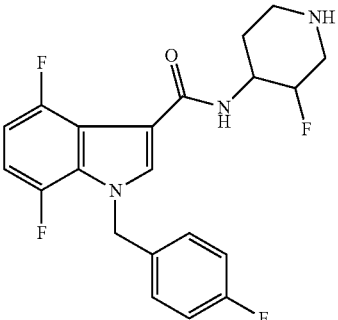<br>cis-N-(3-Fluoropiperidin-4-yl)-1-(4-fluorobenzyl)-4,7-difluoro-1H-indole-3-carboxamide (Isomer-I) | $^1$H- NMR (DMSO-$d_6$, 400 MHz) δ ppm: 1.61-1.67 (m, 2H), 2.55 (bs, 1H), 2.73 (m, 1H), 2.89-2.92 (m, 1H), 3.11-3.15 (m, 2H), 4.04-4.12 (m, 1H), 4.59-4.72 (d, 1H), 5.53 (s, 2H), 6.86-6.92 (m, 1H), 6.97-7.03 (m, 1H), 7.14-7.18 (m, 2H), 7.21-7.24 (m, 2H), 7.80-7.84 (t, 1H), 8.16 (s, 1H); Mass (m/z): 406.3 (M + H)$^+$. |

| Example No. | Chemical name and Structure | Characterization data |
|---|---|---|
| 56 | 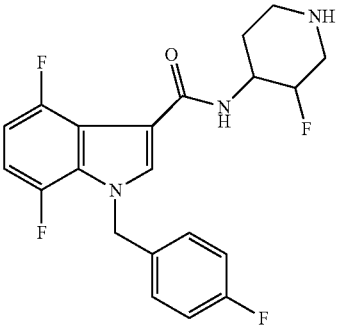<br>cis-N-(3-Fluoropiperidin-4-yl)-1-(4-fluorobenzyl)-4,7-difluoro-1H-indole-3-carboxamide (Isomer-II) | $^1$H - NMR (DMSO-d$_6$, 400 MHz) δ ppm: 1.63-1.89 (m, 2H), 2.56 (bs, 1H), 2.73 (m, 1H), 2.92-2.95 (m, 1H), 3.11-3.14 (m, 2H), 4.04 (m, 1H), 4.58-4.72 (d, 1H), 5.53 (s, 2H), 6.85-6.92 (m, 1H), 6.97-7.03 (m, 1H), 7.15-7.18 (m, 2H), 7.21-7.24 (m, 2H), 7.80-7.84 (t, 1H), 8.16 (s, 1H); Mass (m/z): 406.4 (M + H)$^+$. |
| 57 | 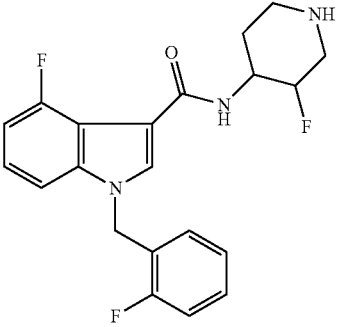<br>cis-N-(3-Fluoropiperidin-4-yl)-1-(2-fluorobenzyl)-4-fluoro-1H-indole-3-carboxamide (Isomer-I) | $^1$H NMR (DMSO-d$_6$, 400 MHz) δ ppm: 1.62-1.65 (m, 2H), 2.54 (bs, 1H), 2.67-2.71 (m, 1H), 2.77-2.80 (m, 1H), 2.92-2.95 (m, 2H), 3.08-3.14 (m, 1H), 4.04-4.14 (m, 1H), 4.59-4.72 (d, 1H), 5.59 (s, 2H), 6.94-6.99 (m, 1H), 7.14-7.26 (m, 3H), 7.34-7.42 (m, 2H), 7.64-7.68 (t, 1H), 8.09 (s, 1H); Mass (m/z): 388.3 (M + H)$^+$. |
| 58 | 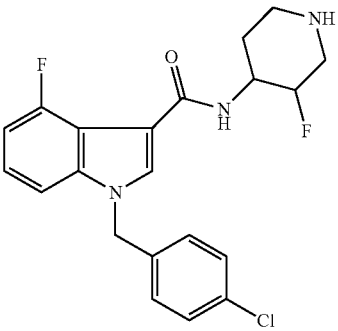<br>cis-N-(3-Fluoropiperidin-4-yl)-1-(4-chlorobenzyl)-4-fluoro-1H-indole-3-carboxamide (Isomer-I) | $^1$H- NMR (DMSO-d$_6$, 400 MHz) δ ppm: 1.61-1.62 (m, 2H), 2.58 (bs, 1H), 2.91-2.92 (m, 2H), 3.11 (m, 2H), 4.04-4.15 (m, 1H), 4.59-4.72 (d, 1H), 5.50 (s, 2H), 6.93-6.98 (m, 1H), 7.15-7.20 (m, 1H), 7.26-7.28 (d, J = 8.3 Hz, 2H), 7.36-7.40 (t, 3H), 7.65-7.69 (t, 1H), 8.18 (s, 1H); Mass (m/z): 404.2 (M + H)$^+$. |

| Example No. | Chemical name and Structure | Characterization data |
|---|---|---|
| 59 | 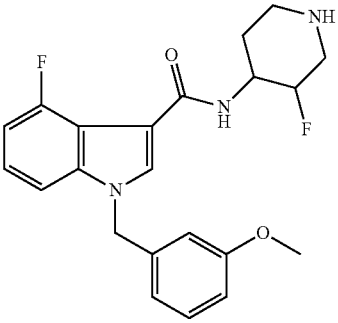<br>cis,-N-(3-Fluoropiperidin-4-yl)-4-fluoro-1-(3-methoxybenzyl)-1H-indole-3-carboxamide (Isomer-I) | $^1$H - NMR (DMSO-d$_6$, 400 MHz) δ ppm: 1.63 (m, 2H), 2.58 (bs, 1H), 2.67 (m, 1H), 2.81 (m, 1H), 2.92-2.95 (m, 1H), 3.11 (m, 1H), 3.70 (s, 3H), 4.05 (m, 1H), 4.59-4.72 (d, 1H), 5.45 (s, 2H), 6.77-6.79 (d, J = 7.3 Hz, 1H), 6.83-6.86 (m, 2H), 6.93-6.98 (m, 1H), 7.15-7.25 (m, 2H), 7.39-7.41 (d, J = 8.1 Hz, 1H), 7.63-7.67 (t, 1H), 8.16 (s, 1H); Mass (m/z): 400.3 (M + H)$^+$. |
| 60 | 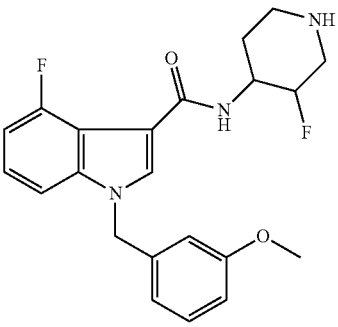<br>cis-N-(3-Fluoropiperidin-4-yl)-4-fluoro-1-(3-methoxybenzyl)-1H-indole-3-carboxamide (Isomer-II) | $^1$H - NMR (DMSO-d$_6$, 400 MHz) δ ppm: 1.63-1.68 (m, 2H), 2.59 (bs, 1H), 2.82 (m, 1H), 2.92-2.99 (m, 1H), 3.09-3.15 (m, 2H), 3.70 (s, 3H), 4.02-4.05 (m, 1H), 4.59-4.71 (d, 1H), 5.45 (s, 2H), 6.76-6.95 (m, 4H), 7.16-7.25 (m, 2H), 7.39-7.41 (d, J = 8.3 Hz, 1H), 7.64-7.68 (t, 1H), 8.16 (s, 1H); Mass (m/z): 400.2 (M + H)$^+$. |
| 61 | 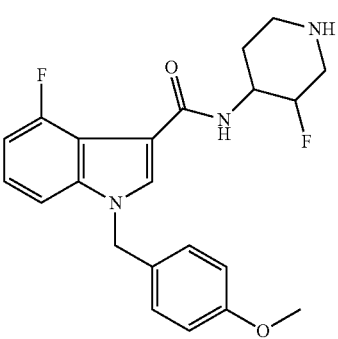<br>cis-N-(3-Fluoropiperidin-4-yl)-1-(4-methoxybenzyl)-4-fluoro-1H-indole-3-carboxamide (Isomer-II) | $^1$H - NMR (CDCl$_3$, 400 MHz) δ ppm: 1.72-1.80 (m, 1H), 1.85-1.90 (m, 1H), 2.72-2.80 (m, 1H), 2.82-2.91 (bs, 1H), 2.90-2.94 (d, 1H), 3.14-3.17 (m, 1H), 3.33-3.39 (m, 1H), 3.70 (s, 3H), 4.29-4.36 (m, 1H), 4.67-4.78 (d, 1H), 5.25 (s, 2H), 6.83-6.86 (d, J = 8.5 Hz, 2H), 6.93-6.96 (m, 1H), 7.09-7.11 (d, J = 8.4 Hz, 2H), 7.24 (m, 2H), 7.44-7.51 (m, 1H), 7.95 (s, 1H); Mass (m/z): 400.4 (M + H)$^+$ |

| Example No. | Chemical name and Structure | Characterization data |
|---|---|---|
| 62 | 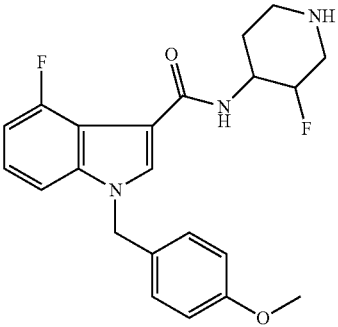<br>cis-N-(3-Fluoropiperidin-4-yl)-1-(4-methoxybenzyl)-4-fluoro-1H-indole-3-carboxamide (Isomer-I) | $^1$H - NMR (CDCl$_3$, 400 MHz) δ ppm: 1.72-1.80 (m, 1H), 1.87-1.91 (m, 1H), 2.72-2.80 (m, 1H), 2.82-2.91 (bs, 1H), 2.90-2.94 (d, 1H), 3.14-3.17 (m, 1H), 3.33-3.39 (m, 1H), 3.70 (s, 3H), 4.28-4.36 (m, 1H), 4.67-4.79 (d, 1H), 5.25 (s, 2H), 6.83-6.85 (d, J = 8.5 Hz, 2H), 6.92-6.96 (m, 1H), 7.09-.11 (d, J = 8.4 Hz, 2H), 7.23-7.24 (m, 2H), 7.44-7.51 (m, 1H), 7.95 (s, 1H); Mass (m/z): 400.4 (M + H)$^+$. |
| 63 | 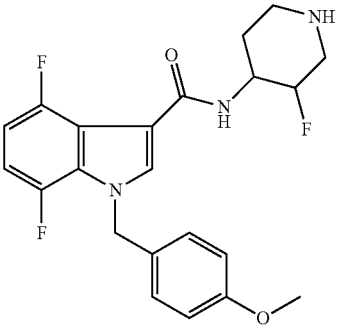<br>cis-N-(3-Fluoropiperidin-4-yl)-1-(4-methoxybenzyl)-4,7-difluoro-1H-indole-3-carboxamide (Isomer-I) | $^1$H - NMR (DMSO-d$_6$, 400 MHz) δ ppm: 1.59-1.67 (m, 2H), 1.93-2.00 (m, 1H), 2.55-2.58 (m, 1H), 2.65-2.85 (m, 1H), 2.92-2.95 (m, 1H), 3.05-3.15 (m, 1H), 3.70 (s, 3H), 4.03-4.11 (m, 1H), 4.59-4.71 (m, 1H), 5.46 (s, 2H), 6.85-6.91 (m, 3H), 6.97-7.03 (m, 1H), 7.14-7.17 (d, J = 8.4 Hz, 2H), 7.75-7.79 (m, 1H), 8.13 (s, 1H); Mass (m/z): 418.3 (M + H)$^+$. |
| 64 | 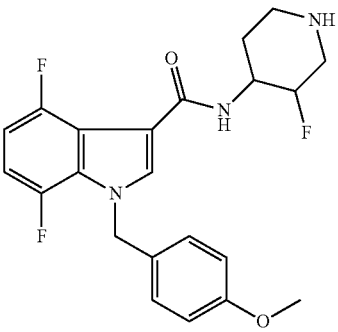<br>cis-N-(3-Fluoropiperidin-4-yl)-1-(4-methoxybenzyl)-4,7-difluoro-1H-indole-3-carboxamide (Isomer-II) | $^1$H - NMR (DMSO-d$_6$, 400 MHz) δ ppm: 1.59-1.67 (m, 2H), 1.93-2.00 (m, 1H), 2.55-2.58 (m, 1H), 2.65-2.85 (m, 1H), 2.92-2.95 (m, 1H), 3.07-3.13 (m, 1H), 3.70 (s, 3H), 4.03-4.11 (m, 1H), 4.59-4.71 (m, 1H), 5.46 (s, 2H), 6.88-6.90 (m, 3H), 6.97-7.03 (m, 1H), 7.15-7.17 (d, J = 8.3 Hz, 2H), 7.76-7.80 (m, 1H), 8.14 (s, 1H); Mass (m/z): 418.3 (M + H)$^+$. |

| Example No. | Chemical name and Structure | Characterization data |
|---|---|---|
| 65 | 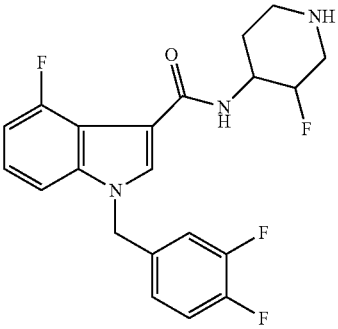<br>cis-N-(3-Fluoropiperidin-4-yl)-1-(3,4-difluorobenzyl)-4-fluoro-1H-indole-3-carboxamide (Isomer-I) | $^1$H - NMR (DMSO-d$_6$, 400 MHz) δ ppm: 1.63-1.66 (m, 2H), 2.62 (m, 1H), 2.67-2.71 (m, 1H), 2.77-2.81 (m, 1H), 2.92-2.95 (m, 1H), 3.08-3.15 (m, 1H), 4.05-4.12 (m, 1H), 4.59-4.72 (d, 1H), 5.48 (s, 2H), 6.93-6.98 (m, 1H), 7.12 (s, 1H), 7.16-7.22 (m, 1H), 7.36-7.45 (m, 3H), 7.66-7.71 (t, 1H), 8.19 (s, 1H); Mass (m/z): 406.3 (M + H)$^+$. |
| 66 | 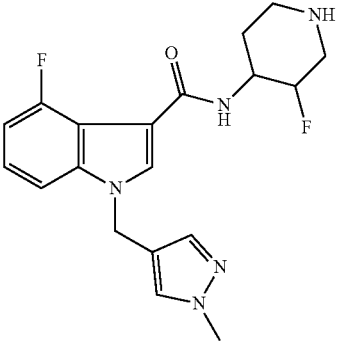<br>cis-N-(3-Fluoropiperidin-4-yl)-1-(1-methyl-1H-pyrazol-4yl-methyl)-4-fluoro-1H-indole-3-carboxamide (Isomer-I) | $^1$H - NMR (DMSO-d$_6$, 400 MHz) δ ppm: 1.61-1.63 (m, 2H), 2.55 (bs, 1H), 2.56-2.58 (m, 1H), 2.67-2.68 (m, 1H), 2.92-2.95 (m, 1H), 3.12 (m, 1H), 3.75 (s, 3H), 4.04 (m, 1H), 4.59-4.71 (d, 1H), 5.29 (s, 2H), 6.93-6.98 (m, 1H), 7.18-7.23 (m, 1H), 7.46 (s, 1H), 7.51-7.53 (d, J = 8.2 Hz, 1H), 7.56-7.61 (t, 1H), 7.71 (s, 1H), 8.07 (s, 1H); Mass (m/z): 374.4 (M + H)$^+$. |
| 67 | 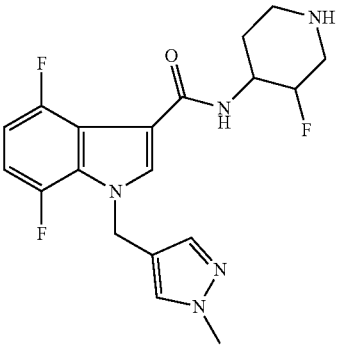<br>cis-N-(3-Fluoropiperidin-4-yl)-1-(1-methyl-1H-pyrazol-4yl-methyl)-4,7-difluoro-1H-indole-3-carboxamide (Isomer-I) | $^1$H - NMR (DMSO-d$_6$, 400 MHz) δ ppm: 1.61-1.63 (m, 2H), 2.55 (bs, 1H), 2.67-2.70 (m, 1H), 2.76-2.80 (m, 1H), 2.92-2.95 (m, 1H), 3.08-3.14 (m, 1H), 3.76 (s, 3H), 4.03-4.10 (m, 1H), 4.58-4.70 (d, 1H), 5.36 (s, 2H), 6.86-6.91 (m, 1H), 7.01-7.07 (m, 1H), 7.41 (s, 1H), 7.66 (s, 1H), 7.72-7.74 (t, 1H), 8.07 (s, 1H); Mass (m/z): 392.2 (M + H)$^+$. |

| Example No. | Chemical name and Structure | Characterization data |
|---|---|---|
| 68 | 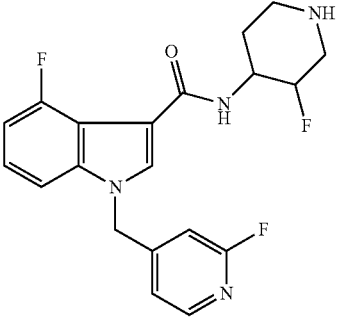<br>cis-N-(3-Fluoropiperidin-4-yl)-1-(2-fluoropyridin-4-ylmethyl)-4-fluoro-1H-indole-3-carboxamide | $^1$H - NMR (CDCl$_3$, 400 MHz) δ ppm: 1.72-1.78 (m, 1H), 1.89-1.97 (m, 1H), 2.73-2.81 (m, 1H), 2.83-2.91 (bs, 1H), 2.91-2.95 (d, 1H), 3.11-3.18 (m, 1H), 3.34-3.41 (m, 1H), 4.30-4.37 (m, 1H), 4.68-4.81 (d, 1H), 5.17 (s, 2H), 6.88-6.98 (m, 2H), 7.00-7.05 (m, 1H), 7.20-7.22 (m, 3H), 7.45-7.52 (m, 1H), 7.97 (s, 1H); Mass (m/z): 389.3 (M + H)$^+$. |
| 69 | 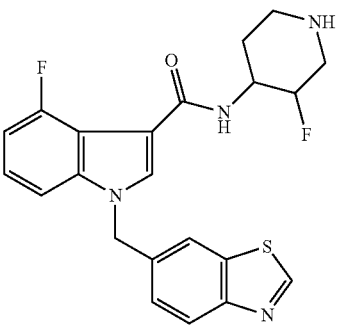<br>cis-N-(3-Fluoropiperidin-4-yl)-1-(benzothiazol-6-ylmethyl)-4-fluoro-1H-indole-3-carboxamide (Isomer-I) | $^1$H - NMR (DMSO-d$_6$, 400 MHz) δ ppm: 1.63-1.68 (m, 2H), 2.57 (bs, 1H), 2.80 (m, 1H), 2.92-2.96 (m, 1H), 3.08-3.15 (m, 2H), 4.04-4.15 (m, 1H), 4.57-4.71 (d, 1H), 5.46 (s, 2H), 6.91-6.95 (m, 1H), 7.15-7.20 (m, 1H), 7.44-7.46 (d, J = 8.3 Hz, 2H), 7.64 (t, 1H), 8.04-8.08 (m, 2H), 8.21 (s, 1H), 8.61-8.63 (m, 1H); Mass (m/z): 427.1 (M + H)$^+$. |
| 70 | 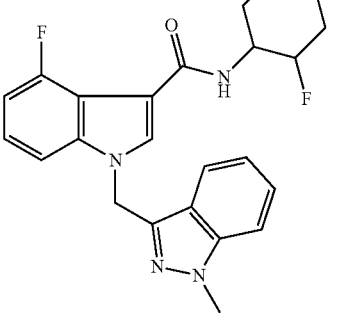<br>Cis-N-(3-Fluoropiperidin-4-yl)-1-(1-methyl-1H-indazole-3-ylmethyl)-4-fluoro-1H-indole-3-carboxamide (Isomer-I) | $^1$H - NMR (DMSO-d$_6$, 400 MHz) δ ppm: 1.45-1.47 (m, 1H), 1.95-1.98 (m, 1H), 2.44-2.49 (m, 1H), 2.54-2.59 (m, 2H), 2.83-2.86 1H), 3.16-3.20 (m, 1H), 3.83 (s, 3H), 4.10-4.12 (m, 1H), 4.35-4.49 (m, 1H), 5.56 (s, 2H), 7.26-7.37 (m, 3H), 7.43-7.46 (m, 1H), 7.88 (s, 1H), 8.08-8.10 (m, 1H), 8.16 (s, 1H), 8.50-8.52 (m, 1H), 8.84-8.86 (m, 1H); Mass (m/z): 424.2 (M + H)$^+$. |

| Example No. | Chemical name and Structure | Characterization data |
|---|---|---|
| 71 | cis-N-(3-Fluoropiperidin-4-yl)-1-(2-fluoropyridin-4-ylmethyl)-4,7-difluoro-1H-indole-3-carboxamide (Isomer-I) | $^1$H - NMR (DMSO-$d_6$, 400 MHz) δ ppm: 1.62-1.68 (m, 1H), 2.51-2.56 (m, 2H), 2.67-2.71 (m, 1H), 2.93-2.96 (m, 1H), 3.08-3.14 (m, 1H), 4.05-4.13 (m, 1H), 4.05-4.13 (m, 1H), 4.60-4.72 (d, 1H), 5.67 (s, 2H), 6.87-6.94 (m, 2H), 6.97-7.03 (m, 2H), 7.87-7.91 (t, 1H), 8.16 (s, 1H), 8.18-8.19 (d, J = 5.1 Hz, 1H); Mass (m/z): 407.2 M + H)$^+$. |

Biological Data

Example 72

Determination of Allosteric Potency $EC_{50}$ Values for Muscarinic M1 Receptor:

A stable CHO cell line expressing recombinant human Muscarinic M1 receptor and pCRE-Luc reporter system was used for cell-based assay. The assay offers a non-radioactive based approach to determine binding of a compound to GPCRs. In this specific assay, the level of intracellular cyclic AMP which is modulated by activation or inhibition of the receptor is measured. The recombinant cells harbor luciferase reporter gene under the control of cAMP response element.

The above cells were grown in 96 well clear bottom white plates in Hams F12 medium containing 10% fetal bovine serum (FBS). Prior to the addition of compounds or standard agonist, cells were serum starved overnight. Increasing concentrations of test compounds were added along with $EC_{20}$ of acetylcholine in OptiMEM medium to the cells. The incubation was continued at 37° C. in $CO_2$ incubator for 4 hours. Medium was removed and cells were washed with phosphate buffered saline. The cells were lysed and luciferase activity was measured in a Luminometer. Luminescence units were plotted against the compound concentrations using Graphpad software. $EC_{50}$ values of the compounds were defined as the concentration required in stimulating the luciferase activity by 50% in presence of $EC_{20}$ of acetylcholine and the results are provided in table 1.

TABLE 1

| Ex. | hM1 PAM $EC_{50}$ (nM) |
|---|---|
| 1 | 1264 |
| 2 | 681.1 |
| 3 | 1637 |
| 4 | 1492 |
| 5 | 370.5 |
| 6 | 122.5 |
| 7 | 1360 |
| 8 | 192 |

TABLE 1-continued

| Ex. | hM1 PAM $EC_{50}$ (nM) |
|---|---|
| 9 | 1417 |
| 10 | 940 |
| 11 | 1534 |
| 12 | 432.5 |
| 13 | 1378 |
| 18 | 160.2 |
| 19 | 744 |
| 22 | 1495 |
| 23 | 1074 |
| 24 | 1390 |
| 25 | 1441 |
| 26 | 1105 |
| 27 | 1689 |
| 28 | 1568 |
| 29 | 2920 |
| 30 | 1081 |
| 31 | 1608 |
| 32 | 1586 |
| 33 | 1374 |
| 34 | 1387 |
| 35 | 1482 |
| 36 | 1349 |
| 37 | 1985 |
| 38 | 1448 |
| 39 | 1485 |
| 44 | 1306 |
| 45 | 1163 |

Example 73

Protein Binding Assay

Unbound fractions of new chemical entities in plasma, brain homogenate and liver microsomes were determined using high-throughput dialysis (HT dialysis). Briefly, dialysis membranes were soaked in deionized water for 20 minutes and then in deionized water with 30% ethanol for 15 minutes and finally in phosphate buffer until use. Membranes were rinsed in phosphate buffer before assembling. The membranes were layered between teflon bars of dialysis assembly. Stock solutions of test compounds were prepared at 10 mM in DMSO, diluted to 1 mM in acetonitrile and further diluted to 100 μM in mixture of water and acetonitrile (1:1 v/v). Human plasma (pool of 3) was prepared from human blood (3 donors) by centrifuging at 4000 rpm for 10 min at 4° C. Rat and dog blood were obtained on the day of the study and centrifuged to obtain plasma. Rat brains were isolated, cleaned and homogenized with 2 volumes of buffer (3 fold dilution). Liver microsomes were prepared at 0.5 mg/mL in phosphate buffer (100 mM, pH 7.4). The dialysate chambers were loaded with 150 µL of 100 mM phosphate buffer (pH 7.4) in triplicates. The matrix chambers were loaded with 150 µL of the plasma or brain homogenate or microsomal suspension spiked with test compounds at a final concentration of 1 µM. 50 µL of the sample was removed from both the chambers at 0 h. The plate was sealed and incubated at 37° C. for 6 h at 100 rpm. After 6 h, 50 µL of the sample was removed from both the chambers. Equal volumes of buffer or human plasma/microsomal suspension were added to the plasma/microsomal and buffer samples respectively to create identical sample matrices for analysis. The samples were precipitated with 150 µL of acetonitrile containing fluoxetine as an internal standard. All the samples were centrifuged at 10000 rpm for 10 minutes at 4° C. The supernatants were analyzed by LC-MS/MS and the results are provided in table 2.

TABLE 2

| | | Fu (Mean ± SEM, n = 3) | | |
|---|---|---|---|---|
| Ex. | Species | Plasma | Brain | Microsomes |
| 1 | Rat | 0.267 ± 0.03 | 0.166 ± 0.01 | 0.836 ± 0.04 |
| | Dog | 0.217 ± 0.21 | NA | 0.982 ± 0.01 |
| | Human | 0.197 ± 0.01 | NA | 1.046 ± 0.07 |
| 2 | Rat | 0.068 ± 0.002 | 0.015 ± 0.001 | 0.679 ± 0.081 |
| | Dog | 0.087 ± 0.008 | NA | 0.576 ± 0.079 |
| | Human | 0.040 ± 0.002 | NA | 0.459 ± 0.046 |
| 5 | Rat | 0.210 ± 0.01 | 0.128 ± 0.01 | 0.779 ± 0.01 |
| | Dog | 0.163 ± 0.02 | NA | 0.746 ± 0.004 |
| | Human | 0.077 ± 0.01 | NA | 0.899 ± 0.03 |
| 6 | Rat | 0.050 ± 0.008 | 0.014 ± 0.001 | 0.560 ± 0.048 |
| | Dog | 0.043 ± 0.002 | NA | 0.713 ± 0.041 |
| | Human | 0.030 ± 0.003 | NA | 0.546 ± 0.018 |
| 7 | Rat | 0.20 ± 0.02 | 0.06 ± 0.004 | 0.80 ± 0.04 |
| | Dog | 0.20 ± 0.01 | NA | 0.60 ± 0.03 |
| | Human | 0.10 ± 0.004 | NA | 0.70 ± 0.03 |

TABLE 2-continued

| | | Fu (Mean ± SEM, n = 3) | | |
|---|---|---|---|---|
| Ex. | Species | Plasma | Brain | Microsomes |
| 8 | Rat | 0.089 ± 0.01 | 0.0348 ± 0.0001 | 0.606 ± 0.008 |
| | Dog | 0.064 ± 0.01 | NA | 0.679 ± 0.066 |
| | Human | 0.079 ± 0.006 | NA | 0.626 ± 0.037 |
| 22 | Rat | 0.315 ± 0.03 | 0.067 ± 0.002 | 0.902 ± 0.006 |
| | Dog | 0.310 ± 0.01 | NA | 0.866 ± 0.034 |
| | Human | 0.309 ± 0.008 | NA | 0.788 ± 0.031 |

Example 74

Rodent Pharmacokinetic Study

Male Wistar rats (260±50 grams) were used as experimental animals. Animals were housed individually in polypropylene cage. Two days prior to study, male Wistar rats were anesthetized with isoflurane for surgical placement of jugular vein catheter. Rats were randomly divided for oral (3 mg/kg) and intravenous (i.v.) (1 mg/kg) dosing (n=3/group) and fasted overnight before oral dosing (p.o.). However, rats allocated to intravenous dosing food and water was provided ad libitum.

At pre-determined point, blood was collected through jugular vein and replenished with an equivalent volume of normal saline. Collected blood was transferred into a labeled eppendorf tube containing 10 µL of heparin as an anticoagulant. Typically blood samples were collected at following time points: 0.08, 0.25, 0.5, 1, 2, 4, 6, 8, and 24 hours post dose. Blood was centrifuged at 4000 rpm for 10 minutes. Plasma was separated and stored frozen at −80° C. until analysis. The concentrations of the test compounds were quantified in plasma by qualified LC-MS/MS method using suitable extraction technique. The test compounds were quantified in the calibration range around 1-1000 ng/mL in plasma. Study samples were analyzed using calibration samples in the batch and quality control samples spread across the batch.

Pharmacokinetic parameters $C_{max}$, $AUC_t$, $T_{1/2}$, Clearance, and Bioavailability (% F) were calculated by non-compartmental model using standard non-compartmental model by using Phoenix WinNonlin 6.0.2 or 6.0.3 version Software package and the results are tabulated in table 3.

TABLE 3

| Ex. | ROA | Vehicle | $C_{max}$ (ng/mL) | $AUC_{0-t}$ (ng · hr/mL) | $T_{1/2}$ (hr) | Clearance (mL/min/kg) | % F |
|---|---|---|---|---|---|---|---|
| 1 | oral | 0.25% Tween 80 + 99.75% HEC solution | 1187 ± 81 | 5163 ± 464 | 2.9 ± 0.2 | — | 76 ± 7 |
| | i.v | 5% Pharmasolve + 45% Propylene glycol + 50% PEG 400 | — | 2250 ± 190 | 3.0 ± 0.3 | 7.3 ± 0.4 | |
| 2 | oral | 0.25% Tween 80 + 99.75% HEC solution | 632 ± 167 | 2161 ± 599 | 1.9 ± 0.2 | — | 63 ± 17 |
| | i.v | 5% Pharmasolve + 45% Propylene glycol + 50% PEG 400 | — | 1146 ± 245 | 1.9 ± 0.4 | 16.1 ± 2.8 | |
| 5 | oral | 0.25% Tween 80 + 99.75% HEC solution | 2681 ± 664 | 7867 ± 2857 | 3.3 ± 0.3 | — | 90 ± 33 |
| | i.v | 5% Pharmasolve + 45% Propylene glycol + 50% PEG 400 | — | 2921 ± 1432 | 4.0 ± 1.7 | 7.1 ± 4.3 | |
| 7 | oral | 0.25% Tween 80 + 99.75% HEC solution | 783 ± 254 | 2261 ± 471 | 1.4 ± 0.2 | — | 67 ± 14 |
| | i.v | 5% Pharmasolve + 45% Propylene glycol + 50% PEG 400 | — | 1119 ± 119 | 2.0 ± 0.4 | 14.2 ± 2.0 | |
| 8 | oral | 0.25% Tween 80 + 99.75% HEC solution | 578 ± 170 | 2497 ± 842 | 2.3 ± 1.8 | — | 45 ± 15 |

TABLE 3-continued

| Ex. | ROA | Vehicle | $C_{max}$ (ng/mL) | $AUC_{0-t}$ (ng · hr/mL) | $T_{1/2}$ (hr) | Clearance (mL/min/kg) | % F |
|---|---|---|---|---|---|---|---|
|  | i.v | 5% Pharmasolve + 45% Propylene glycol + 50% PEG 400 | — | 1834 ± 562 | 1.8 ± 0.3 | 9 ± 3 |  |
| 12 | oral | 0.25% Tween 80 + 99.75% HEC solution | 337 ± 141 | 1140 ± 114 | 3.0 ± 3.0 | — | 62 ± 6 |
|  | i.v | 5% Pharmasolve + 45% Propylene glycol + 50% PEG 400 | — | 609 ± 62 | 1.6 ± 0.5 | 26.7 ± 3.4 |  |
| 22 | oral | Reagent grade water | 207 ± 76 | 1647 ± 147 | 4.8 ± 2.8 | — | 60 ± 5 |
|  | i.v | Water for injection | — | 908 ± 198 | 7.6 ± 1.7 | 17.1 ± 3.3 |  |

ROA—Route of Administration

Example 75

Rodent Brain Penetration Study

Male Wistar rats (260±40 grams) were used as experimental animals. Three animals were housed in each cage. Animals were given water and food ad libitum throughout the experiment and maintained on a 12 hours light/dark cycle.

Brain penetration was determined in discrete manner in rats. One day prior to dosing day, male Wistar rats were acclimatized and randomly grouped according to their weight. At each time point (0.5, 1 and 2 hours) n=3 animals were used.

The test compounds were suitably preformulated and administered orally at (free base equivalent) 3 mg/kg. Blood samples were removed via cardiac puncture by using isoflurane anesthesia. The animals were sacrificed to collect brain tissue. Plasma was separated and brain samples were homogenized and stored frozen at ~20° C. until analysis. The concentrations of the test compounds in plasma and brain were determined using LC-MS/MS method.

The test compounds were quantified in plasma and brain homogenate by qualified LC-MS/MS method using suitable extraction technique. The test compounds were quantified in the calibration range of 1-500 ng/mL in plasma and brain homogenate. Study samples were analyzed using calibration samples in the batch and quality control samples spread across the batch. Extent of brain-plasma ratio was calculated (Cb/Cp) and the results are tabulated in table 4.

TABLE 4

| Ex. | Single dose Rat Brain Penetration (Cb/Cp) at 3 mg/kg, p.o. |
|---|---|
| 1 | 0.30 ± 0.05 |
| 2 | 0.95 ± 0.17 |
| 5 | 0.50 ± 0.04 |
| 6 | 2.09 ± 0.46 |
| 7 | 0.61 ± 0.01 |
| 8 | 1.1 ± 0.1 |
| 10 | 2.40 ± 0.30 |
| 11 | 1.59 ± 0.35 |
| 12 | 1.64 ± 0.12 |
| 22 | 0.46 ± 0.11 |
| 30 | 1.05 ± 0.53 |
| 35 | 0.72 ± 0.03 |
| 38 | 1.03 ± 0.17 |

Example 76

Object Recognition Task Model

The cognition enhancing properties of compounds of this invention were estimated by using this model.

Male Wistar rats (8-10 weeks old) were used as experimental animals. Four animals were housed in each cage. Animals were kept on 20% food deprivation from a day prior to experimentation. Water was provided ad libitum throughout the experiment. Animals were maintained on a 12 hours light/dark cycle in temperature and humidity controlled room. The experiment was carried out in an open field made up of acrylic. Rats were habituated to individual arenas (open field) for 1 hour in the absence of any objects on day 1.

One group of 12 rats received vehicle and another set of animals received compound of the formula (I), before the familiar ($T_1$) and choice ($T_2$) trials. During the familiarization phase, ($T_1$), the rats were placed individually in the arena for 3 minutes, in which two identical objects ($a_1$ and $a_2$) were positioned 10 cm from the wall. 24 hours after $T_1$, trial for long-term memory test was performed. The same rats were placed in the same arena as they were placed in $T_1$ trial. During the choice phase ($T_2$) rats were allowed to explore the arena for 3 minutes in presence of a copy of familiar object ($a_3$) and one novel object (b). During the $T_1$ and $T_2$ trial, explorations of each object (defined as sniffing, licking, chewing or having moving vibrissae whilst directing the nose towards the object at a distance of less than 1 cm) were recorded using stopwatch.

$T_1$ is the total time spent exploring the familiar objects (a1+a2).

$T_2$ is the total time spent exploring the familiar object and novel object (a3+b).

Discriminative index=Time spent with novel object/(time spent with novel and familiar object).

The object recognition test was performed as described by *Behavioural Brain Research,* 1988, 31, 47-59 and the results are provided in table 5.

TABLE 5

| | Dose mg/kg, | Exploration time mean ± S.E.M (sec) | | |
|---|---|---|---|---|
| Ex. | p.o. | Familiar object | Novel object | Inference |
| 1 | 0.3 | 11.31 ± 1.07 | 28.92 ± 3.54 | Active |
| 2 | 1 | 9.06 ± 1.75 | 15.09 ± 2.19 | Active |
| 5 | 0.3 | 11.00 ± 0.81 | 19.64 ± 1.74 | Active |
| 6 | 3 | 15.75 ± 1.71 | 23.67 ± 2.62 | Active |
| 7 | 1 | 9.16 ± 0.83 | 19.56 ± 1.96 | Active |
| 8 | 0.3 | 7.59 ± 1.02 | 14.36 ± 1.56 | Active |
| 22 | 3 | 8.21 ± 0.70 | 15.72 ± 2.25 | Active |

Example 77

Object Recognition Task Model—Scopolamine challenge

The cognition enhancing properties of compounds of this invention were estimated by using this model.

Male Wistar rats (8-10 weeks old) were used as experimental animals. Four animals were housed in each cage. Animals were kept on 20% food deprivation from a day prior to experimentation. Water was provided ad libitum throughout the experiment. Animals were maintained on a 12 hours light/dark cycle in temperature and humidity controlled room. The experiment was carried out in an open field made up of acrylic. Rats were habituated to individual arenas (open field) for 1 hour in the absence of any objects on day 1.

Rats received vehicle or vehicle and scopolamine or compound of the formula (I) and scopolamine, before the familiar ($T_1$). During the familiarization phase, ($T_1$), the rats were placed individually in the arena for 3 minutes, in which two identical objects ($a_1$ and $a_2$) were positioned 10 cm from the wall. 3 minutes after $T_1$, trial for memory test was performed. The same rats were placed in the same arena as they were placed in $T_1$ trial. During the choice phase ($T_2$) rats were allowed to explore the arena for 3 minutes in presence of a copy of familiar object ($a_3$) and one novel object (b). During the $T_1$ and $T_2$ trial, explorations of each object (defined as sniffing, licking, chewing or having moving vibrissae whilst directing the nose towards the object at a distance of less than 1 cm) were recorded using stopwatch.

$T_1$ is the total time spent exploring the familiar objects (a1+a2).

$T_2$ is the total time spent exploring the familiar object and novel object (a3+b).

Discriminative index=Time spent with novel object/(time spent with novel and familiar object).

TABLE 6

| Ex. | Dose mg/kg, p.o. | Exploration time mean ± S.E.M (sec) | | |
|---|---|---|---|---|
| | | Familiar object | Novel object | Inference |
| 1 | 0.3 | 7.54 ± 1.93 | 13.07 ± 1.79 | Active |
| 2 | 0.3 | 14.29 ± 1.92 | 20.93 ± 2.89 | Active |
| 5 | 1 | 13.61 ± 1.79 | 25.72 ± 3.67 | Active |
| 22 | 1 | 21.34 ± 3.65 | 29.70 ± 1.72 | Active |

Example 78

Contextual Fear Conditioning Task

Experiment was carried out over a period of two days. On day 1, rats were placed in the operant behavior chamber and allowed to acclimatize for 2 minutes. Rats received an unavoidable foot shock (unconditioned stimulus (US): electric shock of 0.5-0.7 mA for 3 seconds). Following a 1 minute interval, shocks were repeated to deliver a total of three US. Rats were administered Vehicle or test compound post training Scopolamine (0.3 mg/kg, s.c.) was administered 120 minutes after training On day 2, rats were placed in the operant behavior chamber and total freezing time was scored for a period of 5 minutes. The results are provided in the FIG. 1.

Example 79

Estimation of Cortical sAPPα Levels in Rat Brain

Experimental Procedure:

Male Wistar rats (250±45 grams) were randomly divided into different treatment groups (n=5 per group). Control group of rats were administered with intraperitoneal (i.p.) injection of vehicle (99.75% of 0.25% hydroxyethylcellulose HHX+0.25% tween 80 for examples 8 and 22; 5% Pharmasolve+45% propylene glycol+50% polyethylene glycol-400 for example 1). Rats in treatment groups were allocated to one dose of test compound and administered with a single intraperitoneal injection of test compound (dose volume of 2 mL/kg). Rats were sacrificed by cervical dislocation at 60 minutes after treatment. Brains were quickly isolated and the cortex was dissected out at −20° C. The cortex was immediately kept on a dry ice and weighed before being stored at −80° C. until quantification of sAPPα using Enzyme-linked immunosorbent assay (ELISA).

Sample Preparation:
1. Protease inhibitor cocktail tablets (complete mini, Make-Roche; 1 tablet for 8 mL) were added to the Tris Buffer Saline (TBS) prior to using the buffer for tissue processing.
2. Cortical tissues were thawed and homogenized in five volumes of TBS and the solution was centrifuged at 15,000 rpm at 4° C. for 90 minutes.
3. The supernatant was discarded and homogenized in five volumes of TBS. Samples were centrifuged at 15,000 rpm at 4° C. for 30 minutes.
4. Supernatant was discarded and precipitate was sonicated in ten volumes of 50 mM Tris buffer (pH: 7.6) containing 6 M of Guanidine-HCl. Sonication was repeated four times with duration of five seconds every time.
5. Resulting mixture was incubated at the room temperature for 30 minutes and centrifuged at 15,000 rpm at 4° C. for 30 minutes. Supernatant was diluted 100 times with EIA buffer prior to addition in the pre-coated ELISA plates.

Measurement of sAPPα by ELISA Kit:

To investigate the role of an acute treatment of test compound on sAPPα levels, the expression of this protein was measured in samples obtained from brain homogenates of treated and untreated rats by employing ELISA assay. The entire procedure was followed as described in the ELISA kit manual (Mouse/Rat sAPPα (highly sensitive) assay kit, Catalog Number: JP27419, Immuno-Biological Laboratories Co. Ltd, Hamburg, Germany).

Statistical Analysis:

Statistical analyses were performed using the Graph Pad Prism (Version 4). Results are expressed as Mean±SEM levels of sAPPα expressed as percentage of control values obtained from rats treated with vehicle. Statistical significance after treatment was assessed using One-Way ANOVA followed by Dunnett's post test and the significance level was set below p value less than 0.05 and the results are tabulated in table 7.

TABLE 7

Effect of test compounds on cortical sAPPα levels in male Wistar rats.

| | sAPPα levels (% of vehicle) | | | |
|---|---|---|---|---|
| Ex. | 1.0 mg/kg, i.p. | 3.0 mg/kg, i.p. | 10.0 mg/kg, i.p. | Inference |
| 1 | 155 ± 6** | 153 ± 7** | 142 ± 6** | Active |
| 8 | 120 ± 17 | 137 ± 14 | 173 ± 10** | Active |
| 22 | 143 ± 14 | 164 ± 12** | 176 ± 10** | Active |

Values are mean ± SEM (n = 5/group).
**p < 0.01 Vs Vehicle (Dunnett's post test).

Example 80

Modulation of Cerebral Blood Flow in Frontal Cortex:

The effect of test compound on modulation of cerebral blood flow was evaluated using rats.

Rats were acclimatized to the laboratory environment for at least 7 days. Rats (300-350 grams) were housed in a group of four in a controlled environment (Temp=21±3° C.; Humidity=30-70%) and maintained on a 12-hour light/dark cycle with lights on at 07:00 AM. Food and water was provided ad libitum.

Rats were anaesthetized with 12% urethane (i.p.). Animal's body core temperature was maintained at 37° C. via heating pad and rectal temperature probe. A small incision was made at one of the ventral side of the hind limb and the femoral vein was cannulated with PE10 tubing for drug application. Then animal was placed into a stereotaxic frame and a midline incision was made to expose the skull. A burr hole was drilled over the frontal cortex (stereotaxic coordinates 1 mm anterior and 4 mm lateral to bregma). Oxygen was supplied through the nose cone of the seterotaxic apparatus which was connected to the controlled gaseous supplier with a flow of 200 mL/minute. Laser Doppler probe (AD Instruments Inc) was placed over the hole to monitor cerebral blood flow. The Laser Doppler probe was connected to a computerized data acquisition system (PowerLab 16/30, AD Instruments Inc). Vehicle or test compound was administered intravenously after cerebral blood flow was stable for 30 minutes. The cerebral blood flow was collected for further 90 minutes. Data obtained was calculated as percent increase relative to resting basal blood flow level. Test compound data was compared with the control group using one-way ANOVA followed by the Bonferroni post test.

REFERENCE

*Psychopharmacology (Berl).* 2013, 225, 21-30.
Result:
Example 1 significantly increased the cerebral blood flow as shown in FIG. 2.

We claim:
1. A fluoroindole compound of formula (I),

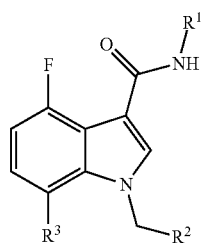

(I)

wherein:
$R^1$ is

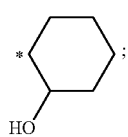

$R^2$

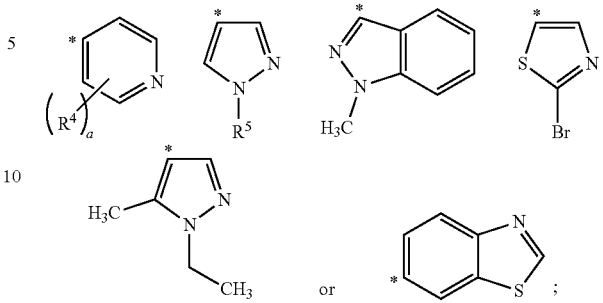

wherein * represents point of attachment;
$R^3$ is fluorine or hydrogen;
$R^4$ is halogen, S—$CH_3$ or hydrogen;
$R^5$ is halogen, —O—$CH_3$, $CONH_2$, $CONHCH_3$, or hydrogen; and
a is 1 or 2;
or an isotopic form, a stereoisomer or a pharmaceutically acceptable salt thereof.

2. The compound as claimed in claim 1, wherein:
$R^1$ is

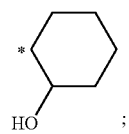

and
$R^2$ is

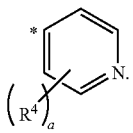

3. The compound as claimed in claim 1, wherein:
$R^1$ is

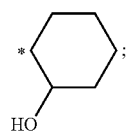

and
$R^2$ is

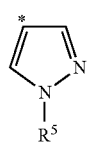

4. The compound as claimed in claim 1, wherein the compound is selected from the group consisting of:

N-[(1S,2S)-2-Hydroxycyclohexyl]-1-(1-methyl-1H-pyrazol-4-ylmethyl)-4-fluoro-1H-indole-3-carboxamide;
N-[(1S,2S)-2-Hydroxycyclohexyl]-1-(2-Chloropyridin-4-ylmethyl)-4-fluoro-1H-indole-3-carboxamide;
N-[(1R,2R)-2-Hydroxycyclohexyl]-1-(1-methyl-1H-pyrazol-4-ylmethyl)-4-fluoro-1H-indole-3-carboxamide;
N-[(1S,2S)-2-Hydroxycyclohexyl]-1-(1-methyl-1H-indazol-3-ylmethyl)-4,7-difluoro-1H-indole-3-carboxamide;
N-[(1S,2S)-2-Hydroxycyclohexyl]-1-(1-methyl-1H-pyrazol-4-ylmethyl)-4,7-difluoro-1H-indole-3-carboxamide;
N-[(1S,1S)-2-Hydroxycyclohexyl]-1-(2-Chloropyridin-4-ylmethyl)-4,7-difluoro-1H-indole-3-carboxamide;
N-[(1S,1S)-2-Hydroxycyclohexyl]-1-(2-fluoropyridin-4-ylmethyl)-4-fluoro-1H-indole-3-carboxamide;
N-[(1S,1S)-2-Hydroxycyclohexyl]-1-(2-fluoropyridin-4-ylmethyl)-4,7-difluoro-1H-indole-3-carboxamide;
N-[(1S,1S)-2-Hydroxycyclohexyl]-1-(3-fluoropyridin-4-ylmethyl)-4-fluoro-1H-indole-3-carboxamide;
N-[(1S,1S)-2-Hydroxycyclohexyl]-1-(5-fluoropyridin-4-ylmethyl)-4,7-difluoro-1H-indole-3-carboxamide;
N-[(1S,1S)-2-Hydroxycyclohexyl]-1-(2,5-difluoropyridin-4-ylmethyl)-4-fluoro-1H-indole-3-carboxamide;
N-[(1S,1S)-2-Hydroxycyclohexyl]1-(2,5-difluoro-pyridin-4-ylmethyl)-4,7-difluoro-1H-indole-3-carboxamide;
N-[(1S,2S)-2-Hydroxycyclohexyl]-1-(2,3-difluoropyridin-4-ylmethyl)-4-fluoro-1H-indole-3-carboxamide;
N-[(1S,2S)-2-Hydroxycyclohexyl]-1-(1-pyridin-4-ylmethyl)-4-fluoro-1H-indole-3-carboxamide;
N-[(1S,2S)-2-Hydroxycyclohexyl]-1-(1H-pyrazol-4-ylmethyl)-4-fluoro-1H-indole-3-carboxamide;
N-[(1S,2S)-2-Hydroxycyclohexyl]-1-(2-bromothiazol-5-ylmethyl)-4-fluoro-1H-indole-3-carboxamide;
N-[(1S,2S)-2-Hydroxycyclohexyl]-1-(1-ethyl-5-methyl-1H-pyrazol-4-ylmethyl)-4-fluoro-1H-indole-3-carboxamide;
N-[(1S,2S)-2-Hydroxycyclohexyl]-1-(benzothiazol-6-ylmethyl)-4-fluoro-1H-indole-3-carboxamide;
N-[(1S,2S)-2-Hydroxycyclohexyl] 1-(1-(2-fluoroethyl)-1H-pyrazol-4-ylmethyl)-4-fluoro-1H-indole-3-carboxamide;
N-[(1S,2S)-2-Hydroxycyclohexyl]-1-(2-methylsulfanylpyridin-4-ylmethyl)-4,7-difluoro-1H-indole-3-carboxamide; and
N-[(1S,2S)-2-Hydroxycyclohexyl]-1-(2-methylsulfanylpyridin-4-ylmethyl)-4-fluoro-1H-indole-3-carboxamide;

or a pharmaceutically acceptable salt thereof.

5. A pharmaceutical composition comprising a compound as claimed in claim 1, and pharmaceutically acceptable excipients or carriers.

6. The pharmaceutical composition as claimed in claim 5, for the treatment of clinical conditions mediated through a muscarinic M1 receptor selected from the group consisting of Alzheimer's disease, schizophrenia, cognitive disorders, pain or sleep disorders.

7. A method for treating a disorder related to muscarinic M1 receptor comprising the step of administering to a patient in need thereof a therapeutically effective amount of a compound or a pharmaceutically acceptable salt thereof according to claim 1.

8. The method as claimed in claim 7, wherein the disorder related to muscarinic M1 receptor is selected from the group consisting of Alzheimer's disease, schizophrenia, cognitive disorders, pain or sleep disorders.

* * * * *